(12) United States Patent
Meek

(10) Patent No.: US 6,294,334 B1
(45) Date of Patent: *Sep. 25, 2001

(54) GENETIC TEST FOR EQUINE SEVERE COMBINED IMMUNODEFICIENCY DISEASE

(75) Inventor: Katheryn D. Meek, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/407,562

(22) Filed: Sep. 28, 1999

Related U.S. Application Data

(63) Continuation of application No. 08/970,269, filed on Nov. 14, 1997, now Pat. No. 5,976,803.
(60) Provisional application No. 60/031,261, filed on Nov. 15, 1996.

(51) Int. Cl.[7] .............................. C12Q 1/68; C12P 19/34; C07H 21/04
(52) U.S. Cl. ........................ 435/6; 435/91.2; 435/194; 530/350; 536/23.2; 536/23.5
(58) Field of Search ............................... 435/6, 91.2, 194; 530/350; 536/23.2, 23.5

(56) References Cited

U.S. PATENT DOCUMENTS

| | | | |
|---|---|---|---|
| 3,654,090 | 4/1972 | Schuurs et al. | 435/7 |
| 3,850,752 | 11/1974 | Schuurs et al. | 195/103.5 R |
| 4,016,043 | 4/1977 | Schuurs et al. | 195/103.5 R |
| 5,476,996 | * 12/1995 | Wilson et al. | 800/2 |

OTHER PUBLICATIONS

Wiler et al., Proc. Natl. Acad. Sci. U.S.A. 92, 11485–11489 (1995).*
Wiler et al., Vet. Immunol. Immunopath. 54, 19 (1996).*
Shin et al., J. Am. Vet. Med. Assoc. 211(10), 1268–1270 (1997).*
Bosma et al., "A severe combined immunodeficiency mutation in the mouse" ABSTRACT, *Nature,* 301(5900):527–30, 1983.
McGuire and Poppie, "Hypogammaglobulinemia and thymic hypoplasia in horses: a primary combined immunodeficiency disorder," *Infect. Immun.*, 8(2):272–7, 1973.
Poltoratsky et al., "Human DNA–activated protein kinase (DNA–PK) is homologous to phosphatidylinositol kinases," *J Immunol.*, 155(10):4529–33, 1995.
Hartley, K. O. et al. "DNA–dependent protein kinase catalytic subunit: a relative of phosphatidylinositol 3–kinase and the ataxia telangiectasia gene product." ABSTRACT, *Cell,* 82(5):849–56, 1995.
Blunt T. et al. "Identification of a nonsense mutation in the carboxyl–terminal region of DNA–dependent protein kinase catalytic subunit in the scid mouse" ABSTRACT, *Proc. Natl. Acad. Sci. USA,* 93(19):10285–90, 1996.
Danska J. S. et al. "Biochemical and genetic defects in the DNA–dependent protein kinase in murine scid lymphocytes" ABSTRACT, *Mol. Cell Biol.,* 16(10):5507–17, 1996.
Errami et al. "Ku86 defines the genetic defect and restores X–ray resistance and V(D)J recombination to complementation group 5 hamster cell mutants," ABSTRACT, *Mol Cell Biol.,* 16(4):1519–26, 1996.

(List continued on next page.)

Primary Examiner—Kenneth R. Horlick
(74) Attorney, Agent, or Firm—Fulbright & Jaworski

(57) ABSTRACT

The present invention relates to the discovery of the mutation of a DNA-dependent protein kinase protein which results in equine severe combined immunodeficiency (SCID). Specifically, the present invention provides the sequence of the normal and SCID DNA-dependent protein kinase genes, proteins, and provides diagnostic tests for identifying carriers of the mutation utilizing oligonucleotides that differentiate between the normal and the SCID alleles.

14 Claims, 19 Drawing Sheets

OTHER PUBLICATIONS

Bailey et al., "Linkage of the gene for equine combined immunodeficiency diseaseto microsattelite markers HTG8 and HTG4; synteny and FISH mapping to EAC9," *Animal Genetics*, 28:268–273, 1997.

Shin et al., "A kinase–negative mutation of DNA–PK$_{cs}$ in equine SCID results in defective coding and signal joint formation," *J. Immun.*, 158:3565–3569, 1997.

\* cited by examiner

```
v180       v190       v200       v210       v220
VYELLGLLGEVHPSEMINNAENLFRAFLGELKTQMTSAVREPKLPVLAGC
||||||:|||||||||||:|:|:|||||||||||:||||:|||||||||||
VYELLGVLGEVHPSEMISNSEQLFRAFLGELKSQMTSTVREPKLPVLAGC
         ^10       ^20       ^30       ^40       ^50
      v230       v240       v250       v260       v270
LKGLSSLLCNFTKSMEEDPQTSREIFNFVLKAIRPQIDLKRYAVPSAGLR
|||||||:|||||||||||||||||||:|.|||||||||||||||| |||
LKGLSSLMCNFTKSMEEDPQTSREIFDFALKAIRPQIDLKRYAVPLAGLC
         ^60       ^70       ^80       ^90       ^100
      v280       v290       v300       v310       v320
LFALHASQFSTCLLDNYVSLFEVLLKWCAHTNVELKKAALSALESFLKQV
||:|||||||||||:|||||||||| |||:|||:||||| |||||||||||
LFTLHASQFSTCLLENYVSLFEVLSKWCGHTNIELKKAAHSALESFLKQV
         ^110      ^120      ^130      ^140      ^150
      v330       v340       v350       v360       v370
SNMVAKNAEMHKNKLQYFMEQFYGIIRNVDSNNKELSIAIRGYGLFAGPC
| ||||:||.|||||||||||||||||||:|||:|:|||||||||||||||
SFMVAKDAERHKNKLQYFMEQFYGIIRNMDSNSKDLSIAIRGYGLFAGPC
         ^160      ^170      ^180      ^190      ^200
      v380       v390       v400       v410       v420
KVINAKDVDFMYVELIQRCKQMFLTQTDTGDYRVYQMPSFLQSVASVLLY
||||||||||||||||||||||:|||||||| | :::||||||||:.|||||
KVINAKDVDFMYVELIQRCKQLFLTQTDTVDDHIYQMPSFLQSIVSVLLY
         ^210      ^220      ^230      ^240      ^250
      v430       v440       v450       v460       v470
LDTVPEVYTPVLEHLVVMQIDSFPQYSPKMQLVCCRAIVKVFLALAAKGP
|||:|||||||||||:|:||||||||||||||| ||||||||:|||||.|||
LDTIPEVYTPVLEHLMVVQIDSFPQYSPKMQPVCCRAIVKLFLALAEKGP
         ^260      ^270      ^280      ^290      ^300
      v480       v490       v500       v510       v520
VLRNCISTVVHQGLIRICSKPVVLPKGPESESEDHRASGEVRTGKWKVPT
||:||||||||||||||||||||:.||:.||||.::|.|.||||||:||
VLWNCISTVVHQGLIRICSKPVVFQKGAGSESEDYHTSEEARTGKWKMPT
         ^310      ^320      ^330      ^340      ^350
```

FIGURE 2A

```
        v530       v540       v550       v560       v570
YKDYVDLFRHLLSSDQMMDSILADEAFFSVNSSSESLNHLLYDEFVKSVL
||||:||||.|||.||||||:||||||: |||| :|||:|||||||||||
YKDYLDLFRYLLSCDQMMDSLLADEAFLFVNSSLHSLNRLLYDEFVKSVL
        ^360       ^370       ^380       ^390       ^400
        v580       v590       v600       v610       v620
KIVEKLDLTLEIQTVGEQENGDEAPGVWMIPTSDPAANLHPAKPKDFSAF
||||||||| |.|||||:..||.|||:|||||||||||||||||||||
KIVEKLDLTLEKQNVGEQEDETEATGVWVIPTSDPAANLHPAKPKDFSAF
        ^410       ^420       ^430       ^440       ^450
        v630       v640       v650       v660       v670
INLVEFCREILPEKQAEFFEPWVYSFSYELILQSTRLPLISGFYKLLSIT
|||||||||||||:.|||||||||||:||||||||||||| ||||||::
INLVEFCREILPEKHVEFFEPWVYSFAYELILQSTRLPLISVFYKLLSVA
        ^460       ^470       ^480       ^490       ^500
        v680       v690       v700       v710       v720
VRNAKKIKYFEGVSPKSLKHSPEDPEKYSCFALFVKFGKEVAVKMKQYKD
||||||:||||||:||| |:|||| |||||||||||.||:|||::||||||
VRNAKKMKYFEGVGPKSQKQSPEDLEKYSCFALFAKFSKEVSIKMKQYKD
        ^510       ^520       ^530       ^540       ^550
        v730       v740       v750       v760       v770
ELLASCLTFLLSLPHNIIELDVRAYVPALQMAFKLGLSYTPLAEVGLNAL
|||||||||:|||||:|||||||||||||||||||||||||||||||||
ELLASCLTFILSLPHDIIELDVRAYVPALQMAFKLGLSYTPLAEVGLNAL
        ^560       ^570       ^580       ^590       ^600
        v780       v790       v800       v810       v820
EEWSIYIDRHVMQPYYKDILPCLDGYLKTSALSDETKNNWEVSALSRAAQ
|||| || :||:||||||||.||||||||.||||||:|:|||||||||
EEWSGYICKHVIQPYYKDILPSLDGYLKTSVLSDETKNSWQVSALSRAAQ
        ^610       ^620       ^630       ^640       ^650
        v830       v840       v850       v860       v870
KGFNKVVLKHLKKTKNLSSNEAISLEEIRIRVVQMLGSLGGQINKNLLTV
||||||||||||.|||::||||:||||:||||:||||::||||||||:|.
KGFNKVVLKHLTKTKSISSNEALSLEEVRIRVVRILGSLGGQINKNLVTA
        ^660       ^670       ^680       ^690       ^700
```

FIGURE 2B

```
      v880        v890        v900        v910        v920
TSSDEMMKSYVAWDREKRLSFAVPFREMKPVIFLDVFLPRVTELALTASD
:||||||||..|||||||||.|||||.||||||:||:||||||||||:|||
ASSDEMMKKCVAWDREKRLRFAVPFMEMKPVIYLDLFLPRVTELALSASD
      ^710        ^720        ^730        ^740        ^750
      v930        v940        v950        v960        v970
RQTKVAACELLHSMVMFMLGKATQMPEGGQGAPPMYQLYKRTFPVLLRLA
|||.|||||||||||||||||||||||||:|||:|||||||||||||||
RQTTVAACELLHSMVMFMLGKATQMPEDGQGSPPMYQLYKRTFPVLLRLA
      ^760        ^770        ^780        ^790        ^800
      v980        v990        v1000       v1010       v1020
CDVDQVTRQLYEPLVMQLIHWFTNNKKFESQDTVSLLEAILDGIVDPVDS
|||||||||||||||||||||||||||||||||:|||:|||||||||||
CDVDQVTRQLYEPLVMQLIHWFTNNKKFESQDTVALLETILDGIVDPVDS
      ^810        ^820        ^830        ^840        ^850
      v1030       v1040       v1050       v1060       v1070
TLRDFCGRCIREFLKWSIKQITPQQQEKSPVNTKSLFKRLYSLALHPNAF
||||||:||:||||||||.||||||||||||||||||||||:|||||||
TLRDFCGQCIQEFLKWSIKQTTPQQQEKSPVNTKSLFKRLYSFALHPNAF
      ^860        ^870        ^880        ^890        ^900
      v1080       v1090       v1100       v1110       v1120
KRLGASLAFNNIYREFREEESLVEQFVFEALVIYMESLALAHADEKSLGT
|||||||||||||||||||||||||||||||.||||||||:||||||||
KRLGASLAFNNIYREFREEESLVEQFVFEALVTYMESLALAHTDEKSLGT
      ^910        ^920        ^930        ^940        ^950
      v1130       v1140       v1150       v1160       v1170
IQQCCDAIDHLCRIIEKKHVSLNKAKKRRLPRGFPPSASLCLLDLVKWLL
||||||||||.||||||||||||||||||||||||::||||||:|:|||
IQQCCDAIDHLSLIIEKKHVSLNKAKKRRLPRGFPPATSLCLLDVVQWLL
      ^960        ^970        ^980        ^990        ^1000
      v1180       v1190       v1200       v1210       v1220
AHCGRPQTECRHKSIELFYKFVPLLPGNRSPNLWLKDVLKEEGVSFLINT
|:||||||||||||||||||||.||||:||||||::|.|::|||||||
ANCGRPQTECRHKSIELFYKFVTLLPGNKSPFLWLKDIIKKEDISFLINT
      ^1010       ^1020       ^1030       ^1040       ^1050
```

FIGURE 2C

```
            v1230       v1240       v1250       v1260       v1270
FEGGGCGQPSGILAQPTLLYLRGPFSLQATLCWLDLLLAALECYNTFIGE
|||||.|:|||||||||||:.|:||||:|:|  |:|:|||||||||||.|
FEGGGSGRPSGILAQPTLFHLQGPFSLRAALQWMDMLLAALECYNTFIEE
        ^1060       ^1070       ^1080       ^1090       ^1100
            v1280       v1290       v1300       v1310       v1320
RTVGALQVLGTEAQSSLLKAVAFFLESIAMHDIIAAEKCFGTGAAGNRTS
:|:.|  :|||||:||||  |||||||||||||||:||||.|||||:|||.|
KTLEAPKVLGTETQSSLWKAVAFFLESIAMHDIMAAEKYFGTGATGNRPS
        ^1110       ^1120       ^1130       ^1140       ^1150
            v1330       v1340       v1350       v1360       v1370
PQEGERYNYSKCTVVVRIMEFTTTLLNTSPEGWKLLKKDLCNTHLMRVLV
|||||||||||||:|||||||||||:|||||||||.||:|||:|::||
PQEGERYNYSKCTIVVRIMEFTTTLLSTSPEGWKLLEKDVCNTNLMKLLV
        ^1160       ^1170       ^1180       ^1190       ^1200
            v1380       v1390       v1400       v1410       v1420
QTLCEPASIGFNIGDVQVMAHLPDVCVNLMKALKMSPYKDILETHLREKI
:|||||:|||||||||.||..||.||.|||||||.|||||||| ||:|||
KTLCEPSSIGFNIGDVAVMNYLPSVCTNLMKALKKSPYKDILEMHLKEKI
        ^1210       ^1220       ^1230       ^1240       ^1250
            v1430       v1440       v1450       v1460       v1470
TAQSIEELCAVNLYGPDAQVDRSRLAAVVSACKQLHRAGLLHNILPSQST
||||||||||:|| ||| |||:|||:||||||||||||||:|  |:||||:
TAQSIEELCAVDLYCPDACVDRARLASVVSACKQLHRAGVLCVIIPSQSA
        ^1260       ^1270       ^1280       ^1290       ^1300
            v1480       v1490       v1500       v1510       v1520
DLHHSVGTELLSLVYKGIAPGDERQCLPSLDLSCKQLASGLLELAFAFGG
| |||:||.|||||||||:||||||||||||  :||||||||||||||||
DQHHSIGTKLLSLVYKSIAPGDEQQCLPSLDPNCKRLASGLLELAFAFGG
        ^1310       ^1320       ^1330       ^1340       ^1350
            v1530       v1540       v1550       v1560       v1570
LCERLVSLLLNPAVLSTASLGSSQGSVIHFSHGEYFYSLFSETINTELLK
|||:|||||:..|||  :|  |:||  :::  ||||||||||||||||||
LCEHLVSLLLDTTVLSMPSRGGSQKNIVSFSHGEYFYSLFSETINTELLK
        ^1360       ^1370       ^1380       ^1390       ^1400
```

FIGURE 2D

```
         v1580       v1590       v1600       v1610       v1620
NLDLAVLELMQSSVDNTKMVSAVLNGNLDQSFRERANQKHQGLKLATTIL
||||||||||:|||||.||||.|||||||||||:|:::|||||||||.||
NLDLAVLELMKSSVDNPKMVSNVLNGMLDQSFRDRTSEKHQGLKLATIIL
         ^1410       ^1420       ^1430       ^1440       ^1450
         v1630       v1640       v1650       v1660       v1670
QHWKKCDSWWAKDSPLETKMAVLALLAKILQIDSSVSFNTSHGSFPEVFT
|:||||||||||||:  |:||||||||||:||||||.|||:|  ||||||
QNWKKCDSWWAKDSAPESKMAVLTLLAKIFQIDSSVCFNTNHCMFPEVFT
         ^1460       ^1470       ^1480       ^1490       ^1500
         v1680       v1690       v1700       v1710       v1720
TYISLLADTKLDLHLKGQAVTLLPFFTSLTGGSLEELRRVLEQLIVAHFP
||:||||||:|||||||||:.|||||||||||||||:|: |||:|||::||
TYVSLLADSKLDLHLKGQAIILLPFFTSLTGGSLEDLKVVLENLIVSNFP
         ^1510       ^1520       ^1530       ^1540       ^1550
         v1730       v1740       v1750       v1760       v1770
MQSREFPPGTPRFNNYVDCMKKFLDALELSQSPMLLELMTEVLCREQQHV
|:| ||||||  ::::|||||||||||||||:|||||:||||:|||||||
MKSEEFPPGTLQYNNYVDCMKKFLDALELSKSPMLLQLMTEILCREQQHV
         ^1560       ^1570       ^1580       ^1590       ^1600
         v1780       v1790       v1800       v1810       v1820
MEELFQSSFRRIARRGSCVTQVGLLESVYEMFRKDDPRLSFTRQSFVDRS
|||||||:|:::|||::||:||:|||||||| |||:||   ::|||:|||||
MEELFQSTFKKIARKSSCITQLGLLESVYRMFRRDDLLSNITRQAFVDRS
         ^1610       ^1620       ^1630       ^1640       ^1650
         v1830       v1840       v1850       v1860       v1870
LLTLLWHCSLDALREFFSTIVVDAIDVLKSRFTKLNESTFDTQITKKMGY
||||||||||:|||||||.|||:||||||||.|||||:|||||||||||
LLTLLWHCSLNALREFFSKIVVEAINVLKSRFIKLNESAFDTQITKKMGY
         ^1660       ^1670       ^1680       ^1690       ^1700
         v1880       v1890       v1900       v1910       v1920
YKILDVMYSRLPKDDVHAKESKINQVFHGSCITEGNELTKTLIKLCYDAF
||:||||||||||||||:|||||||||||||||||:|||||||||||||
YKMLDVMYSRLPKDDVHSKESKINQVFHGSCITEGSELTKTLIKLCYDAF
         ^1710       ^1720       ^1730       ^1740       ^1750
```

FIGURE 2E

```
        v1930       v1940       v1950       v1960       v1970
TENMAGENQLLERRRLYHCAAYNCAISVICCVFNELKFYQGFLFSEKPEK
|||||||||||||||||||||||||||:||||||||||||||||:|||||
TENMAGENQLLERRRLYHCAAYNCAISVVCCVFNELKFYQGFLFTEKPEK
        ^1760       ^1770       ^1780       ^1790       ^1800
        v1980       v1990       v2000       v2010       v2020
NLLIFENLIDLKRRYNFPVEVEVPMERKKKYIEIRKEARE-AANGDSDGP
||||||||||||| |.||:|||||||||||:|||||||| ||:||||||
NLLIFENLIDLKRCYTFPIEVEVPMERKKKYLEIRKEAREAAASGDSDGP
        ^1810       ^1820       ^1830       ^1840       ^1850
        v2030       v2040       v2050       v2060       v2070
SYMSSLSYLADSTLSEEMSQFDFSTGVQSYSYSSQDPRPATGRFRRREQR
.|:||||||||:||||||||||||||||||||||||||:::|::|||:..:
RYISSLSYLADSSLSEEMSQFDFSTGVQSYSYSSQDPKSTTAHFRRQKHK
        ^1860       ^1870       ^1880       ^1890       ^1900
        v2080       v2090       v2100       v2110       v2120
DPTVHDDVLELEMDELNRHECMAPLTALVKHMHRSLGPPQGEEDSVPRDL
:: ::||:||||||||:||||..|||:|||:|:     |:.||:||||:|
ESMIQDDILELEMDELNQHECMATMTALIKHMQRNQILPKEEEGSVPRNL
        ^1910       ^1920       ^1930       ^1940       ^1950
        v2130       v2140       v2150       v2160       v2170
PSWMKFLHGKLGNPIVPLNIRLFLAKLVINTEEVFRPYAKHWLSPLLQLA
|:||||||:|||||| ::|||||||||||||||||||||||:.||||||||.
PPWMKFLHDKLGNPSISLNIRLFLAKLVINTEEVFRPYARYWLSPLLQLV
        ^1960       ^1970       ^1980       ^1990       ^2000
        v2180       v2190       v2200       v2210       v2220
ASENNGGEGIHYMVVEIVATILSWTGLATPTGVPKDEVLANRLLNFLMKH
.|.|||||||||||||||..|||||||||.||||||||||||||:|||||
VSGNNGGEGIHYMVVEIVVIILSWTGLATPIGVPKDEVLANRLLHFLMKH
        ^2010       ^2020       ^2030       ^2040       ^2050
        v2230       v2240       v2250       v2260       v2270
VFHPKRAVFRHNLEIIKTLVECWKDCLSIPYRLIFEKFSGKDPNSKDNSV
|||.|||||||||||||||||||||||||||||||||||||:.|||||||
VFHQKRAVFRHNLEIIKTLVECWKDCLSIPYRLIFEKFSSTDPNSKDNSV
        ^2060       ^2070       ^2080       ^2090       ^2100
```

*FIGURE 2F*

```
           v2280       v2290       v2300       v2310       v2320
       GIQLLGIVMANDLPPYDPQCGIQSSEYFQALVNNMSFVRYKEVYAAAAEV
       ||||||||||:||||||:|||:|.|||||||||||||:|||||||||
       GIQLLGIVMANNLPPYDPKCGIESIKYFQALVNNMSFVRYREVYAAAAEV
           ^2110       ^2120       ^2130       ^2140       ^2150
           v2330       v2340       v2350       v2360       v2370
       LGLILRYVMERKNILEESLCELVAKQLKQHQNTMEDKFIVCLNKVTKSFP
       |||:|||:.||.|||||||||||  |||||||||||||||||||..|:||
       LGLVLRYITERENILEESVCELVIKQLKQHQNTMEDKFIVCLNKAVKNFP
           ^2160       ^2170       ^2180       ^2190       ^2200
           v2380       v2390       v2400       v2410       v2420
       PLADRFMNAVFFLLPKFHGVLKTLCLEVVLCRVEGMTELYFQLKSKDFVQ
       |||||||:|||||||||||:||||||||||.|.:|:||:|||||||:|
       PLADRFMNTVFFLLPKFHGVMKTLCLEVVLCRAEEITDLYLQLKSKDFIQ
           ^2210       ^2220       ^2230       ^2240       ^2250
           v2430       v2440       v2450       v2460       v2470
       VMRHR-DERQKVCLDIIYKMMPKLKPVELRELLNPVVEFVSHPSTTCREQ
       |||||  |||||||||||||::|||||||||||||||:||||..||||
       VMRHRDDERQKVCLDIIYKMMARLKPVELRELLNPVVEFISHPSPVCREQ
           ^2260       ^2270       ^2280       ^2290       ^2300
           v2480       v2490       v2500       v2510       v2520
       MYNILMWIHDNYRDPESETDNDSQEIFKLAKDVLIQGLIDENPGLQLIIR
       ||||||||||||||::||:||||||||||||||||||||||||||||||
       MYNILMWIHDNYRDPEGQTDDDSQEIFKLAKDVLIQGLIDENPGLQLIIR
           ^2310       ^2320       ^2330       ^2340       ^2350
           v2530       v2540       v2550       v2560       v2570
       NFWSHETRLPSNTLDRLLALNSLYSPKIEVHFLSLATNFLLEMTSMSPDY
       ||||||||||||||||||||||||||||.|||||||:||||||:||||
       NFWSHETRLPSNTLDRLLALNSLYSPKIEAHFLSLATDFLLEMTSVSPDY
           ^2360       ^2370       ^2380       ^2390       ^2400
           v2580       v2590       v2600       v2610       v2620
       PNPMFEHPLSECEFQEYTIDSDWRFRSTVLTPMFVETQASQGTLQTRTQE
       :||||:|||||||.||||||||||||||||||||:|||||::||||||||
       SNPMFDHPLSECKFQEYTIDSDWRFRSTVLTPMFIETQASQSALQTRTQE
           ^2410       ^2420       ^2430       ^2440       ^2450
```

FIGURE 2G

```
            v2630       v2640       v2650       v2660       v2670
GSLSARWPVAGQIRATQQQHDFTLTQTADGRSSFDWLTGSSTDPLVDHT-
||||||  ::|||||||||.||| ||.:||||||:||||:|.||||| |
GSLSARGVMTGQIRATQQQYDFTPTQNTDGRSSFNWLTGNSIDPLVDFTV
         ^2460       ^2470       ^2480       ^2490       ^2500
            v2680       v2690       v2700       v2710
SPSSDS----LLFAHKRSERLQRAPLKSVGPDFGKKRLGLPGDEVDNKVK
|:||||    |||||||||: ||:||||||||||||||||||||||.|
SSSSDSLSSSLLFAHKRSEKSQRGPLKSVGPDFGKKRLGLPGDEVDNKAK
         ^2510       ^2520       ^2530       ^2540       ^2550
    v2720       v2730       v2740       v2750       v2760
GAAGRTDLLRLRRRFMRDQEKLSLMYARKGVAEQKREKEIKSELKMKQDA
|:..|:::|||||||::|:|||||:||||||||||||||||||||:||
GTDNRAEILRLRRRFLKDREKLSLIYARKGVAEQKREKEIKSELKMKHDA
         ^2560       ^2570       ^2580       ^2590       ^2600
    v2770       v2780       v2790       v2800       v2810
QVVLYRSYRHGDLPDIQIKHSSLITPLQAVAQRDPIIAKQLFSSLFSGIL
||:|||||:||||||||.|||||||||||||||||||||||:||||||:
QVILYRSYRQGDLPDIQIKYSSLITPLQAVAQRDPIIAKQLFGSLFSGII
         ^2610       ^2620       ^2630       ^2640       ^2650
    v2820       v2830       v2840       v2850       v2860
KEMDKFKTLSEKNNITQKLLQDFNRFLNTTFSFFPPFVSCIQDISCQHAA
|||||:||:|||||||||||||||.|||||  ||||||:||||:|||||.
KEMDKYKTMSEKNNITQKLLQDFNNFLNTTVSFFPPFISCIQEISCQHAD
         ^2660       ^2670       ^2680       ^2690       ^2700
    v2870       v2880       v2890       v2900       v2910
LLSLDPAAVSAGCLASLQQPVGIRLLEEALLRLLPAELPAKRVRGKARLP
|||||:|||:|||||||||||||:|||||||.| ||||||||||::  |
LLSLDPASVSASCLASLQQPVGVRLLEEALLHLLPEEPPAKRVRGRPCLY
         ^2710       ^2720       ^2730       ^2740       ^2750
    v2920       v2930       v2940       v2950       v2960
PDVLRWVELAKLYRSIGEYDVLRGIFTSEIGTKQITQSALLAEARSDYSE
|| :||:||||||||||||||:|||||.||||||:|||||||||:||||
PDFVRWMELAKLYRSIGEYDILRGIFNSEIGTKQVTQNALLAEARNDYSE
         ^2760       ^2770       ^2780       ^2790       ^2800
```

FIGURE 2H

```
         v2970     v2980      v2990     v3000      v3010
AAKQYDEALNKQDWVDGEPTEAEKDFWELASLDCYNHLAEWKSLEYCSTA
|.|||:||||||||||| |||||||||||||||||:|||||||.||||.
AVKQYNEALNKQDWVDGEPMEAEKDFWELASLDCYNQLAEWKSLAYCSTV
         ^2810     ^2820      ^2830     ^2840      ^2850
         v3020     v3030      v3040     v3050      v3060
SIDSENPPDLNKIWSEPFYQETYLPYMIRSKLKLLLQGEADQSLLTFIDK
|:||.|||||||:|:|||||||||||||||||||||||:|||||||||.
SVDSANPPDLNKMWNEPFYQETYLPYMIRSKLKLLLQGEGDQSLLTFIDE
         ^2860     ^2870      ^2880     ^2890      ^2900
         v3070     v3080      v3090     v3100      v3110
AMHGELQKAILELHYSQELSLLYLLQDDVDRAKYYIQNGIQSFMQNYSSI
|:  ||||.::||||||||||||:|||||||||||:| |: |||:||||
AVSKELQKVLVELHYSQELSLLYILQDDVDRAKYYIENCIRIFMQSYSSI
         ^2910     ^2920      ^2930     ^2940      ^2950
         v3120     v3130      v3140     v3150      v3160
DVLLHQSRLTKLQSVQALTEIQEFISFISKQGNLSSQVPLKRLLNTWTNR
||||::||||||||:|||.||||||||||.||||||||:||||||:|||||
DVLLERSRLTKLQSLQALIEIQEFISFIRKQGNLSSQIPLKRLLKTWTNR
         ^2960     ^2970      ^2980     ^2990      ^3000
         v3170     v3180      v3190     v3200      v3210
YPDAKMDPMNIWDDIITNRCFFLSKIEEKLTPLPEDNSMNVDQDGDPSDR
|||||||||||||||||||||||||||||| |:|||.| |.|:|||
YPDAKMDPMNIWDDIITNRCFFLSKIEEKLTIPPDDHSMNTDGDEDSSDR
         ^3010     ^3020      ^3030     ^3040      ^3050
         v3220     v3230      v3240     v3250      v3260
MEVQEQEEDISSLIRSCKFSMKMKMIDSARKQNNFSLAMKLLKELHKESK
|.|||||||| |||:| ||||||||:|||||:|||||||||||||||||
MKVQEQEEDIYSLIKSGKFSMKMKMIESARKQKNFSLAMKLLKELHKESK
         ^3060     ^3070      ^3080     ^3090      ^3100
         v3270     v3280      v3290     v3300      v3310
TRDDWLVSWVQSYCRLSHCRSRSQGCSEQVLTVLKTVSLLDENNVSSYLS
|||||||.|||||||||.||::|.  :||:|||||||||||||. |||||
TRDDWLVKWVQSYCRLSHSRSQTQNRPEQILTVLKTVSLLDENT-SSYLS
         ^3110     ^3120      ^3130     ^3140
```

FIGURE 2I

```
     v3320      v3330      v3340      v3350      v3360
KNILAFRDQNILLGTTYRIIANALSSEPACLAEIEEDKARRILELSGSSS
||| . ||:|||||||||||||||||:|:|||||.|.|||||||||||||
KNIPVSRDHNILLGTTYRIIANALSSDPTCLAEIGESKARRILELSGSSL
^3150      ^3160      ^3170      ^3180      ^3190
     v3370      v3380      v3390      v3400      v3410
EDSEKVIAGLYQRAFQHLSEAVQAAEEEAQPPSWSCGPAAGVIDAYMTLA
|::|.|||||||||.::|||||: ||||||| ::: .||.||||||||.
ENAEEVIAGLYQRVLHHLSEAVRIAEEEAQPFTRGGQEPAVGVIDAYMTLV
^3200      ^3210      ^3220      ^3230      ^3240
     v3420      v3430      v3440      v3450      v3460
DFCDQQLRKEEENASVTDSAELQAYPALVVEKMLKALKLNSNEARLKFPR
|||||||||||||::|||:|.:|| ||||||:||||||:|:|||||||||
DFCDQQLRKEEESSSVTESVQLQMYPALVVDKMLKALRLDSNEARLKFPR
^3250      ^3260      ^3270      ^3280      ^3290
     v3470      v3480      v3490      v3500      v3510
LLQIIERYPEETLSLMTKEISSVPCWQFISWISHMVALLDKDQAVAVQHS
|||||||||||||||||||||||:||||||:||||||||||||::||||:::
LLQIIERYPEETLSLMTKEISSIPCWQFIGWISHMVALLDKEEAVAVHRT
^3300      ^3310      ^3320      ^3330      ^3340
     v3520      v3530      v3540      v3550      v3560
VEEITDNYPQAIVYPFIISSESYSFKDTSTGHKNKEFVARIKSKLDQGGV
||||:||||||:|||||||||||||||||||.|||||.||| |||||||
VEEIADNYPQAMVYPFIISSESYSFKDTSTGYKNKEFVERIKIKLDQGGV
^3350      ^3360      ^3370      ^3380      ^3390
     v3570      v3580      v3590      v3600      v3610
IQDFINALDQLSNPELLFKDWSNDVRAELAKTPVNKKNIEKMYERMYAAL
||||||||:|||:|||||||::|::.||.|.|||||||||||||:|||:|
IQDFINALEQLSHPEMLFKDWTDDIKVELEKNPVNRKNIEKMYEKMYATL
^3400      ^3410      ^3420      ^3430      ^3440
     v3620      v3630      v3640      v3650      v3660
GDPKAPGLGAFRRKFIQTFGKEFDKHFGKGGSKLLRMKLSDFNDITNMLL
|||:|||||||||: ||.||||||||||||:||||| || ..:|:|||| |:
GDPQAPGLGAFRRRCIQGFGKEFDKHFGRGGSKLPGMKSREFSDITNSLF
^3450      ^3460      ^3470      ^3480      ^3490
```

FIGURE 2J

```
       v3670     v3680     v3690     v3700     v3710
LKMNKDSKPPGNLKECSPWMSDFKVEFLRNELEIPGQYDGRGKPLPEYHV
|| . |||||||||||||||||||||||||:|||||||||||:|||:||||.
SKMCEVSKPPGNLKECSPWMSDFKVEFLRSELEIPGQYDGKGKPVPEYHA
 ^3500     ^3510     ^3520     ^3530     ^3540
       v3720     v3730     v3740     v3750     v3760
RIAGFDERVTVMASLRRPKRIIIRGHDEREHPFLVKGGEDLRQDQRVEQL
||||||||:.|||:|:|||||||||||||.|||||||||||||||||:|||
RIAGFDERIKVMASMRKPKRIIIRGHDEREYPFLVKGGEDLRQDQRIEQL
 ^3550     ^3560     ^3570     ^3580     ^3590
       v3770     v3780     v3790     v3800     v3810
FQVMNGILAQDSACSQRALQLRTYSVVPMTSRLGLIEWLENTVTLKDLLL
|:||| ||:|::||||::|||:|| |:|||||||||||:||| |||:|||
FEVMNVILSQDATCSQRSMQLKTYQVIPMTSRLGLIEWIENTFTLKELLL
 ^3600     ^3610     ^3620     ^3630     ^3640
       v3820     v3830     v3840     v3850     v3860
NTMSQEEKAAYLSDPRAPPCEYKDWLTKMSGKHDVGAYMLMYKGANRTET
:.|||||||| . ||:||| ||:||||||||| |||||||||||||:||||
SNMSQEEKAACTRDPKAPPFEYRDWLTKMSGKCDVGAYMLMYKGASRTET
 ^3650     ^3660     ^3670     ^3680     ^3690
       v3870     v3880     v3890     v3900     v3910
VTSFRKRESKVPADLLKRAFVRMSTSPEAFLALRSHFASSHALICISHWI
||||||||||||||||||||:|||||||||:||||||:||||||||||||
VTSFRKRESKVPADLLKRAFVKMSTSPEAFLTLRSHFAGSHALICISHWI
 ^3700     ^3710     ^3720     ^3730     ^3740
       v3920     v3930     v3940     v3950     v3960
LGIGDRHLNNFMVAMETGGVIGIDFGHAFGSATQFLPVPELMPFRLTRQF
|||||||||||:|:||||||||||||||||||||||||||||||||||||
PGIGDRHLNNFLVSMETGGVIGIDFGHAFGSATQFLPVPELMPFRLTRQF
 ^3750     ^3760     ^3770     ^3780     ^3790
       v3970     v3980     v3990     v4000     v4010
INLMLPMKETGLMYSIMVHALRAFRSDPGLLTNTMDVFVKEPSFDWKNFE
|||||||||||:||||||||||||||::.||:||||||||||||||||||
INLMLPMKETGVMYSIMVHALRAFRSQSNLLANTMDVFVKEPSFDWKNFE
 ^3800     ^3810     ^3820     ^3830     ^3840
```

FIGURE 2K

```
         v4020       v4030       v4040       v4050       v4060
QKMLKKGGSWIQEINVAEKNWYPRQKICYAKRKLAGANPAVITCDELLLG
||| |||||||||||:||||||||| |||||||||||||||||||||||
QKMRKKGGSWIQEINVTEKNWYPRQKIHYAKRKLAGANPAVITCDELLLG
^3850       ^3860       ^3870       ^3880       ^3890
         v4070       v4080       v4090       v4100       v4110
HEKAPAFRDYVAVARGSKDHNIRAQEPESGLSEETQVKCLMDQATDPNIL
||||:|| ||||||||||.||||||| ||:||||:|||||:|||||||||
HEKAAAFGDYVAVARGSEDHNIRAQELESDLSEEAQVKCLIDQATDPNIL
^3900       ^3910       ^3920       ^3930       ^3940
         v4120
GRTWEGWEPWM
||| |||||||
GRTLVGWEPWM
^3950      ^3960
```

*FIGURE 2L*

*Normal Probe*   *SCID Probe*

```
                        v10       v20       v30       v40       v50      v60
NORM.SEQ  AGTCATTGGGTCCATTTTAGCATCCGGATATCTGTTTGTCCAGGTTTTTAGAAGTCTCTT
          AGTCATTGGGTCCATTTTAGCATCCGGATATCTGTTTGTCCAGGTTTTTAGAAGTCTCTT
SCID.SEQ  AGTCATTGGGTCCATTTTAGCATCCGGATATCTGTTTGTCCAGGTTTTTAGAAGTCTCTT
                    ^10       ^20       ^30       ^40       ^50      ^60
                        v70       v80       v90       v100      v110     v120

NORM.SEQ  AAGGGGAATTTGAGATGATAAATTACCTAAAAATAATATTAGAGAATGACTATATCCACA
          AAGGGGAATT        TGATAAATTACCTAAAAATAATATTAGAGAATGACTATATCCACA
SCID.SEQ  AAGGGGAATT----TGATAAATTACCTAAAAATAATATTAGAGAATGACTATATCCACA
                    ^70       ^80       ^90       ^100      ^110     ^120
                        v130      v140      v150      v160      v170     v180

NORM.SEQ  GCTCAATGACAAGACCAACTTATAAAGTGAGCTCCTATAGTAAAGAGAAACTTAATTCAA
          GCTCAATGACAAGACCAACTTATAAAGTGAGCTCCTATAGTAAAGAGAAACTTAATTCAA
SCID.SEQ  GCTCAATGACAAGACCAACTTATAAAGTGAGCTCCTATAGTAAAGAGAAACTTAATTCAA
                    ^130      ^140      ^150      ^160      ^170     ^180
                        v190      v200      v210      v220      v230     v240

NORM.SEQ  ATTTCTTGTCCAAATTAAAAAATTCTGTCTCTCCTTTTGCAACAGGAACACAAAGCTACCAT
          ATTTCTTGTCCAAATTAAAAAATTCTGTCTCTCCTTTTGCAACAGGAACACAAAGCTACCAT
SCID.SEQ  ATTTCTTGTCCAAATTAAAAAATTCTGTCTCTCCTTTTGCAACAGGAACACAAAGCTACCAT
                    ^190      ^200      ^210      ^220      ^230     ^240

NORM.SEQ  ATTAAAAC
          ATTAAAAC
SCID.SEQ  ATTAAAAC
```

*FIGURE 4B*

DNA-PKcs, Residues 1-3715

| | |
|---|---|
|  | Subdomain 1 of PI3K domain |
|  | Subdomain 2 of PI3K domain |
|  | Residues homologous to protein kinase active sites |
|  | Subdomain 2 of PI3K domain |

SEQUENCE LISTING (1) GENERAL INFORMATION:

(iii) NUMBER OF SEQUENCES:  32

(2) INFORMATION FOR SEQ ID NO:1:

(i) SEQUENCE CHARACTERISTICS:
      (A) LENGTH:  17 bp
      (B) TYPE:  nucleic acid
      (C) STRANDEDNESS:  double stranded
      (D) TOPOLOGY:  linear (ii) MOLECULE TYPE:
      (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO:1:

GTATATGAGC TCCTAGG                                                          17

(2) INFORMATION FOR SEQ ID NO:2:

(i) SEQUENCE CHARACTERISTICS:
      (A) LENGTH:  18
      (B) TYPE:  nucleic acid
      (C) STRANDEDNESS:  double stranded
      (D) TOPOLOGY:  linear

```
        (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 2:

GGGAGAATCT CTCTGCAA                                                 18

(2) INFORMATION FOR SEQ ID NO:3:

(i) SEQUENCE CHARACTERISTICS:
             (A) LENGTH:  18 bp
             (B) TYPE:  nucleic acid
             (C) STRANDEDNESS:  double stranded
             (D) TOPOLOGY:  linear (ii) MOLECULE TYPE:
             (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO:  3:

TCAGGAGTTC ATCAGCTT                                                 18

(2) INFORMATION FOR SEQ ID NO:4:

(i) SEQUENCE CHARACTERISTICS:
             (A) LENGTH:  18 bp
             (B) TYPE:  nucleic acid
             (C) STRANDEDNESS:  double stranded
             (D) TOPOLOGY:  linear (ii) MOLECULE TYPE:
             (A) DESCRIPTION:  other nucleic acid (iii) HYPOTHETICAL: no (iv) ANTI-SENSE:  no (vi) ORIGINAL SOURCE:

(ix) FEATURE:

(xi) SEQUENCE DESCRIPTION: SEQ ID NO:  4:

GATCCAGCGG CTAACTTG                                                 18

(2) INFORMATION FOR SEQ ID NO:5:

(i) SEQUENCE CHARACTERISTICS:
             (A) LENGTH:  18 bp
             (B) TYPE:  nucleic acid
             (C) STRANDEDNESS:  double stranded
             (D) TOPOLOGY:  linear (ii) MOLECULE TYPE:
             (A) DESCRIPTION:  other nucleic acid (iii) HYPOTHETICAL:  no (iv) ANTI-SENSE:  no
```

(vi) ORIGINAL SOURCE:

(ix) FEATURE:

(xi) SEQUENCE DESCRIPTION: SEQ ID NO: 5:

CATGTGCTAA GGCCAGAC                                                  18

(2) INFORMATION FOR SEQ ID NO:6:

(i) SEQUENCE CHARACTERISTICS:
        (A) LENGTH: 18
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 6:

TCTACAGGGA ATTCAGGG                                                  18

(2) INFORMATION FOR SEQ ID NO:7:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 7:

CACCATGAAT CACACTTC                                                  18

(2) INFORMATION FOR SEQ ID NO:8:

(i) SEQUENCE CHARACTERISTICS:
        (A) LENGTH: 18
        (B) TYPE: nucleic acid
        (C) STRANDEDNESS: double stranded
        (D) TOPOLOGY: linear (ii) MOLECULE TYPE:
        (A) DESCRIPTION: other (iii) HYPOTHETICAL: No (iv) ANTI-SENSE: No (vi) ORIGINAL SOURCE:

(ix) FEATURE:

(xi) SEQUENCE DESCRIPTION: SEQ ID NO: 8:

CACCAAGGAC TGAAACTT                                              18

(2) INFORMATION FOR SEQ ID NO:9:

(i) SEQUENCE CHARACTERISTICS:
        (A) LENGTH: 18
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 9:

GCACTTTCAT TCTGTCAC                                              18

(2) INFORMATION FOR SEQ ID NO:10:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 10:

ATTCATGACC TCGAAGAG                                              18

(2) INFORMATION FOR SEQ ID NO:11:

(i) SEQUENCE CHARACTERISTICS:
        (A) LENGTH: 19 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 11:

TGGACAAACA GATATCCAG                                             19

(2) INFORMATION FOR SEQ ID NO:12:

(i) SEQUENCE CHARACTERISTICS:
        (A) LENGTH: 24 bp (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 12:

ATCGCCGGGT TTGATGAGCG GGTG                                                  24

(2) INFORMATION FOR SEQ ID NO:13:

(i) SEQUENCE CHARACTERISTICS:
        (A) LENGTH: 24
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 13:

CAGACCTCAC ATCCAGGGCT CCCA                                                  24

(2) INFORMATION FOR SEQ ID NO:14:

(i) SEQUENCE CHARACTERISTICS:
        (A) LENGTH: 17 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 14:

GAGACGGATA TTTAATG                                                          17

(2) INFORMATION FOR SEQ ID NO:15:

(i) SEQUENCE CHARACTERISTICS:
        (A) LENGTH: 19 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 15:

GGAGTGCAGA GCTATTCAT                                                                    19

(2) INFORMATION FOR SEQ ID NO:16:

(i) SEQUENCE CHARACTERISTICS:
           (A) LENGTH: 19 bp
           (B) TYPE: nucleic acid
           (C) STRANDEDNESS: double stranded
           (D) TOPOLOGY: linear (ii) MOLECULE TYPE:
           (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 16:

GCAATCGATT TGCTAACAC                                                                    19

(2) INFORMATION FOR SEQ ID NO:17:

(i) SEQUENCE CHARACTERISTICS:
           (A) LENGTH: 18 bp
           (B) TYPE: nucleic acid
           (C) STRANDEDNESS: double stranded
           (D) TOPOLOGY: linear (ii) MOLECULE TYPE:
           (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 17:

GTCCCTAAAG ATGAAGTG                                                                     18

(2) INFORMATION FOR SEQ ID NO:18:

(i) SEQUENCE CHARACTERISTICS:
           (A) LENGTH: 18 bp
           (B) TYPE: nucleic acid
           (C) STRANDEDNESS: double stranded
           (D) TOPOLOGY: linear (ii) MOLECULE TYPE:
           (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 18:

GTCATGAATC CACATGAG                                                              18

(2) INFORMATION FOR SEQ ID NO:19:

(i) SEQUENCE CHARACTERISTICS:
          (A) LENGTH: 18 bp
          (B) TYPE: nucleic acid
          (C) STRANDEDNESS: double stranded
          (D) TOPOLOGY: linear (ii) MOLECULE TYPE:
          (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 19:

TTCTTCCTGC TGCCAAAA                                                              18

(2) INFORMATION FOR SEQ ID NO:20:

(i) SEQUENCE CHARACTERISTICS:
          (A) LENGTH: 18
          (B) TYPE: nucleic acid
          (C) STRANDEDNESS: double-stranded
          (D) TOPOLOGY: linear (ii) MOLECULE TYPE:
          (A) DESCRIPTION: other nucleic acid (iii) HYPOTHETICAL: no (iv) ANTI-SENSE: no (v) FRAGMENT TYPE:

(vi) ORIGINAL SOURCE:

(ix) FEATURE:

(xi) SEQUENCE DESCRIPTION: SEQ ID NO: 20:

CTTTGTTCCT ATCTCACT                                                              18

(2) INFORMATION FOR SEQ ID NO:21:

(i) SEQUENCE CHARACTERISTICS:
          (A) LENGTH: 18 bp
          (B) TYPE: nucleic acid
          (C) STRANDEDNESS: double stranded
          (D) TOPOLOGY: linear (ii) MOLECULE TYPE:
          (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 21:

AGACTTGCTG AGCCTCGA                                                              18

(2) INFORMATION FOR SEQ ID NO:22:

(i) SEQUENCE CHARACTERISTICS:
        (A) LENGTH: 18
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 22:

TTCCTGTTGC AAAAGGAG        18

(2) INFORMATION FOR SEQ ID NO:23:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 23:

TTTGTGATGA TGTCATCC        18

(2) INFORMATION FOR SEQ ID NO:24:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 24:

AGGTAATTTA TCATCTCA        18

(2) INFORMATION FOR SEQ ID NO:25:

(i) SEQUENCE CHARACTERISTICS:
        (A) LENGTH: 18 bp
        (B) TYPE: nucleic acid
        (C) STRANDEDNESS: double stranded (D) TOPOLOGY:  linear (ii) MOLECULE TYPE:
        (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO: 25:

AGGTAATTTA TCAAATTC                                                     18

(2) INFORMATION FOR SEQ ID NO:26:

(i) SEQUENCE CHARACTERISTICS:
        (A) LENGTH:  243 bp
        (B) TYPE:  nucleic acid
        (C) STRANDEDNESS:  double stranded
        (D) TOPOLOGY:  linear (ii) MOLECULE TYPE:
        (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO: 26:

AGTCATTGGG TCCATTTTAG CATCCGGATA TCTGTTTGTC CAGGTTTTTA GAAGTCTCTT         60

AAGGGGAATT TGATAAATTA CCTAAAAATA ATATTAGAGA ATGACTATAT CCACAGCTCA        120

ATGACAAGAC CAACTTATAA AGTGAGCTCC TATAGTAAAG AGAAACTTAA TTCAAATTTC        180

TTGTCCAAAT TAAAAAATTC TGTCTCCTTT TGCAACAGGA ACACAAAGCT ACCATATTAA        240

AAC                                                                    243

(2) INFORMATION FOR SEQ ID NO:27:

(i) SEQUENCE CHARACTERISTICS:
        (A) LENGTH:  248 bp
        (B) TYPE:  nucleic acid
        (C) STRANDEDNESS:  double stranded
        (D) TOPOLOGY:  linear (ii) MOLECULE TYPE:
        (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO: 27:

AGTCATTGGG TCCATTTTAG CATCCGGATA TCTGTTTGTC CAGGTTTTTA GAAGTCTCTT         60

AAGGGGAATT TGAGATGATA AATTACCTAA AAATAATATT AGAGAATGAC TATATCCACA        120

GCTCAATGAC AAGACCAACT TATAAAGTGA GCTCCTATAG TAAAGAGAAA CTTAATTCAA        180

ATTTCTTGTC CAAATTAAAA AATTCTGTCT CCTTTTGCAA CAGGAACACA AAGCTACCAT        240

```
ATTAAAAC                                                                  248

(2) INFORMATION FOR SEQ ID NO:28:

(i) SEQUENCE CHARACTERISTICS:
        (A) LENGTH: 11883 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(xi) SEQUENCE DESCRIPTION: SEQ ID NO: 28:

GTATATGAGC TCCTAGGAGT ATTAGGTGAA GTTCATCCTA GTGAGATGAT AAGTAATTCA           60

GAACAACTGT TCCGGGCTTT TCTGGGTGAA CTTAAGTCCC AGATGACATC AACAGTAAGA          120

GAGCCCAAAC TACCTGTTCT GGCAGGGTGT CTGAAGGGAT TGTCATCACT TATGTGTAAC          180

TTCACTAAGT CCATGGAAGA AGATCCCCAG ACTTCAAGGG AGATTTTTGA TTTTGCGTTA          240

AAGGCAATTC GTCCTCAGAT TGATCTGAAG AGATATGCAG TGCCCTTAGC TGGTTTATGC          300

TTATTTACCC TGCATGCATC TCAATTTAGC ACCTGCCTTT TGGAGAACTA CGTTTCTTTG          360

TTTGAAGTGC TGTCAAAATG GTGTGGCCAT ACAAACATAG AATTGAAAAA AGCCGCACAT          420

TCAGCTCTGG AGTCTTTTCT GAAACAGGTT TCTTTTATGG TGGCAAAAGA TGCAGAAAGG          480

CATAAGAATA AGCTGCAGTA CTTTATGGAG CAATTCTATG GAATCATCAG GAACATGGAT          540

TCAAATAGCA AGGATTTATC AATTGCAATT CGTGGATATG GACTTTTTGC AGGCCCTTGC          600

AAGGTTATAA ACGCAAAAGA TGTTGACTTC ATGTACGTAG AGCTCATTCA GCGCTGCAAG          660

CAGCTGTTCC TCACCCAGAC AGATACTGTT GATGACCATA TTTACCAGAT GCCCAGTTTC          720

CTCCAATCTA TTGTAAGTGT CTTGCTTTAC CTTGATACAA TTCCTGAGGT GTATACTCCG          780

GTTCTGGAAC ATCTCATGGT GGTACAGATA GACAGCTTCC CACAGTATAG TCCAAAAATG          840

CAGCCGGTGT GTTGTAGAGC CATAGTGAAA CTTTTCCTAG CCTTAGCAGA AAAGGGACCA          900

GTTCTCTGGA ATTGCATTAG TACTGTGGTG CATCAAGGTT TAATTAGAAT ATGTTCTAAA          960

CCAGTCGTCT TTCAAAAGGG TGCTGGGTCT GAATCCGAAG ACTATCATAC ATCAGAGGAA         1020

GCTAGAACTG GCAAATGGAA AATGCCCACA TACAAAGACT ATTTGGATCT TTTTAGATAT         1080

CTCCTGAGCT GTGACCAGAT GATGGATTCT CTTTTAGCAG ATGAAGCATT TCTCTTTGTG         1140

AATTCCTCCC TTCATAGTCT GAATCGTTTG CTGTATGATG AATTTGTAAA ATCAGTTTTG         1200

AAGATTGTTG AGAAATTGGA TCTTACACTA GAAAAACAGA ATGTTGGGGA GCAAGAGGAT         1260

GAAACTGAAG CTACTGGTGT TTGGGTGATC CCGACTTCAG ATCCAGCGGC TAACTTGCAC         1320

CCTGCTAAAC CTAAAGATTT TTCAGCTTTC ATTAACCTGG TGGAATTTTG CAGAGAGATT         1380

CTTCCTGAGA AACATGTAGA ATTTTTTGAG CCATGGGTTT ACTCATTTGC GTATGAATTA         1440

ATTTTGCAGT CTACACGGTT ACCACTCATC AGTGTTTTTT ACAAATTGCT TTCTGTTGCT         1500

GTGAGAAATG CCAAGAAAAT GAAGTATTTT GAAGGAGTTG GTCCAAAGAG TCAGAAACAG         1560

TCTCCTGAGG ACCTAGAAAA GTATTCTTGC TTTGCTTTGT TTGCAAAATT TAGTAAAGAG         1620

GTATCAATTA AAATGAAGCA ATACAAAGAT GAACTTTTGG CCTCCTGTTT GACCTTTATT         1680

CTGTCCCTGC CACATGACAT CATTGAACTT GATGTTAGAG CCTACGTTCC TGCATTGCAG         1740
```

-continued

```
ATGGCTTTTA AACTGGGCCT GAGCTATACT CCATTGGCGG AAGTAGGCCT GAATGCTCTA    1800
GAAGAATGGT CAGGTTACAT CTGCAAACAT GTAATTCAGC CCTATTATAA GGACATTCTA    1860
CCCAGCCTTG ATGGATATCT GAAAACTTCA GTCTTATCAG ATGAGACCAA GAATAGCTGG    1920
CAAGTGTCAG CACTTTCTCG GGCTGCCCAG AAAGGATTTA ATAAAGTTGT GCTAAAGCAT    1980
CTGACAAAGA CAAAGAGCAT TTCATCAAAT GAAGCACTGT CCTTAGAAGA AGTGAGGATT    2040
AGAGTAGTAC GGATACTTGG CTCTCTAGGA GGACAAATAA ACAAGAATCT CGTAACAGCT    2100
GCATCATCAG ATGAAATGAT GAAGAAGTGT GTGGCATGGG ACAGAGAAAA AAGACTCCGT    2160
TTTGCAGTAC CATTTATGGA GATGAAGCCT GTCATTTATC TGGATCTATT CCTGCCTCGG    2220
GTCACCGAGT TAGCTCTTTC AGCTAGTGAC AGGCAGACTA CAGTTGCAGC CTGTGAACTT    2280
TTACATAGCA TGGTTATGTT TATGTTGGGA AAAGCCACTC AGATGCCTGA AGATGGTCAG    2340
GGTTCCCCAC CCATGTACCA GCTCTATAAG CGAACTTTTC CTGTTTTACT TCGACTTGCA    2400
TGTGATGTAG ATCAGGTGAC AAGGCAACTG TATGAGCCAC TAGTTATGCA ACTGATTCAC    2460
TGGTTCACTA CAACAAGAA ATTTGAAAGT CAGGACACTG TCGCCTTACT AGAAACGATA    2520
TTGGATGGAA TTGTGGACCC TGTTGACAGT ACTTTGAGAG ATTTTTGTGG TCAGTGTATT    2580
CAAGAATTCC TTAAATGGTC CATTAAGCAG ACGACACCAC AGCAGCAGGA AAAAAGTCCA    2640
GTAAATACCA AATCGCTTTT CAAGCGACTG TATAGCTTTG CACTTCATCC GAATGCCTTC    2700
AAGAGGCTGG GAGCATCACT TGCTTTTAAT AATATCTACA GGGAATTCAG GAAGAAGAG    2760
TCTCTGGTAG AACAGTTTGT GTTTGAAGCC TTGGTAACGT ATATGGAAAG TCTGGCCTTA    2820
GCACATACAG ATGAGAAATC CTTAGGTACA ATTCAACAAT GTTGTGATGC CATTGATCAT    2880
CTCAGTCTTA TCATTGAGAA GAAGCACGTT TCTTTAAACA AAGCAAAAAA ACGACGTTTG    2940
CCACGAGGCT TTCCACCTGC GACATCACTG TGTTTATTGG ATGTGGTCCA GTGGCTTTTA    3000
GCAAATTGTG GGAGACCCCA GACAGAATGT CGACACAAAT CCATAGAACT CTTTTATAAA    3060
TTTGTTACTT TATTGCCAGG CAACAAATCC CCTTTTTTAT GGCTGAAAGA TATTATCAAG    3120
AAAGAAGATA TTTCCTTTCT CATAAACACA TTTGAGGGCG GGGGAAGTGG TCGGCCGTCA    3180
GGCATCCTTG CTCAGCCAAC CCTCTTCCAT TTGCAAGGGC CGTTCAGTCT CAGAGCTGCC    3240
CTGCAGTGGA TGGACATGCT TCTGGCAGCA CTGGAGTGCT ACAACACATT CATTGAAGAG    3300
AAAACTCTGG AAGCACCCAA GGTCCTAGGT ACTGAAACCC AGTCTTCACT TTGGAAAGCG    3360
GTGGCTTTCT TTTTAGAAAG CATTGCTATG CATGATATTA TGGCAGCAGA AAAGTACTTT    3420
GGCACTGGGG CAACAGGTAA CAGACCCAGC CCACAAGAAG GAGAAAGATA TAATTATAGC    3480
AAATGTACAA TTGTGGTCCG CATTATGGAA TTTACCACAA CGCTCCTCAG CACCTCCCCA    3540
GAAGGCTGGA AGCTGCTTGA GAAGGATGTG TGTAACACAA ACCTTATGAA ACTCTTAGTG    3600
AAAACCCTGT GTGAGCCCTC AAGCATAGGT TTCAACATCG GAGATGTCGC AGTTATGAAC    3660
TATCTTCCCA GTGTTTGTAC CAACCTGATG AAAGCACTGA AGAAGTCCCC ATACAAAGAC    3720
ATCCTGGAGA TGCACCTCAA GGAAAAGATA ACAGCACAGA GCATTGAAGA GCTCTGTGCA    3780
GTTGACTTGT ATTGCCCTGA TGCTTGCGTG GACAGGGCCA GGCTGGCTTC TGTCGTGTCA    3840
GCTTGTAAAC AACTTCATAG AGCGGGGGTT TTGTGTGTTA TAATACCATC TCAGTCTGCA    3900
GATCAGCATC ATTCTATTGG CACAAAACTT CTTTCCTTGG TTTATAAAAG CATTGCACCT    3960
GGAGATGAAC AACAGTGCCT TCCTTCACTA GATCCCAATT GTAAGCGATT GGCCAGTGGA    4020
CTTCTGGAGT TGGCCTTTGC TTTTGGAGGA CTGTGTGAGC ACCTTGTGAG TCTTCTCCTG    4080
```

```
GACACGACAG TGTTGTCTAT GCCATCCAGA GGAGGGTCCC AGAAAAACAT CGTCAGCTTC    4140

TCTCATGGAG AGTATTTTTA TAGCTTGTTC TCAGAAACGA TCAACACTGA ATTGTTGAAA    4200

AATCTAGATC TTGCTGTATT GGAGCTCATG AAATCATCTG TGGATAATCC CAAAATGGTG    4260

AGCAATGTTT TGAATGGTAT GTTAGATCAG AGCTTCAGGG ATCGAACCAG TGAGAAACAC    4320

CAAGGACTGA AACTTGCAAC TATAATTCTG CAAAACTGGA AGAAGTGTGA TTCATGGTGG    4380

GCCAAAGATT CTGCTCCTGA AGTAAAATG GCAGTGCTTA CCTTGTTGGC AAAAATTTTC     4440

CAGATTGATT CATCTGTTTG TTTTAATACA AATCACTGCA TGTTCCCTGA AGTCTTTACA    4500

ACATATGTTA GTCTACTTGC TGATTCAAAG TTGGACCTGC ATTTAAAGGG CCAAGCTATA    4560

ATTCTTCTTC CATTCTTCAC CAGTCTTACT GGAGGCAGCC TTGAGGACCT TAAGGTTGTT    4620

CTTGAAAACC TCATCGTTTC TAATTTTCCT ATGAAATCTG AAGAATTTCC CCCAGGAACT    4680

CTGCAGTACA ATAATTATGT GGACTGCATG AAGAAGTTTC TAGATGCATT GGAATTATCT    4740

AAAAGCCCTA TGTTGTTGCA GTTGATGACA GAAATTCTTT GTCGTGAACA GCAACATGTT    4800

ATGGAAGAAT TATTTCAGTC TACTTTCAAA AAGATTGCCA GAAAGAGTTC ATGTATCACA    4860

CAATTAGGCC TTCTGGAAAG TGTATATAGA ATGTTCAGGA GGGATGACCT GCTTTCAAAT    4920

ATCACTCGCC AAGCATTTGT AGACCGTTCT CTGCTCACTC TGTTGTGGCA CTGTAGCTTG    4980

AATGCTTTGA GGGAATTTTT TAGCAAAATT GTGGTGGAAG CCATTAATGT GTTGAAGTCC    5040

AGATTTATAA AGCTGAATGA ATCTGCCTTT GATACTCAAA TCACCAAGAA GATGGGCTAC    5100

TATAAGATGT TAGATGTGAT GTATTCTCGT CTTCCAAAAG ATGATGTTCA CTCTAAGGAA    5160

TCTAAAATTA ATCAAGTTTT CCATGGCTCA TGTATTACAG AAGGAAGTGA ACTTACAAAG    5220

ACACTTATTA AATTGTGCTA TGATGCCTTT ACAGAGAACA TGGCAGGCGA GAACCAGTTG    5280

CTGGAGAGGA AAGACTTTA CCATTGTGCT GCATACAACT GTGCCATTTC TGTTGTCTGC    5340

TGTGTCTTCA ATGAATTAAA ATTTTACCAA GGTTTTCTGT TTACTGAAAA ACCAGAAAAG    5400

AACTTGCTTA TTTTTGAAAA TCTGATAGAC TTGAAGCGCT GCTACACGTT TCCTATAGAA    5460

GTTGAGGTTC CTATGGAGAG AAAGAAAAAG TACCTTGAAA TTAGAAAAGA AGCCAGGGAA    5520

GCAGCAGCAA GTGGGGATTC AGATGGTCCT CGTTATATAT CTTCCTTGTC ATATTTGGCA    5580

GACAGTAGCC TGAGTGAGGA AATGAGTCAA TTTGATTTCT CGACTGGAGT GCAGAGCTAT    5640

TCATATAGTT CCCAAGACCC TAAATCTACC ACTGCTCATT TTCGGAGACA GAAACATAAA    5700

GAGTCCATGA TCCAAGATGA TATCCTGGAG TTAGAGATGG ATGAACTCAA TCAACACGAA    5760

TGTATGGCAA CTATGACTGC TCTGATTAAG CACATGCAGA GAAATCAGAT CCTCCCTAAG    5820

GAAGAAGAGG GTTCAGTGCC AAGAAATCTT CCTCCTTGGA TGAAATTTCT TCATGACAAA    5880

CTAGGAAATC CATCAATATC ATTAAATATC CGTCTCTTCT TAGCCAAGCT TGTTATTAAT    5940

ACAGAAGAAG TCTTTCGTCC TTACGCGAGA TACTGGCTCA GCCCTTTGCT GCAGCTGGTT    6000

GTTTCTGGAA ACAACGGAGG AGAAGGAATT CACTATATGG TGGTTGAGAT AGTGGTTATT    6060

ATTCTTTCAT GGACAGGATT AGCTACTCCT ATAGGTGTCC CTAAAGATGA AGTGTTAGCA    6120

AATCGATTGC TTCATTTCCT AATGAAACAT GTTTTTCATC AAAAAAGAGC TGTGTTTAGA    6180

CACAACCTCG AAATTATAAA AACCCTTGTT GAATGCTGGA AGGATTGTTT ATCCATCCCT    6240

TACAGGTTAA TATTTGAAAA GTTTTCCAGT ACAGATCCTA ATTCTAAAGA CAATTCAGTA    6300

GGAATTCAAT TACTAGGCAT TGTAATGGCC AATAACTTGC CTCCTTATGA CCCAAAATGT    6360

GGCATAGAGA GCATAAAATA CTTTCAAGCT TTGGTCAATA ATATGTCCTT TGTAAGATAT    6420

AGAGAGGTAT ATGCAGCAGC GGCAGAAGTT CTAGGACTTG TTCTTCGATA TATTACTGAG    6480
```

-continued

```
AGAGAAAATA TACTGGAGGA GTCTGTGTGT GAACTGGTCA TAAAACAGTT GAAGCAACAT    6540

CAGAATACGA TGGAGGACAA ATTTATTGTG TGCTTGAACA AAGCTGTGAA GAACTTCCCT    6600

CCTCTTGCTG ATAGGTTTAT GAACACCGTG TTCTTCCTGC TGCCAAAATT TCATGGCGTG    6660

ATGAAGACTC TCTGTCTGGA GGTGGTACTG TGTCGTGCAG AGGAAATAAC AGATCTATAC    6720

TTACAGTTAA AGAGCAAGGA TTTCATTCAA GTCATGAGAC ATAGAGATGA TGAAAGACAA    6780

AAAGTGTGTT TGGACATAAT TTATAAGATG ATGGCAAGAT TGAAACCAGT AGAACTTCGA    6840

GAACTTCTGA ATCCTGTTGT AGAATTCATT TCTCATCCTT CTCCAGTGTG TAGGGAACAA    6900

ATGTATAACA TTCTCATGTG GATTCATGAC AATTATCGAG ATCCAGAAGG TCAGACAGAT    6960

GACGACTCCC AGGAAATATT TAAGTTGGCA AAAGATGTGT TGATTCAAGG ATTGATCGAT    7020

GAGAACCCTG GGCTTCAATT AATTATTCGA AATTTCTGGA GTCATGAAAC TAGGTTACCT    7080

TCAAATACCT TGGATCGATT GTTGGCACTA AATTCCCTAT ATTCTCCTAA GATAGAAGCA    7140

CACTTTTTAA GTTTAGCAAC AGATTTTCTG CTTGAAATGA CCAGCGTGAG CCCAGATTAT    7200

TCAAACCCTA TGTTTGATCA TCCTCTGTCA GAATGCAAAT TTCAGGAATA TACTATTGAT    7260

TCTGACTGGC GTTTCCGAAG TACTGTTCTC ACTCCAATGT TTATTGAGAC TCAGGCCTCC    7320

CAAAGTGCTC TGCAGACCCG GACCCAGGAA GGATCCCTCT CAGCTCGAGG GGTAATGACT    7380

GGGCAGATAC GGGCCACACA ACAGCAGTAT GATTTCACAC CTACGCAAAA TACAGATGGA    7440

AGAAGCTCTT TCAATTGGCT GACTGGGAAC AGCATTGACC CACTGGTGGA TTTTACGGTC    7500

TCCTCCTCAT CTGATTCTTT GTCTTCCTCC TTGCTGTTTG CTCACAAGAG GAGTGAAAAA    7560

TCACAGAGAG GACCCTTGAA GTCAGTAGGA CCTGATTTTG GGAAAAAAAG GCTGGGCCTT    7620

CCAGGGGATG AGGTGGATAA CAAAGCAAAA GGTACAGACA ATCGGGCGGA AATATTAAGA    7680

TTACGGAGAC GATTTTTAAA GGACCGAGAA AAGCTCAGTT TGATTTATGC CAGAAAAGGT    7740

GTTGCTGAAC AAAAACGAGA GAAGGAGATC AAGAGTGAGT TAAAAATGAA GCACGATGCC    7800

CAAGTCATTT TGTACAGAAG TTACCGTCAA GGAGACCTTC CTGACATTCA GATTAAATAC    7860

AGCAGCCTGA TCACTCCCTT GCAAGCTGTG GCCCAGAGAG ACCCAATAAT TGCAAAGCAG    7920

CTCTTTGGCA GCTTGTTTTC TGGAATTATA AAAGAGATGG ATAAATATAA GACCATGTCT    7980

GAAAAAAACA ACATTACTCA GAAGTTGCTC CAGGACTTCA ATAATTTTCT TAACACCACT    8040

GTCTCTTTCT TTCCACCTTT CATCTCCTGT ATCCAGGAAA TTAGTTGCCA ACACGCAGAC    8100

TTGCTGAGCC TCGACCCAGC TTCTGTCAGT GCCAGCTGCC TGGCCAGTCT GCAGCAGCCT    8160

GTAGGCGTCC GCCTTCTGGA GGAGGCCTTG CTCCACCTGC TGCCTGAAGA GCCACCTGCC    8220

AAGCGAGTTC GAGGGAGACC CTGTCTCTAC CCTGATTTTG TCAGATGGAT GGAACTTGCT    8280

AAACTGTATA GATCAATTGG AGAATATGAC ATCCTCCGTG GGATTTTTAA TAGTGAGATA    8340

GGAACAAAGC AAGTCACTCA GAATGCATTA TTAGCAGAAG CAAGAAATGA TTATTCTGAA    8400

GCCGTTAAGC AGTATAATGA GGCTCTCAAT AAACAAGACT GGGTAGATGG TGAGCCTATG    8460

GAAGCTGAGA AGGATTTTTG GAACTTGCA TCCCTTGACT GTTATAACCA ACTTGCTGAG    8520

TGGAAATCAC TGGCATACTG TTCTACAGTC AGTGTTGACA GTGCGAACCC TCCAGATTTA    8580

AATAAAATGT GGAATGAACC ATTTTATCAG GAGACCTATC TACCTTACAT GATCCGCAGC    8640

AAGCTGAAGC TACTTCTGCA AGGTGAGGGA GACCAGTCCC TGCTGACATT TATTGATGAA    8700

GCTGTGAGCA AGGAGCTCCA GAAGGTCCTC GTAGAGCTTC ATTACAGTCA GGAATTGAGT    8760

CTCCTTTATA TCCTACAAGA TGACGTCGAC AGAGCCAAAT ATTATATTGA AAATTGCATT    8820
```

```
CGGATTTTCA TGCAGAGCTA TTCTAGTATT GATGTCCTTT TAGAGAGAAG TAGACTCACC    8880
AAATTGCAAT CTCTACAGGC TTTAATAGAA ATTCAGGAGT TCATCAGCTT TATAAGGAAA    8940
CAAGGTAATT TATCATCTCA AATTCCCCTT AAGAGACTTC TAAAAACCTG ACAAACAGA     9000
TATCCGGATG CTAAAATGGA CCCAATGAAC ATCTGGATG ACATCATCAC AAATCGATGT     9060
TTCTTTCTCA GCAAAATAGA AGAAAAACTG ACTATTCCTC CAGATGATCA TAGTATGAAC    9120
ACAGATGGAG ATGAAGATTC CAGTGACAGA ATGAAAGTGC AGGAGCAGGA GGAAGATATT    9180
TATTCTCTGA TTAAGAGTGG TAAGTTTTCC ATGAAAATGA AGATGATAGA AAGTGCAAGG    9240
AAACAGAAAA ATTTCTCACT AGCCATGAAA CTATTAAAGG AGCTTCATAA AGAGTCAAAA    9300
ACAAGAGATG ACTGGCTGGT GAAATGGGTG CAGAGCTACT GTCGACTCAG TCACAGCCGG    9360
AGCCAGACCC AGAATCGTCC TGAGCAGATC CTTACTGTGT TGAAAACAGT CTCTTTGTTG    9420
GATGAGAACA CATCAAGCTA CTTAAGCAAA AATATTCCAG TTTCCCGTGA CCACAACATT    9480
CTCTTGGGTA CAACTTACAG GATCATAGCT AATGCTCTCA GCAGTGATCC AACTTGCCTT    9540
GCTGAAATCG GGGAAAGCAA GGCTAGAAGA ATCTTGGAGC TGTCTGGATC CAGTTTAGAG    9600
AATGCAGAAG AGGTGATCGC AGGTCTATAC CAGAGAGTGT TGCATCACCT TTCTGAGGCC    9660
GTGCGGATTG CAGAGGAGGA GGCCCAGCCT TTCACTAGAG GCCAGGAACC TGCAGTTGGG    9720
GTGATAGATG CTTACATGAC ACTGGTGGAT TTCTGTGACC AGCAGCTCCG CAAGGAGGAA    9780
GAGAGTTCAT CAGTTACTGA GTCTGTACAA CTGCAGATGT ATCCAGCCCT TGTGGTGGAC    9840
AAAATGTTAA AAGCTTTAAG ACTCGATTCC AATGAAGCCA GGCTGAAGTT TCCCAGACTA    9900
CTGCAGATTA TAGAACGGTA TCCAGAGGAG ACCCTGAGCC TAATGACCAA AGAGATTTCT    9960
TCCATTCCTT GCTGGCAGTT CATTGGCTGG ATCAGCCACA TGGTGGCCTT ACTGGACAAA   10020
GAGGAAGCTG TCGCTGTCCA TCGCACAGTG GAAGAGATTG CTGATAACTA TCCACAGGCG   10080
ATGGTCTACC CATTTATAAT AAGCAGTGAA AGCTATTCCT TCAAAGATAC TTCTACTGGT   10140
TATAAGAATA AGGAGTTTGT GGAAAGGATT AAAATTAAGT TGGATCAAGG AGGAGTGATT   10200
CAAGATTTTA TTAATGCCCT AGAACAGCTC TCTCATCCTG AAATGCTCTT TAAGGACTGG   10260
ACTGATGATA TCAAAGTTGA ACTTGAAAAA AACCCTGTAA ATAGAAAAAA CATTGAAAAG   10320
ATGTATGAAA AAATGTATGC AACCTTGGGA GACCCACAGG CTCCAGGTCT TGGGGCTTTT   10380
CGAAGAAGGT GTATTCAGGG TTTTGGAAAA GAATTTGATA AACACTTTGG GAGAGGAGGT   10440
TCTAAGCTAC CTGGAATGAA ATCCCGTGAA TTCAGTGATA TTACCAACTC ACTATTTTCA   10500
AAAATGTGCG AAGTCTCAAA GCCACCTGGG AATCTGAAAG AATGCTCGCC CTGGATGAGT   10560
GACTTCAAAG TAGAATTTTT GAGAAGTGAA CTGGAGATTC CTGGTCAGTA TGATGGCAAG   10620
GGAAAACCAG TGCCAGAATA CCATGCACGA ATTGCTGGGT TTGATGAGCG GATAAAAGTA   10680
ATGGCTTCTA TGAGAAAACC AAAGCGTATC ATCATCCGAG GCCATGATGA GAGAGAGTAC   10740
CCTTTCCTTG TGAAGGGAGG TGAAGATCTG AGGCAGGACC AACGCATCGA GCAGCTCTTC   10800
GAGGTCATGA ATGTCATCCT TTCCCAAGAT GCTACCTGTA GTCAGAGAAG CATGCAGCTA   10860
AAGACATACC AGGTCATACC CATGACCTCC AGATTAGGAC TAATTGAATG GATTGAAAAT   10920
ACTTTTACCT TGAAGGAACT TCTTTTGAGT AACATGTCAC AAGAGGAGAA AGCGGCTTGT   10980
ACAAGAGATC CCAAAGCACC ACCATTTGAA TATAGAGACT GGCTGACAAA GATGTCTGGG   11040
AAATGTGATG TTGGTGCTTA CATGCTAATG TATAAGGGAG CTAGTCGTAC TGAAACAGTC   11100
ACATCTTTTA GAAAAAGAGA AAGTAAGGTG CCAGCCGATC TCTTAAAGCG GGCCTTTGTG   11160
AAGATGAGTA CCAGCCCTGA GGCCTTCCTG ACACTCCGCT CACACTTTGC CGGCTCTCAC   11220
```

```
GCTTTGATAT GCATTAGTCA CTGGATTCCT GGGATTGGAG ATAGACATCT GAACAATTTC    11280

CTGGTAAGCA TGGAGACAGG TGGAGTGATT GGAATCGACT TTGGACATGC ATTTGGATCA    11340

GCTACTCAGT TTCTGCCGGT CCCTGAGTTG ATGCCTTTTC GTCTAACTCG CCAGTTTATC    11400

AATCTGATGT TACCAATGAA AGAAACAGGT GTTATGTACA GTATCATGGT GCATGCACTG    11460

AGAGCCTTCC GCTCGCAGTC CAACCTGCTT GCTAACACCA TGGACGTGTT TGTAAAGGAG    11520

CCTTCCTTCG ACTGGAAAAA TTTTGAACAG AAAATGCGGA AAAAGGAGG ATCATGGATT    11580

CAAGAAATAA ATGTAACTGA AAAAAATTGG TATCCCCGGC AGAAAATACA TTATGCTAAG    11640

AGAAAGTTAG CTGGTGCCAA TCCAGCAGTT ATTACTTGTG ATGAGTTACT TCTGGGCCAT    11700

GAGAAGGCAG CTGCATTTGG AGATTATGTG GCTGTAGCAC GAGGAAGTGA AGATCACAAT    11760

ATCCGTGCCC AAGAACTGGA GAGTGACCTT TCAGAAGAAG CTCAGGTGAA GTGCTTGATT    11820

GACCAGGCAA CAGACCCCAA CATCCTTGGC AGAACCTTGG TAGGATGGGA GCCCTGGATG    11880

TGA                                                                 11883
```

(2) INFORMATION FOR SEQ ID NO: 29:

(i) SEQUENCE CHARACTERISTICS:
        (A) LENGTH: 2987 amino acids
        (B) TYPE: amino acid
        (C) STRANDEDNESS:
        (D) TOPOLOGY: linear (ii) MOLECULE TYPE: protein (iii) HYPOTHETICAL: no (iv) ANTI-SENSE: no (vi) ORIGINAL SOURCE:

(ix) FEATURE:

(v) SEQUENCE DESCRIPTION: SEQ ID NO: 29:

```
Val Tyr Glu Leu Leu Gly Val Leu Gly Glu Val His Pro Ser Glu
                 5                  10                  15

Met Ile Ser Asn Ser Glu Gln Leu Phe Arg Ala Phe Leu Gly Glu
                20                  25                  30

Leu Lys Ser Gln Met Thr Ser Thr Val Arg Glu Pro Lys Leu Pro
                35                  40                  45

Val Leu Ala Gly Cys Leu Lys Gly Leu Ser Ser Leu Met Cys Asn
                50                  55                  60

Phe Thr Lys Ser Met Glu Glu Asp Pro Gln Thr Ser Arg Glu Ile
                65                  70                  75

Phe Asp Phe Ala Leu Lys Ala Ile Arg Pro Gln Ile Asp Leu Lys
                80                  85                  90

Arg Tyr Ala Val Pro Leu Ala Gly Leu Cys Leu Phe Thr Leu His
                95                 100                 105

Ala Ser Gln Phe Ser Thr Cys Leu Leu Glu Asn Tyr Val Ser Leu
               110                 115                 120

Phe Glu Val Leu Ser Lys Trp Cys Gly His Thr Asn Ile Glu Leu
               125                 130                 135

Lys Lys Ala Ala His Ser Ala Leu Glu Ser Phe Leu Lys Gln Val
               140                 145                 150

Ser Phe Met Val Ala Lys Asp Ala Glu Arg His Lys Asn Lys Leu
               155                 160                 165
```

-continued

```
Gln Tyr Phe Met Glu Gln Phe Tyr Gly Ile Ile Arg Asn Met Asp
                170                 175                 180

Ser Asn Ser Lys Asp Leu Ser Ile Ala Ile Arg Gly Tyr Gly Leu
            185                 190                 195

Phe Ala Gly Pro Cys Lys Val Ile Asn Ala Lys Asp Val Asp Phe
            200                 205                 210

Met Tyr Val Glu Leu Ile Gln Arg Cys Lys Gln Leu Phe Leu Thr
            215                 220                 225

Gln Thr Asp Thr Val Asp Asp His Ile Tyr Gln Met Pro Ser Phe
            230                 235                 240

Leu Gln Ser Ile Val Ser Val Leu Leu Tyr Leu Asp Thr Ile Pro
            245                 250                 255

Glu Val Tyr Thr Pro Val Leu Glu His Leu Met Val Val Gln Ile
            260                 265                 270

Asp Ser Phe Pro Gln Tyr Ser Pro Lys Met Gln Pro Val Cys Cys
            275                 280                 285

Arg Ala Ile Val Lys Leu Phe Leu Ala Leu Ala Glu Lys Gly Pro
            290                 295                 300

Val Leu Trp Asn Cys Ile Ser Thr Val Val His Gln Gly Leu Ile
            305                 310                 315

Arg Ile Cys Ser Lys Pro Val Val Phe Gln Lys Gly Ala Gly Ser
            320                 325                 330

Glu Ser Glu Asp Tyr His Thr Ser Glu Glu Ala Arg Thr Gly Lys
            335                 340                 345

Trp Lys Met Pro Thr Tyr Lys Asp Tyr Leu Asp Leu Phe Arg Tyr
            350                 355                 360

Leu Leu Ser Cys Asp Gln Met Met Asp Ser Leu Leu Ala Asp Glu
            365                 370                 375

Ala Phe Leu Phe Val Asn Ser Ser Leu His Ser Leu Asn Arg Leu
            380                 385                 390

Leu Tyr Asp Glu Phe Val Lys Ser Val Leu Lys Ile Val Glu Lys
            395                 400                 405

Leu Asp Leu Thr Leu Glu Lys Gln Asn Val Gly Glu Gln Glu Asp
            410                 415                 420

Glu Thr Glu Ala Thr Gly Val Trp Val Ile Pro Thr Ser Asp Pro
            425                 430                 435

Ala Ala Asn Leu His Pro Ala Lys Pro Lys Asp Phe Ser Ala Phe
            440                 445                 450

Ile Asn Leu Val Glu Phe Cys Arg Glu Ile Leu Pro Glu Lys His
            455                 460                 465

Val Glu Phe Phe Glu Pro Trp Val Tyr Ser Phe Ala Tyr Glu Leu
            470                 475                 480

Ile Leu Gln Ser Thr Arg Leu Pro Leu Ile Ser Val Phe Tyr Lys
            485                 490                 495

Leu Leu Ser Val Ala Val Arg Asn Ala Lys Lys Met Lys Tyr Phe
            500                 505                 510

Glu Gly Val Gly Pro Lys Ser Gln Lys Gln Ser Pro Glu Asp Leu
            515                 520                 525

Glu Lys Tyr Ser Cys Phe Ala Leu Phe Ala Lys Phe Ser Lys Glu
            530                 535                 540

Val Ser Ile Lys Met Lys Gln Tyr Lys Asp Glu Leu Leu Ala Ser
            545                 550                 555

Cys Leu Thr Phe Ile Leu Ser Leu Pro His Asp Ile Ile Glu Leu
```

-continued

```
              560                 565                 570
Asp Val Arg Ala Tyr Val Pro Ala Leu Gln Met Ala Phe Lys Leu
              575                 580                 585
Gly Leu Ser Tyr Thr Pro Leu Ala Glu Val Gly Leu Asn Ala Leu
              590                 595                 600
Glu Glu Trp Ser Gly Tyr Ile Cys Lys His Val Ile Gln Pro Tyr
              605                 610                 615
Tyr Lys Asp Ile Leu Pro Ser Leu Asp Gly Tyr Leu Lys Thr Ser
              620                 625                 630
Val Leu Ser Asp Glu Thr Lys Asn Ser Trp Gln Val Ser Ala Leu
              635                 640                 645
Ser Arg Ala Ala Gln Lys Gly Phe Asn Lys Val Val Leu Lys His
              650                 655                 660
Leu Thr Lys Thr Lys Ser Ile Ser Ser Asn Glu Ala Leu Ser Leu
              665                 670                 675
Glu Glu Val Arg Ile Arg Val Val Arg Ile Leu Gly Ser Leu Gly
              680                 685                 690
Gly Gln Ile Asn Lys Asn Leu Val Thr Ala Ala Ser Ser Asp Glu
              695                 700                 705
Met Met Lys Lys Cys Val Ala Trp Asp Arg Glu Lys Arg Leu Arg
              710                 715                 720
Phe Ala Val Pro Phe Met Glu Met Lys Pro Val Ile Tyr Leu Asp
              725                 730                 735
Leu Phe Leu Pro Arg Val Thr Glu Leu Ala Leu Ser Ala Ser Asp
              740                 745                 750
Arg Gln Thr Thr Val Ala Ala Cys Glu Leu Leu His Ser Met Val
              755                 760                 765
Met Phe Met Leu Gly Lys Ala Thr Gln Met Pro Glu Asp Gly Gln
              770                 775                 780
Gly Ser Pro Pro Met Tyr Gln Leu Tyr Lys Arg Thr Phe Pro Val
              785                 790                 795
Leu Leu Arg Leu Ala Cys Asp Val Asp Gln Val Thr Arg Gln Leu
              800                 805                 810
Tyr Glu Pro Leu Val Met Gln Leu Ile His Trp Phe Thr Asn Asn
              815                 820                 825
Lys Lys Phe Glu Ser Gln Asp Thr Val Ala Leu Leu Glu Thr Ile
              830                 835                 840
Leu Asp Gly Ile Val Asp Pro Val Asp Ser Thr Leu Arg Asp Phe
              845                 850                 855
Cys Gly Gln Cys Ile Gln Glu Phe Leu Lys Trp Ser Ile Lys Gln
              860                 865                 870
Thr Thr Pro Gln Gln Gln Glu Lys Ser Pro Val Asn Thr Lys Ser
              875                 880                 885
Leu Phe Lys Arg Leu Tyr Ser Phe Ala Leu His Pro Asn Ala Phe
              890                 895                 900
Lys Arg Leu Gly Ala Ser Leu Ala Phe Asn Asn Ile Tyr Arg Glu
              905                 910                 915
Phe Arg Glu Glu Glu Ser Leu Val Glu Gln Phe Val Phe Glu Ala
              920                 925                 930
Leu Val Thr Tyr Met Glu Ser Leu Ala Leu Ala His Thr Asp Glu
              935                 940                 945
Lys Ser Leu Gly Thr Ile Gln Gln Cys Cys Asp Ala Ile Asp His
              950                 955                 960
```

```
Leu Ser Leu Ile Ile Glu Lys Lys His Val Ser Leu Asn Lys Ala
            965                 970                 975

Lys Lys Arg Arg Leu Pro Arg Gly Phe Pro Pro Ala Thr Ser Leu
            980                 985                 990

Cys Leu Leu Asp Val Val Gln Trp Leu Leu Ala Asn Cys Gly Arg
            995                1000                1005

Pro Gln Thr Glu Cys Arg His Lys Ser Ile Glu Leu Phe Tyr Lys
           1010                1015                1020

Phe Val Thr Leu Leu Pro Gly Asn Lys Ser Pro Phe Leu Trp Leu
           1025                1030                1035

Lys Asp Ile Ile Lys Lys Glu Asp Ile Ser Phe Leu Ile Asn Thr
           1040                1045                1050

Phe Glu Gly Gly Gly Ser Gly Arg Pro Ser Gly Ile Leu Ala Gln
           1055                1060                1065

Pro Thr Leu Phe His Leu Gln Gly Pro Phe Ser Leu Arg Ala Ala
           1070                1075                1080

Leu Gln Trp Met Asp Met Leu Leu Ala Ala Leu Glu Cys Tyr Asn
           1085                1090                1095

Thr Phe Ile Glu Glu Lys Thr Leu Glu Ala Pro Lys Val Leu Gly
           1100                1105                1110

Thr Glu Thr Gln Ser Ser Leu Trp Lys Ala Val Ala Phe Phe Leu
           1115                1120                1125

Glu Ser Ile Ala Met His Asp Ile Met Ala Ala Glu Lys Tyr Phe
           1130                1135                1140

Gly Thr Gly Ala Thr Gly Asn Arg Pro Ser Pro Gln Glu Gly Glu
           1145                1150                1155

Arg Tyr Asn Tyr Ser Lys Cys Thr Ile Val Val Arg Ile Met Glu
           1160                1165                1170

Phe Thr Thr Thr Leu Leu Ser Thr Ser Pro Glu Gly Trp Lys Leu
           1175                1180                1185

Leu Glu Lys Asp Val Cys Asn Thr Asn Leu Met Lys Leu Leu Val
           1190                1195                1200

Lys Thr Leu Cys Glu Pro Ser Ser Ile Gly Phe Asn Ile Gly Asp
           1205                1210                1215

Val Ala Val Met Asn Tyr Leu Pro Ser Val Cys Thr Asn Leu Met
           1220                1225                1230

Lys Ala Leu Lys Lys Ser Pro Tyr Lys Asp Ile Leu Glu Met His
           1235                1240                1245

Leu Lys Glu Lys Ile Thr Ala Gln Ser Ile Glu Glu Leu Cys Ala
           1250                1255                1260

Val Asp Leu Tyr Cys Pro Asp Ala Cys Val Asp Arg Ala Arg Leu
           1265                1270                1275

Ala Ser Val Val Ser Ala Cys Lys Gln Leu His Arg Ala Gly Val
           1280                1285                1290

Leu Cys Val Ile Ile Pro Ser Gln Ser Ala Asp Gln His His Ser
           1295                1300                1305

Ile Gly Thr Lys Leu Leu Ser Leu Val Tyr Lys Ser Ile Ala Pro
           1310                1315                1320

Gly Asp Glu Gln Gln Cys Leu Pro Ser Leu Asp Pro Asn Cys Lys
           1325                1330                1335

Arg Leu Ala Ser Gly Leu Leu Glu Leu Ala Phe Ala Phe Gly Gly
           1340                1345                1350
```

```
Leu Cys Glu His Leu Val Ser Leu Leu Asp Thr Thr Val Leu
            1355                1360                1365

Ser Met Pro Ser Arg Gly Gly Ser Gln Lys Asn Ile Val Ser Phe
            1370                1375                1380

Ser His Gly Glu Tyr Phe Tyr Ser Leu Phe Ser Glu Thr Ile Asn
            1385                1390                1395

Thr Glu Leu Leu Lys Asn Leu Asp Leu Ala Val Leu Glu Leu Met
            1400                1405                1410

Lys Ser Ser Val Asp Asn Pro Lys Met Val Ser Asn Val Leu Asn
            1415                1420                1425

Gly Met Leu Asp Gln Ser Phe Arg Asp Arg Thr Ser Glu Lys His
            1430                1435                1440

Gln Gly Leu Lys Leu Ala Thr Ile Ile Leu Gln Asn Trp Lys Lys
            1445                1450                1455

Cys Asp Ser Trp Trp Ala Lys Asp Ser Ala Pro Glu Ser Lys Met
            1460                1465                1470

Ala Val Leu Thr Leu Leu Ala Lys Ile Phe Gln Ile Asp Ser Ser
            1475                1480                1485

Val Cys Phe Asn Thr Asn His Cys Met Phe Pro Glu Val Phe Thr
            1490                1495                1500

Thr Tyr Val Ser Leu Leu Ala Asp Ser Lys Leu Asp Leu His Leu
            1505                1510                1515

Lys Gly Gln Ala Ile Ile Leu Leu Pro Phe Phe Thr Ser Leu Thr
            1520                1525                1530

Gly Gly Ser Leu Glu Asp Leu Lys Val Val Leu Glu Asn Leu Ile
            1535                1540                1545

Val Ser Asn Phe Pro Met Lys Ser Glu Glu Phe Pro Pro Gly Thr
            1550                1555                1560

Leu Gln Tyr Asn Asn Tyr Val Asp Cys Met Lys Lys Phe Leu Asp
            1565                1570                1575

Ala Leu Glu Leu Ser Lys Ser Pro Met Leu Leu Gln Leu Met Thr
            1580                1585                1590

Glu Ile Leu Cys Arg Glu Gln Gln His Val Met Glu Glu Leu Phe
            1595                1600                1605

Gln Ser Thr Phe Lys Lys Ile Ala Arg Lys Ser Ser Cys Ile Thr
            1610                1615                1620

Gln Leu Gly Leu Leu Glu Ser Val Tyr Arg Met Phe Arg Arg Asp
            1625                1630                1635

Asp Leu Leu Ser Asn Ile Thr Arg Gln Ala Phe Val Asp Arg Ser
            1640                1645                1650

Leu Leu Thr Leu Leu Trp His Cys Ser Leu Asn Ala Leu Arg Glu
            1655                1660                1665

Phe Phe Ser Lys Ile Val Val Glu Ala Ile Asn Val Leu Lys Ser
            1670                1675                1680

Arg Phe Ile Lys Leu Asn Glu Ser Ala Phe Asp Thr Gln Ile Thr
            1685                1690                1695

Lys Lys Met Gly Tyr Tyr Lys Met Leu Asp Val Met Tyr Ser Arg
            1700                1705                1710

Leu Pro Lys Asp Asp Val His Ser Lys Glu Ser Lys Ile Asn Gln
            1715                1720                1725

Val Phe His Gly Ser Cys Ile Thr Glu Gly Ser Glu Leu Thr Lys
            1730                1735                1740

Thr Leu Ile Lys Leu Cys Tyr Asp Ala Phe Thr Glu Asn Met Ala
```

-continued

```
                  1745                1750                1755

Gly Glu Asn Gln Leu Leu Glu Arg Arg Arg Leu Tyr His Cys Ala
              1760                1765                1770

Ala Tyr Asn Cys Ala Ile Ser Val Val Cys Cys Val Phe Asn Glu
              1775                1780                1785

Leu Lys Phe Tyr Gln Gly Phe Leu Phe Thr Glu Lys Pro Glu Lys
              1790                1795                1800

Asn Leu Leu Ile Phe Glu Asn Leu Ile Asp Leu Lys Arg Cys Tyr
              1805                1810                1815

Thr Phe Pro Ile Glu Val Glu Val Pro Met Glu Arg Lys Lys Lys
              1820                1825                1830

Tyr Leu Glu Ile Arg Lys Glu Ala Arg Glu Ala Ala Ala Ser Gly
              1835                1840                1845

Asp Ser Asp Gly Pro Arg Tyr Ile Ser Ser Leu Ser Tyr Leu Ala
              1850                1855                1860

Asp Ser Ser Leu Ser Glu Glu Met Ser Gln Phe Asp Phe Ser Thr
              1865                1870                1875

Gly Val Gln Ser Tyr Ser Tyr Ser Ser Gln Asp Pro Lys Ser Thr
              1880                1885                1890

Thr Ala His Phe Arg Arg Gln Lys His Lys Glu Ser Met Ile Gln
              1895                1900                1905

Asp Asp Ile Leu Glu Leu Glu Met Asp Glu Leu Asn Gln His Glu
              1910                1915                1920

Cys Met Ala Thr Met Thr Ala Leu Ile Lys His Met Gln Arg Asn
              1925                1930                1935

Gln Ile Leu Pro Lys Glu Glu Gly Ser Val Pro Arg Asn Leu
              1940                1945                1950

Pro Pro Trp Met Lys Phe Leu His Asp Lys Leu Gly Asn Pro Ser
              1955                1960                1965

Ile Ser Leu Asn Ile Arg Leu Phe Leu Ala Lys Leu Val Ile Asn
              1970                1975                1980

Thr Glu Glu Val Phe Arg Pro Tyr Ala Arg Tyr Trp Leu Ser Pro
              1985                1990                1995

Leu Leu Gln Leu Val Val Ser Gly Asn Asn Gly Gly Glu Gly Ile
              2000                2005                2010

His Tyr Met Val Val Glu Ile Val Val Ile Ile Leu Ser Trp Thr
              2015                2020                2025

Gly Leu Ala Thr Pro Ile Gly Val Pro Lys Asp Glu Val Leu Ala
              2030                2035                2040

Asn Arg Leu Leu His Phe Leu Met His Val Phe His Gln Lys Arg
              2045                2050                2055

Ala Val Phe Arg His Asn Leu Glu Ile Ile Lys Thr Leu Val Glu
              2060                2065                2070

Cys Trp Lys Asp Cys Leu Ser Ile Pro Tyr Arg Leu Ile Phe Glu
              2075                2080                2085

Lys Phe Ser Ser Thr Asp Pro Asn Ser Lys Asp Asn Ser Val Gly
              2090                2095                2100

Ile Gln Leu Leu Gly Ile Val Met Ala Asn Asn Leu Pro Pro Tyr
              2105                2110                2115

Asp Pro Lys Cys Gly Ile Glu Ser Ile Lys Tyr Phe Gln Ala Leu
              2120                2125                2130

Val Asn Asn Met Ser Phe Val Arg Tyr Arg Glu Val Tyr Ala Ala
              2135                2140                2145
```

-continued

```
Ala Ala Glu Val Leu Gly Leu Val Leu Arg Tyr Ile Thr Glu Arg
            2150                2155                2160
Glu Asn Ile Leu Glu Glu Ser Val Cys Glu Leu Val Ile Lys Gln
            2165                2170                2175
Leu Lys Gln His Gln Asn Thr Met Glu Asp Lys Phe Ile Val Cys
            2180                2185                2190
Leu Asn Lys Ala Val Lys Asn Phe Pro Pro Leu Ala Asp Arg Phe
            2195                2200                2205
Met Asn Thr Val Phe Phe Leu Leu Pro Lys Phe His Gly Val Met
            2210                2215                2220
Lys Thr Leu Cys Leu Glu Val Val Leu Cys Arg Ala Glu Glu Ile
            2225                2230                2235
Thr Asp Leu Tyr Leu Gln Leu Lys Ser Lys Asp Phe Ile Gln Val
            2240                2245                2250
Met Arg His Arg Asp Asp Glu Arg Gln Lys Val Cys Leu Asp Ile
            2255                2260                2265
Ile Tyr Lys Met Met Ala Arg Leu Lys Pro Val Glu Leu Arg Glu
            2270                2275                2280
Leu Leu Asn Pro Val Val Glu Phe Ile Ser His Pro Ser Pro Val
            2285                2290                2295
Cys Arg Glu Gln Met Tyr Asn Ile Leu Met Trp Ile His Asp Asn
            2300                2305                2310
Tyr Arg Asp Pro Glu Gly Gln Thr Asp Asp Ser Gln Glu Ile
            2315                2320                2325
Phe Lys Leu Ala Lys Asp Val Leu Ile Gln Gly Leu Ile Asp Glu
            2330                2335                2340
Asn Pro Gly Leu Gln Leu Ile Ile Arg Asn Phe Trp Ser His Glu
            2345                2350                2355
Thr Arg Leu Pro Ser Asn Thr Leu Asp Arg Leu Leu Ala Leu Asn
            2360                2365                2370
Ser Leu Tyr Ser Pro Lys Ile Glu Ala His Phe Leu Ser Leu Ala
            2375                2380                2385
Thr Asp Phe Leu Leu Glu Met Thr Ser Val Ser Pro Asp Tyr Ser
            2390                2395                2400
Asn Pro Met Phe Asp His Pro Leu Ser Glu Cys Lys Phe Gln Glu
            2405                2410                2415
Tyr Thr Ile Asp Ser Asp Trp Arg Phe Arg Ser Thr Val Leu Thr
            2420                2425                2430
Pro Met Phe Ile Glu Thr Gln Ala Ser Gln Ser Ala Leu Gln Thr
            2435                2440                2445
Arg Thr Gln Glu Gly Ser Leu Ser Ala Arg Gly Val Met Thr Gly
            2450                2455                2460
Gln Ile Arg Ala Thr Gln Gln Tyr Asp Phe Thr Pro Thr Gln
            2465                2470                2475
Asn Thr Asp Gly Arg Ser Ser Phe Asn Trp Leu Thr Gly Asn Ser
            2480                2485                2490
Ile Asp Pro Leu Val Asp Phe Thr Val Ser Ser Ser Asp Ser
            2495                2500                2505
Leu Ser Ser Ser Leu Leu Phe Ala His Lys Arg Ser Glu Lys Ser
            2510                2515                2520
Gln Arg Gly Pro Leu Lys Ser Val Gly Pro Asp Phe Gly Lys Lys
            2525                2530                2535
```

-continued

```
Arg Leu Gly Leu Pro Gly Asp Glu Val Asp Asn Lys Ala Lys Gly
            2540                2545                2550

Thr Asp Asn Arg Ala Glu Ile Leu Arg Leu Arg Arg Phe Leu
        2555                2560                2565

Lys Asp Arg Glu Lys Leu Ser Leu Ile Tyr Ala Arg Lys Gly Val
            2570                2575                2580

Ala Glu Gln Lys Arg Glu Lys Glu Ile Lys Ser Glu Leu Lys Met
            2585                2590                2595

Lys His Asp Ala Gln Val Ile Leu Tyr Arg Ser Tyr Arg Gln Gly
            2600                2605                2610

Asp Leu Pro Asp Ile Gln Ile Lys Tyr Ser Ser Leu Ile Thr Pro
            2615                2620                2625

Leu Gln Ala Val Ala Gln Arg Asp Pro Ile Ile Ala Lys Gln Leu
            2630                2635                2640

Phe Gly Ser Leu Phe Ser Gly Ile Ile Lys Glu Met Asp Lys Tyr
            2645                2650                2655

Lys Thr Met Ser Glu Lys Asn Asn Ile Thr Gln Lys Leu Leu Gln
            2660                2665                2670

Asp Phe Asn Asn Phe Leu Asn Thr Thr Val Ser Phe Pro Pro
            2675                2680                2685

Phe Ile Ser Cys Ile Gln Glu Ile Ser Cys Gln His Ala Asp Leu
            2690                2695                2700

Leu Ser Leu Asp Pro Ala Ser Val Ser Ala Ser Cys Leu Ala Ser
            2705                2710                2715

Leu Gln Gln Pro Val Gly Val Arg Leu Leu Glu Glu Ala Leu Leu
            2720                2725                2730

His Leu Leu Pro Glu Glu Pro Pro Ala Lys Arg Val Arg Gly Arg
            2735                2740                2745

Pro Cys Leu Tyr Pro Asp Phe Val Arg Trp Met Glu Leu Ala Lys
            2750                2755                2760

Leu Tyr Arg Ser Ile Gly Glu Tyr Asp Ile Leu Arg Gly Ile Phe
            2765                2770                2775

Asn Ser Glu Ile Gly Thr Lys Gln Val Thr Gln Asn Ala Leu Leu
            2780                2785                2790

Ala Glu Ala Arg Asn Asp Tyr Ser Glu Ala Val Lys Gln Tyr Asn
            2795                2800                2805

Glu Ala Leu Asn Lys Gln Asp Trp Val Asp Gly Glu Pro Met Glu
            2810                2815                2820

Ala Glu Lys Asp Phe Trp Glu Leu Ala Ser Leu Asp Cys Tyr Asn
            2825                2830                2835

Gln Leu Ala Glu Trp Lys Ser Leu Ala Tyr Cys Ser Thr Val Ser
            2840                2845                2850

Val Asp Ser Ala Asn Pro Pro Asp Leu Asn Lys Met Trp Asn Glu
            2855                2860                2865

Pro Phe Tyr Gln Glu Thr Tyr Leu Pro Tyr Met Ile Arg Ser Lys
            2870                2875                2880

Leu Lys Leu Leu Leu Gln Gly Glu Gly Asp Gln Ser Leu Leu Thr
            2885                2890                2895

Phe Ile Asp Glu Ala Val Ser Lys Glu Leu Gln Lys Val Leu Val
            2900                2905                2910

Glu Leu His Tyr Ser Gln Glu Leu Ser Leu Leu Tyr Ile Leu Gln
            2915                2920                2925

Asp Asp Val Asp Arg Ala Lys Tyr Tyr Ile Glu Asn Cys Ile Arg
```

```
                    2930                2935                2940
Ile Phe Met Gln Ser Tyr Ser Ser Ile Asp Val Leu Leu Glu Arg
                    2945                2950                2955
Ser Arg Leu Thr Lys Leu Gln Ser Leu Gln Ala Leu Ile Glu Ile
                    2960                2965                2970
Gln Glu Phe Ile Ser Phe Ile Arg Lys Gln Gly Asn Leu Ser Xaa
                    2975                2980                2985
Ser Pro
```

(2) INFORMATION FOR SEQ ID NO: 30:

(i) SEQUENCE CHARACTERISTICS:
        (A) LENGTH: 3959 amino acid
        (B) TYPE: amino acid
        (C) STRANDEDNESS:
        (D) TOPOLOGY: linear (ii) MOLECULE TYPE: protein (iii) HYPOTHETICAL: no (iv) ANTI-SENSE: no (v) SEQUENCE DESCRIPTION: SEQ ID NO: 30:

```
Val Tyr Glu Leu Leu Gly Val Leu Gly Glu Val His Pro Ser Glu
                 5                  10                  15
Met Ile Ser Asn Ser Glu Gln Leu Phe Arg Ala Phe Leu Gly Glu
                20                  25                  30
Leu Lys Ser Gln Met Thr Ser Thr Val Arg Glu Pro Lys Leu Pro
                35                  40                  45
Val Leu Ala Gly Cys Leu Lys Gly Leu Ser Ser Leu Met Cys Asn
                50                  55                  60
Phe Thr Lys Ser Met Glu Glu Asp Pro Gln Thr Ser Arg Glu Ile
                65                  70                  75
Phe Asp Phe Ala Leu Lys Ala Ile Arg Pro Gln Ile Asp Leu Lys
                80                  85                  90
Arg Tyr Ala Val Pro Leu Ala Gly Leu Cys Leu Phe Thr Leu His
                95                 100                 105
Ala Ser Gln Phe Ser Thr Cys Leu Leu Glu Asn Tyr Val Ser Leu
               110                 115                 120
Phe Glu Val Leu Ser Lys Trp Cys Gly His Thr Asn Ile Glu Leu
               125                 130                 135
Lys Lys Ala Ala His Ser Ala Leu Glu Ser Phe Leu Lys Gln Val
               140                 145                 150
Ser Phe Met Val Ala Lys Asp Ala Glu Arg His Lys Asn Lys Leu
               155                 160                 165
Gln Tyr Phe Met Glu Gln Phe Tyr Gly Ile Ile Arg Asn Met Asp
               170                 175                 180
Ser Asn Ser Lys Asp Leu Ser Ile Ala Ile Arg Gly Tyr Gly Leu
               185                 190                 195
Phe Ala Gly Pro Cys Lys Val Ile Asn Ala Lys Asp Val Asp Phe
               200                 205                 210
Met Tyr Val Glu Leu Ile Gln Arg Cys Lys Gln Leu Phe Leu Thr
               215                 220                 225
Gln Thr Asp Thr Val Asp Asp His Ile Tyr Gln Met Pro Ser Phe
               230                 235                 240
Leu Gln Ser Ile Val Ser Val Leu Leu Tyr Leu Asp Thr Ile Pro
```

-continued

```
                    245                 250                 255
Glu Val Tyr Thr Pro Val Leu Glu His Leu Met Val Val Gln Ile
                260                 265                 270
Asp Ser Phe Pro Gln Tyr Ser Pro Lys Met Gln Pro Val Cys Cys
                275                 280                 285
Arg Ala Ile Val Lys Leu Phe Leu Ala Leu Ala Glu Lys Gly Pro
                290                 295                 300
Val Leu Trp Asn Cys Ile Ser Thr Val His Gln Gly Leu Ile
                305                 310                 315
Arg Ile Cys Ser Lys Pro Val Val Phe Gln Lys Gly Ala Gly Ser
                320                 325                 330
Glu Ser Glu Asp Tyr His Thr Ser Glu Glu Ala Arg Thr Gly Lys
                335                 340                 345
Trp Lys Met Pro Thr Tyr Lys Asp Tyr Leu Asp Leu Phe Arg Tyr
                350                 355                 360
Leu Leu Ser Cys Asp Gln Met Met Asp Ser Leu Leu Ala Asp Glu
                365                 370                 375
Ala Phe Leu Phe Val Asn Ser Ser Leu His Ser Leu Asn Arg Leu
                380                 385                 390
Leu Tyr Asp Glu Phe Val Lys Ser Val Leu Lys Ile Val Glu Lys
                395                 400                 405
Leu Asp Leu Thr Leu Glu Lys Gln Asn Val Gly Glu Gln Glu Asp
                410                 415                 420
Glu Thr Glu Ala Thr Gly Val Trp Val Ile Pro Thr Ser Asp Pro
                425                 430                 435
Ala Ala Asn Leu His Pro Ala Lys Pro Lys Asp Phe Ser Ala Phe
                440                 445                 450
Ile Asn Leu Val Glu Phe Cys Arg Glu Ile Leu Pro Glu Lys His
                455                 460                 465
Val Glu Phe Phe Glu Pro Trp Val Tyr Ser Phe Ala Tyr Glu Leu
                470                 475                 480
Ile Leu Gln Ser Thr Arg Leu Pro Leu Ile Ser Val Phe Tyr Lys
                485                 490                 495
Leu Leu Ser Val Ala Val Arg Asn Ala Lys Lys Met Lys Tyr Phe
                500                 505                 510
Glu Gly Val Gly Pro Lys Ser Gln Lys Gln Ser Pro Glu Asp Leu
                515                 520                 525
Glu Lys Tyr Ser Cys Phe Ala Leu Phe Ala Lys Phe Ser Lys Glu
                530                 535                 540
Val Ser Ile Lys Met Lys Gln Tyr Lys Asp Glu Leu Leu Ala Ser
                545                 550                 555
Cys Leu Thr Phe Ile Leu Ser Leu Pro His Asp Ile Ile Glu Leu
                560                 565                 570
Asp Val Arg Ala Tyr Val Pro Ala Leu Gln Met Ala Phe Lys Leu
                575                 580                 585
Gly Leu Ser Tyr Thr Pro Leu Ala Glu Val Gly Leu Asn Ala Leu
                590                 595                 600
Glu Glu Trp Ser Gly Tyr Ile Cys Lys His Val Ile Gln Pro Tyr
                605                 610                 615
Tyr Lys Asp Ile Leu Pro Ser Leu Asp Gly Tyr Leu Lys Thr Ser
                620                 625                 630
Val Leu Ser Asp Glu Thr Lys Asn Ser Trp Gln Val Ser Ala Leu
                635                 640                 645
```

-continued

Ser Arg Ala Ala Gln Lys Gly Phe Asn Lys Val Leu Lys His
                650                 655                 660

Leu Thr Lys Thr Lys Ser Ile Ser Ser Asn Glu Ala Leu Ser Leu
            665                 670                 675

Glu Glu Val Arg Ile Arg Val Arg Ile Leu Gly Ser Leu Gly
            680                 685                 690

Gly Gln Ile Asn Lys Asn Leu Val Thr Ala Ala Ser Ser Asp Glu
            695                 700                 705

Met Met Lys Lys Cys Val Ala Trp Asp Arg Glu Lys Arg Leu Arg
            710                 715                 720

Phe Ala Val Pro Phe Met Glu Met Lys Pro Val Ile Tyr Leu Asp
            725                 730                 735

Leu Phe Leu Pro Arg Val Thr Glu Leu Ala Leu Ser Ala Ser Asp
            740                 745                 750

Arg Gln Thr Thr Val Ala Ala Cys Glu Leu Leu His Ser Met Val
            755                 760                 765

Met Phe Met Leu Gly Lys Ala Thr Gln Met Pro Glu Asp Gly Gln
            770                 775                 780

Gly Ser Pro Pro Met Tyr Gln Leu Tyr Lys Arg Thr Phe Pro Val
            785                 790                 795

Leu Leu Arg Leu Ala Cys Asp Val Asp Gln Val Thr Arg Gln Leu
            800                 805                 810

Tyr Glu Pro Leu Val Met Gln Leu Ile His Trp Phe Thr Asn Asn
            815                 820                 825

Lys Lys Phe Glu Ser Gln Asp Thr Val Ala Leu Leu Glu Thr Ile
            830                 835                 840

Leu Asp Gly Ile Val Asp Pro Val Asp Ser Thr Leu Arg Asp Phe
            845                 850                 855

Cys Gly Gln Cys Ile Gln Glu Phe Leu Lys Trp Ser Ile Lys Gln
            860                 865                 870

Thr Thr Pro Gln Gln Glu Lys Ser Pro Val Asn Thr Lys Ser
            875                 880                 885

Leu Phe Lys Arg Leu Tyr Ser Phe Ala Leu His Pro Asn Ala Phe
            890                 895                 900

Lys Arg Leu Gly Ala Ser Leu Ala Phe Asn Asn Ile Tyr Arg Glu
            905                 910                 915

Phe Arg Glu Glu Glu Ser Leu Val Glu Gln Phe Val Phe Glu Ala
            920                 925                 930

Leu Val Thr Tyr Met Glu Ser Leu Ala Leu Ala His Thr Asp Glu
            935                 940                 945

Lys Ser Leu Gly Thr Ile Gln Gln Cys Cys Asp Ala Ile Asp His
            950                 955                 960

Leu Ser Leu Ile Ile Glu Lys Lys His Val Ser Leu Asn Lys Ala
            965                 970                 975

Lys Lys Arg Arg Leu Pro Arg Gly Phe Pro Pro Ala Thr Ser Leu
            980                 985                 990

Cys Leu Leu Asp Val Val Gln Trp Leu Leu Ala Asn Cys Gly Arg
            995                1000                1005

Pro Gln Thr Glu Cys Arg His Lys Ser Ile Glu Leu Phe Tyr Lys
            1010                1015                1020

Phe Val Thr Leu Leu Pro Gly Asn Lys Ser Pro Phe Leu Trp Leu
            1025                1030                1035

-continued

```
Lys Asp Ile Ile Lys Lys Glu Asp Ile Ser Phe Leu Ile Asn Thr
        1040                1045                1050
Phe Glu Gly Gly Gly Ser Gly Arg Pro Ser Gly Ile Leu Ala Gln
        1055                1060                1065
Pro Thr Leu Phe His Leu Gln Gly Pro Phe Ser Leu Arg Ala Ala
        1070                1075                1080
Leu Gln Trp Met Asp Met Leu Ala Ala Leu Glu Cys Tyr Asn
        1085                1090                1095
Thr Phe Ile Glu Glu Lys Thr Leu Glu Ala Pro Lys Val Leu Gly
        1100                1105                1110
Thr Glu Thr Gln Ser Ser Leu Trp Lys Ala Val Ala Phe Phe Leu
        1115                1120                1125
Glu Ser Ile Ala Met His Asp Ile Met Ala Ala Glu Lys Tyr Phe
        1130                1135                1140
Gly Thr Gly Ala Thr Gly Asn Arg Pro Ser Pro Gln Glu Gly Glu
        1145                1150                1155
Arg Tyr Asn Tyr Ser Lys Cys Thr Ile Val Val Arg Ile Met Glu
        1160                1165                1170
Phe Thr Thr Thr Leu Leu Ser Thr Ser Pro Glu Gly Trp Lys Leu
        1175                1180                1185
Leu Glu Lys Asp Val Cys Asn Thr Asn Leu Met Lys Leu Leu Val
        1190                1195                1200
Lys Thr Leu Cys Glu Pro Ser Ser Ile Gly Phe Asn Ile Gly Asp
        1205                1210                1215
Val Ala Val Met Asn Tyr Leu Pro Ser Val Cys Thr Asn Leu Met
        1220                1225                1230
Lys Ala Leu Lys Lys Ser Pro Tyr Lys Asp Ile Leu Glu Met His
        1235                1240                1245
Leu Lys Glu Lys Ile Thr Ala Gln Ser Ile Glu Glu Leu Cys Ala
        1250                1255                1260
Val Asp Leu Tyr Cys Pro Asp Ala Cys Val Asp Arg Ala Arg Leu
        1265                1270                1275
Ala Ser Val Val Ser Ala Cys Lys Gln Leu His Arg Ala Gly Val
        1280                1285                1290
Leu Cys Val Ile Ile Pro Ser Gln Ser Ala Asp Gln His His Ser
        1295                1300                1305
Ile Gly Thr Lys Leu Leu Ser Leu Val Tyr Lys Ser Ile Ala Pro
        1310                1315                1320
Gly Asp Glu Gln Gln Cys Leu Pro Ser Leu Asp Pro Asn Cys Lys
        1325                1330                1335
Arg Leu Ala Ser Gly Leu Leu Glu Leu Ala Phe Ala Phe Gly Gly
        1340                1345                1350
Leu Cys Glu His Leu Val Ser Leu Leu Leu Asp Thr Thr Val Leu
        1355                1360                1365
Ser Met Pro Ser Arg Gly Gly Ser Gln Lys Asn Ile Val Ser Phe
        1370                1375                1380
Ser His Gly Glu Tyr Phe Tyr Ser Leu Phe Ser Glu Thr Ile Asn
        1385                1390                1395
Thr Glu Leu Leu Lys Asn Leu Asp Leu Ala Val Leu Glu Leu Met
        1400                1405                1410
Lys Ser Ser Val Asp Asn Pro Lys Met Val Ser Asn Val Leu Asn
        1415                1420                1425
Gly Met Leu Asp Gln Ser Phe Arg Asp Arg Thr Ser Glu Lys His
```

-continued

```
                    1430                 1435                 1440

Gln Gly Leu Lys Leu Ala Thr Ile Ile Leu Gln Asn Trp Lys Lys
                    1445                 1450                 1455

Cys Asp Ser Trp Trp Ala Lys Asp Ser Ala Pro Glu Ser Lys Met
                    1460                 1465                 1470

Ala Val Leu Thr Leu Leu Ala Lys Ile Phe Gln Ile Asp Ser Ser
                    1475                 1480                 1485

Val Cys Phe Asn Thr Asn His Cys Met Phe Pro Glu Val Phe Thr
                    1490                 1495                 1500

Thr Tyr Val Ser Leu Leu Ala Asp Ser Lys Leu Asp Leu His Leu
                    1505                 1510                 1515

Lys Gly Gln Ala Ile Ile Leu Leu Pro Phe Phe Thr Ser Leu Thr
                    1520                 1525                 1530

Gly Gly Ser Leu Glu Asp Leu Lys Val Val Leu Glu Asn Leu Ile
                    1535                 1540                 1545

Val Ser Asn Phe Pro Met Lys Ser Glu Glu Phe Pro Pro Gly Thr
                    1550                 1555                 1560

Leu Gln Tyr Asn Asn Tyr Val Asp Cys Met Lys Lys Phe Leu Asp
                    1565                 1570                 1575

Ala Leu Glu Leu Ser Lys Ser Pro Met Leu Leu Gln Leu Met Thr
                    1580                 1585                 1590

Glu Ile Leu Cys Arg Glu Gln Gln His Val Met Glu Glu Leu Phe
                    1595                 1600                 1605

Gln Ser Thr Phe Lys Lys Ile Ala Arg Lys Ser Ser Cys Ile Thr
                    1610                 1615                 1620

Gln Leu Gly Leu Leu Glu Ser Val Tyr Arg Met Phe Arg Arg Asp
                    1625                 1630                 1635

Asp Leu Leu Ser Asn Ile Thr Arg Gln Ala Phe Val Asp Arg Ser
                    1640                 1645                 1650

Leu Leu Thr Leu Leu Trp His Cys Ser Leu Asn Ala Leu Arg Glu
                    1655                 1660                 1665

Phe Phe Ser Lys Ile Val Val Glu Ala Ile Asn Val Leu Lys Ser
                    1670                 1675                 1680

Arg Phe Ile Lys Leu Asn Glu Ser Ala Phe Asp Thr Gln Ile Thr
                    1685                 1690                 1695

Lys Lys Met Gly Tyr Tyr Lys Met Leu Asp Val Met Tyr Ser Arg
                    1700                 1705                 1710

Leu Pro Lys Asp Asp Val His Ser Lys Glu Ser Lys Ile Asn Gln
                    1715                 1720                 1725

Val Phe His Gly Ser Cys Ile Thr Glu Gly Ser Glu Leu Thr Lys
                    1730                 1735                 1740

Thr Leu Ile Lys Leu Cys Tyr Asp Ala Phe Thr Glu Asn Met Ala
                    1745                 1750                 1755

Gly Glu Asn Gln Leu Leu Glu Arg Arg Arg Leu Tyr His Cys Ala
                    1760                 1765                 1770

Ala Tyr Asn Cys Ala Ile Ser Val Val Cys Cys Val Phe Asn Glu
                    1775                 1780                 1785

Leu Lys Phe Tyr Gln Gly Phe Leu Phe Thr Glu Lys Pro Glu Lys
                    1790                 1795                 1800

Asn Leu Leu Ile Phe Glu Asn Leu Ile Asp Leu Lys Arg Cys Tyr
                    1805                 1810                 1815

Thr Phe Pro Ile Glu Val Glu Val Pro Met Glu Arg Lys Lys Lys
                    1820                 1825                 1830
```

-continued

```
Tyr Leu Glu Ile Arg Lys Glu Ala Arg Glu Ala Ala Ala Ser Gly
                1835                1840                1845

Asp Ser Asp Gly Pro Arg Tyr Ile Ser Ser Leu Ser Tyr Leu Ala
                1850                1855                1860

Asp Ser Ser Leu Ser Glu Glu Met Ser Gln Phe Asp Phe Ser Thr
                1865                1870                1875

Gly Val Gln Ser Tyr Ser Tyr Ser Ser Gln Asp Pro Lys Ser Thr
                1880                1885                1890

Thr Ala His Phe Arg Arg Gln Lys His Lys Glu Ser Met Ile Gln
                1895                1900                1905

Asp Asp Ile Leu Glu Leu Glu Met Asp Glu Leu Asn Gln His Glu
                1910                1915                1920

Cys Met Ala Thr Met Thr Ala Leu Ile Lys His Met Gln Arg Asn
                1925                1930                1935

Gln Ile Leu Pro Lys Glu Glu Gly Ser Val Pro Arg Asn Leu
                1940                1945                1950

Pro Pro Trp Met Lys Phe Leu His Asp Lys Leu Gly Asn Pro Ser
                1955                1960                1965

Ile Ser Leu Asn Ile Arg Leu Phe Leu Ala Lys Leu Val Ile Asn
                1970                1975                1980

Thr Glu Glu Val Phe Arg Pro Tyr Ala Arg Tyr Trp Leu Ser Pro
                1985                1990                1995

Leu Leu Gln Leu Val Val Ser Gly Asn Asn Gly Gly Glu Gly Ile
                2000                2005                2010

His Tyr Met Val Val Glu Ile Val Val Ile Ile Leu Ser Trp Thr
                2015                2020                2025

Gly Leu Ala Thr Pro Ile Gly Val Pro Lys Asp Glu Val Leu Ala
                2030                2035                2040

Asn Arg Leu Leu His Phe Leu Met His Val Phe His Gln Lys Arg
                2045                2050                2055

Ala Val Phe Arg His Asn Leu Glu Ile Ile Lys Thr Leu Val Glu
                2060                2065                2070

Cys Trp Lys Asp Cys Leu Ser Ile Pro Tyr Arg Leu Ile Phe Glu
                2075                2080                2085

Lys Phe Ser Ser Thr Asp Pro Asn Ser Lys Asp Asn Ser Val Gly
                2090                2095                2100

Ile Gln Leu Leu Gly Ile Val Met Ala Asn Asn Leu Pro Pro Tyr
                2105                2110                2115

Asp Pro Lys Cys Gly Ile Glu Ser Ile Lys Tyr Phe Gln Ala Leu
                2120                2125                2130

Val Asn Asn Met Ser Phe Val Arg Tyr Arg Glu Val Tyr Ala Ala
                2135                2140                2145

Ala Ala Glu Val Leu Gly Leu Val Leu Arg Tyr Ile Thr Glu Arg
                2150                2155                2160

Glu Asn Ile Leu Glu Glu Ser Val Cys Glu Leu Val Ile Lys Gln
                2165                2170                2175

Leu Lys Gln His Gln Asn Thr Met Glu Asp Lys Phe Ile Val Cys
                2180                2185                2190

Leu Asn Lys Ala Val Lys Asn Phe Pro Pro Leu Ala Asp Arg Phe
                2195                2200                2205

Met Asn Thr Val Phe Phe Leu Leu Pro Lys Phe His Gly Val Met
                2210                2215                2220
```

```
Lys Thr Leu Cys Leu Glu Val Leu Cys Arg Ala Glu Ile
                2225                2230                2235

Thr Asp Leu Tyr Leu Gln Leu Lys Ser Lys Asp Phe Ile Gln Val
                2240                2245                2250

Met Arg His Arg Asp Asp Glu Arg Gln Lys Val Cys Leu Asp Ile
                2255                2260                2265

Ile Tyr Lys Met Met Ala Arg Leu Lys Pro Val Glu Leu Arg Glu
                2270                2275                2280

Leu Leu Asn Pro Val Val Glu Phe Ile Ser His Pro Ser Pro Val
                2285                2290                2295

Cys Arg Glu Gln Met Tyr Asn Ile Leu Met Trp Ile His Asp Asn
                2300                2305                2310

Tyr Arg Asp Pro Glu Gly Gln Thr Asp Asp Ser Gln Glu Ile
                2315                2320                2325

Phe Lys Leu Ala Lys Asp Val Leu Ile Gln Gly Leu Ile Asp Glu
                2330                2335                2340

Asn Pro Gly Leu Gln Leu Ile Ile Arg Asn Phe Trp Ser His Glu
                2345                2350                2355

Thr Arg Leu Pro Ser Asn Thr Leu Asp Arg Leu Leu Ala Leu Asn
                2360                2365                2370

Ser Leu Tyr Ser Pro Lys Ile Glu Ala His Phe Leu Ser Leu Ala
                2375                2380                2385

Thr Asp Phe Leu Leu Glu Met Thr Ser Val Ser Pro Asp Tyr Ser
                2390                2395                2400

Asn Pro Met Phe Asp His Pro Leu Ser Glu Cys Lys Phe Gln Glu
                2405                2410                2415

Tyr Thr Ile Asp Ser Asp Trp Arg Phe Arg Ser Thr Val Leu Thr
                2420                2425                2430

Pro Met Phe Ile Glu Thr Gln Ala Ser Gln Ser Ala Leu Gln Thr
                2435                2440                2445

Arg Thr Gln Glu Gly Ser Leu Ser Ala Arg Gly Val Met Thr Gly
                2450                2455                2460

Gln Ile Arg Ala Thr Gln Gln Tyr Asp Phe Thr Pro Thr Gln
                2465                2470                2475

Asn Thr Asp Gly Arg Ser Ser Phe Asn Trp Leu Thr Gly Asn Ser
                2480                2485                2490

Ile Asp Pro Leu Val Asp Phe Thr Val Ser Ser Ser Asp Ser
                2495                2500                2505

Leu Ser Ser Ser Leu Leu Phe Ala His Lys Arg Ser Glu Lys Ser
                2510                2515                2520

Gln Arg Gly Pro Leu Lys Ser Val Gly Pro Asp Phe Gly Lys Lys
                2525                2530                2535

Arg Leu Gly Leu Pro Gly Asp Glu Val Asp Asn Lys Ala Lys Gly
                2540                2545                2550

Thr Asp Asn Arg Ala Glu Ile Leu Arg Leu Arg Arg Phe Leu
                2555                2560                2565

Lys Asp Arg Glu Lys Leu Ser Leu Ile Tyr Ala Arg Lys Gly Val
                2570                2575                2580

Ala Glu Gln Lys Arg Glu Lys Glu Ile Lys Ser Glu Leu Lys Met
                2585                2590                2595

Lys His Asp Ala Gln Val Ile Leu Tyr Arg Ser Tyr Arg Gln Gly
                2600                2605                2610

Asp Leu Pro Asp Ile Gln Ile Lys Tyr Ser Ser Leu Ile Thr Pro
```

-continued

```
                     2615                2620                2625

Leu Gln Ala Val Ala Gln Arg Asp Pro Ile Ile Ala Lys Gln Leu
                     2630                2635                2640

Phe Gly Ser Leu Phe Ser Gly Ile Ile Lys Glu Met Asp Lys Tyr
                     2645                2650                2655

Lys Thr Met Ser Glu Lys Asn Asn Ile Thr Gln Lys Leu Leu Gln
                     2660                2665                2670

Asp Phe Asn Asn Phe Leu Asn Thr Thr Val Ser Phe Phe Pro Pro
                     2675                2680                2685

Phe Ile Ser Cys Ile Gln Glu Ile Ser Cys Gln His Ala Asp Leu
                     2690                2695                2700

Leu Ser Leu Asp Pro Ala Ser Val Ser Ala Ser Cys Leu Ala Ser
                     2705                2710                2715

Leu Gln Gln Pro Val Gly Val Arg Leu Leu Glu Glu Ala Leu Leu
                     2720                2725                2730

His Leu Leu Pro Glu Glu Pro Pro Ala Lys Arg Val Arg Gly Arg
                     2735                2740                2745

Pro Cys Leu Tyr Pro Asp Phe Val Arg Trp Met Glu Leu Ala Lys
                     2750                2755                2760

Leu Tyr Arg Ser Ile Gly Glu Tyr Asp Ile Leu Arg Gly Ile Phe
                     2765                2770                2775

Asn Ser Glu Ile Gly Thr Lys Gln Val Thr Gln Asn Ala Leu Leu
                     2780                2785                2790

Ala Glu Ala Arg Asn Asp Tyr Ser Glu Ala Val Lys Gln Tyr Asn
                     2795                2800                2805

Glu Ala Leu Asn Lys Gln Asp Trp Val Asp Gly Glu Pro Met Glu
                     2810                2815                2820

Ala Glu Lys Asp Phe Trp Glu Leu Ala Ser Leu Asp Cys Tyr Asn
                     2825                2830                2835

Gln Leu Ala Glu Trp Lys Ser Leu Ala Tyr Cys Ser Thr Val Ser
                     2840                2845                2850

Val Asp Ser Ala Asn Pro Pro Asp Leu Asn Lys Met Trp Asn Glu
                     2855                2860                2865

Pro Phe Tyr Gln Glu Thr Tyr Leu Pro Tyr Met Ile Arg Ser Lys
                     2870                2875                2880

Leu Lys Leu Leu Leu Gln Gly Glu Gly Asp Gln Ser Leu Leu Thr
                     2885                2890                2895

Phe Ile Asp Glu Ala Val Ser Lys Glu Leu Gln Lys Val Leu Val
                     2900                2905                2910

Glu Leu His Tyr Ser Gln Glu Leu Ser Leu Leu Tyr Ile Leu Gln
                     2915                2920                2925

Asp Asp Val Asp Arg Ala Lys Tyr Tyr Ile Glu Asn Cys Ile Arg
                     2930                2935                2940

Ile Phe Met Gln Ser Tyr Ser Ser Ile Asp Val Leu Leu Glu Arg
                     2945                2950                2955

Ser Arg Leu Thr Lys Leu Gln Ser Leu Gln Ala Leu Ile Glu Ile
                     2960                2965                2970

Gln Glu Phe Ile Ser Phe Ile Arg Lys Gln Gly Asn Leu Ser Ser
                     2975                2980                2985

Gln Ile Pro Leu Lys Arg Leu Leu Lys Thr Trp Thr Asn Arg Tyr
                     2990                2995                3000

Pro Asp Ala Lys Met Asp Pro Met Asn Ile Trp Asp Asp Ile Ile
                     3005                3010                3015
```

```
Thr Asn Arg Cys Phe Phe Leu Ser Lys Ile Glu Glu Lys Leu Thr
            3020                3025                3030
Ile Pro Pro Asp Asp His Ser Met Asn Thr Asp Gly Asp Glu Asp
            3035                3040                3045
Ser Ser Asp Arg Met Lys Val Gln Glu Gln Glu Glu Asp Ile Tyr
            3050                3055                3060
Ser Leu Ile Lys Ser Gly Lys Phe Ser Met Lys Met Lys Met Ile
            3065                3070                3075
Glu Ser Ala Arg Lys Gln Lys Asn Phe Ser Leu Ala Met Lys Leu
            3080                3085                3090
Leu Lys Glu Leu His Lys Glu Ser Lys Thr Arg Asp Asp Trp Leu
            3095                3100                3105
Val Lys Trp Val Gln Ser Tyr Cys Arg Leu Ser His Ser Arg Ser
            3110                3115                3120
Gln Thr Gln Asn Arg Pro Glu Gln Ile Leu Thr Val Leu Lys Thr
            3125                3130                3135
Val Ser Leu Leu Asp Glu Asn Thr Ser Ser Tyr Leu Ser Lys Asn
            3140                3145                3150
Ile Pro Val Ser Arg Asp His Asn Ile Leu Leu Gly Thr Thr Tyr
            3155                3160                3165
Arg Ile Ile Ala Asn Ala Leu Ser Ser Asp Pro Thr Cys Leu Ala
            3170                3175                3180
Glu Ile Gly Glu Ser Lys Ala Arg Arg Ile Leu Glu Leu Ser Gly
            3185                3190                3195
Ser Ser Leu Glu Asn Ala Glu Glu Val Ile Ala Gly Leu Tyr Gln
            3200                3205                3210
Arg Val Leu His His Leu Ser Glu Ala Val Arg Ile Ala Glu Glu
            3215                3220                3225
Glu Ala Gln Pro Phe Thr Arg Gly Gln Glu Pro Ala Val Gly Val
            3230                3235                3240
Ile Asp Ala Tyr Met Thr Leu Val Asp Phe Cys Asp Gln Gln Leu
            3245                3250                3255
Arg Lys Glu Glu Glu Ser Ser Ser Val Thr Glu Ser Val Gln Leu
            3260                3265                3270
Gln Met Tyr Pro Ala Leu Val Val Asp Lys Met Leu Lys Ala Leu
            3275                3280                3285
Arg Leu Asp Ser Asn Glu Ala Arg Leu Lys Phe Pro Arg Leu Leu
            3290                3295                3300
Gln Ile Ile Glu Arg Tyr Pro Glu Glu Thr Leu Ser Leu Met Thr
            3305                3310                3315
Lys Glu Ile Ser Ser Ile Pro Cys Trp Gln Phe Ile Gly Trp Ile
            3320                3325                3330
Ser His Met Val Ala Leu Leu Asp Lys Glu Glu Ala Val Ala Val
            3335                3340                3345
His Arg Thr Val Glu Glu Ile Ala Asp Asn Tyr Pro Gln Ala Met
            3350                3355                3360
Val Tyr Pro Phe Ile Ile Ser Ser Glu Ser Tyr Ser Phe Lys Asp
            3365                3370                3375
Thr Ser Thr Gly Tyr Lys Asn Lys Glu Phe Val Glu Arg Ile Lys
            3380                3385                3390
Ile Lys Leu Asp Gln Gly Gly Val Ile Gln Asp Phe Ile Asn Ala
            3395                3400                3405
```

-continued

```
Leu Glu Gln Leu Ser His Pro Glu Met Leu Phe Lys Asp Trp Thr
            3410                3415                3420
Asp Asp Ile Lys Val Glu Leu Glu Lys Asn Pro Val Asn Arg Lys
            3425                3430                3435
Asn Ile Glu Lys Met Tyr Glu Lys Met Tyr Ala Thr Leu Gly Asp
            3440                3445                3450
Pro Gln Ala Pro Gly Leu Gly Ala Phe Arg Arg Cys Ile Gln
            3455                3460                3465
Gly Phe Gly Lys Glu Phe Asp Lys His Phe Gly Arg Gly Ser
            3470                3475                3480
Lys Leu Pro Gly Met Lys Ser Arg Glu Phe Ser Asp Ile Thr Asn
            3485                3490                3495
Ser Leu Phe Ser Lys Met Cys Glu Val Ser Lys Pro Pro Gly Asn
            3500                3505                3510
Leu Lys Glu Cys Ser Pro Trp Met Ser Asp Phe Lys Val Glu Phe
            3515                3520                3525
Leu Arg Ser Glu Leu Glu Ile Pro Gly Gln Tyr Asp Gly Lys Gly
            3530                3535                3540
Lys Pro Val Pro Glu Tyr His Ala Arg Ile Ala Gly Phe Asp Glu
            3545                3550                3555
Arg Ile Lys Val Met Ala Ser Met Arg Lys Pro Lys Arg Ile Ile
            3560                3565                3570
Ile Arg Gly His Asp Glu Arg Glu Tyr Pro Phe Leu Val Lys Gly
            3575                3580                3585
Gly Glu Asp Leu Arg Gln Asp Gln Arg Ile Glu Gln Leu Phe Glu
            3590                3595                3600
Val Met Asn Val Ile Leu Ser Gln Asp Ala Thr Cys Ser Gln Arg
            3605                3610                3615
Ser Met Gln Leu Lys Thr Tyr Gln Val Ile Pro Met Thr Ser Arg
            3620                3625                3630
Leu Gly Leu Ile Glu Trp Ile Glu Asn Thr Phe Thr Leu Lys Glu
            3635                3640                3645
Leu Leu Leu Ser Asn Met Ser Gln Glu Glu Lys Ala Ala Cys Thr
            3650                3655                3660
Arg Asp Pro Lys Ala Pro Pro Phe Glu Tyr Arg Asp Trp Leu Thr
            3665                3670                3675
Lys Met Ser Gly Lys Cys Asp Val Gly Ala Tyr Met Leu Met Tyr
            3680                3685                3690
Lys Gly Ala Ser Arg Thr Glu Thr Val Thr Ser Phe Arg Lys Arg
            3695                3700                3705
Glu Ser Lys Val Pro Ala Asp Leu Leu Lys Arg Ala Phe Val Lys
            3710                3715                3720
Met Ser Thr Ser Pro Glu Ala Phe Leu Thr Leu Arg Ser His Phe
            3725                3730                3735
Ala Gly Ser His Ala Leu Ile Cys Ile Ser His Trp Ile Pro Gly
            3740                3745                3750
Ile Gly Asp Arg His Leu Asn Asn Phe Leu Val Ser Met Glu Thr
            3755                3760                3765
Gly Gly Val Ile Gly Ile Asp Phe Gly His Ala Phe Gly Ser Ala
            3770                3775                3780
Thr Gln Phe Leu Pro Val Pro Glu Leu Met Pro Phe Arg Leu Thr
            3785                3790                3795
Arg Gln Phe Ile Asn Leu Met Leu Pro Met Lys Glu Thr Gly Val
```

```
                    3800              3805              3810
Met Tyr Ser Ile Met Val His Ala Leu Arg Ala Phe Arg Ser Gln
                3815              3820              3825
Ser Asn Leu Leu Ala Asn Thr Met Asp Val Phe Val Lys Glu Pro
                3830              3835              3840
Ser Phe Asp Trp Lys Asn Phe Glu Gln Lys Met Arg Lys Lys Gly
                3845              3850              3855
Gly Ser Trp Ile Gln Glu Ile Asn Val Thr Glu Lys Asn Trp Tyr
                3860              3865              3870
Pro Arg Gln Lys Ile His Tyr Ala Lys Arg Lys Leu Ala Gly Ala
                3875              3880              3885
Asn Pro Ala Val Ile Thr Cys Asp Glu Leu Leu Leu Gly His Glu
                3890              3895              3900
Lys Ala Ala Ala Phe Gly Asp Tyr Val Ala Val Ala Arg Gly Ser
                3905              3910              3915
Glu Asp His Asn Ile Arg Ala Gln Glu Leu Glu Ser Asp Leu Ser
                3920              3925              3930
Glu Glu Ala Gln Val Lys Cys Leu Ile Asp Gln Ala Thr Asp Pro
                3935              3940              3945
Asn Ile Leu Gly Arg Thr Leu Val Gly Trp Glu Pro Trp Met
                3950              3955
```

(2) INFORMATION FOR SEQ ID NO:31:

(i) SEQUENCE CHARACTERISTICS:
        (A) LENGTH: 11878 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 31:

```
GTATATGAGC TCCTAGGAGT ATTAGGTGAA GTTCATCCTA GTGAGATGAT AAGTAATTCA    60

GAACAACTGT TCCGGGCTTT TCTGGGTGAA CTTAAGTCCC AGATGACATC AACAGTAAGA   120

GAGCCCAAAC TACCTGTTCT GGCAGGGTGT CTGAAGGGAT TGTCATCACT TATGTGTAAC   180

TTCACTAAGT CCATGGAAGA AGATCCCCAG ACTTCAAGGG AGATTTTTGA TTTTGCGTTA   240

AAGGCAATTC GTCCTCAGAT TGATCTGAAG AGATATGCAG TGCCCTTAGC TGGTTTATGC   300

TTATTTACCC TGCATGCATC TCAATTTAGC ACCTGCCTTT TGGAGAACTA CGTTTCTTTG   360

TTTGAAGTGC TGTCAAAATG GTGTGGCCAT ACAAACATAG AATTGAAAAA AGCCGCACAT   420

TCAGCTCTGG AGTCTTTTCT GAAACAGGTT TCTTTTATGG TGGCAAAAGA TGCAGAAAGG   480

CATAAGAATA AGCTGCAGTA CTTTATGGAG CAATTCTATG GAATCATCAG GAACATGGAT   540

TCAAATAGCA AGGATTTATC AATTGCAATT CGTGGATATG GACTTTTTGC AGGCCCTTGC   600

AAGGTTATAA ACGCAAAAGA TGTTGACTTC ATGTACGTAG AGCTCATTCA GCGCTGCAAG   660

CAGCTGTTCC TCACCCAGAC AGATACTGTT GATGACCATA TTTACCAGAT GCCCAGTTTC   720

CTCCAATCTA TTGTAAGTGT CTTGCTTTAC CTTGATACAA TTCCTGAGGT GTATACTCCG   780
```

-continued

```
GTTCTGGAAC ATCTCATGGT GGTACAGATA GACAGCTTCC CACAGTATAG TCCAAAAATG      840
CAGCCGGTGT GTTGTAGAGC CATAGTGAAA CTTTTCCTAG CCTTAGCAGA AAAGGGACCA      900
GTTCTCTGGA ATTGCATTAG TACTGTGGTG CATCAAGGTT TAATTAGAAT ATGTTCTAAA      960
CCAGTCGTCT TTCAAAAGGG TGCTGGGTCT GAATCCGAAG ACTATCATAC ATCAGAGGAA     1020
GCTAGAACTG GCAAATGGAA AATGCCCACA TACAAAGACT ATTTGGATCT TTTTAGATAT     1080
CTCCTGAGCT GTGACCAGAT GATGGATTCT CTTTTAGCAG ATGAAGCATT TCTCTTTGTG     1140
AATTCCTCCC TTCATAGTCT GAATCGTTTG CTGTATGATG AATTTGTAAA ATCAGTTTTG     1200
AAGATTGTTG AGAAATTGGA TCTTACACTA GAAAACAGA ATGTTGGGGA GCAAGAGGAT      1260
GAAACTGAAG CTACTGGTGT TTGGGTGATC CCGACTTCAG ATCCAGCGGC TAACTTGCAC     1320
CCTGCTAAAC CTAAAGATTT TTCAGCTTTC ATTAACCTGG TGGAATTTTG CAGAGAGATT     1380
CTTCCTGAGA AACATGTAGA ATTTTTTGAG CCATGGGTTT ACTCATTTGC GTATGAATTA     1440
ATTTTGCAGT CTACACGGTT ACCACTCATC AGTGTTTTTT ACAAATTGCT TTCTGTTGCT     1500
GTGAGAAATG CCAAGAAAAT GAAGTATTTT GAAGGAGTTG GTCCAAAGAG TCAGAAACAG     1560
TCTCCTGAGG ACCTAGAAAA GTATTCTTGC TTTGCTTTGT TTGCAAAATT TAGTAAAGAG     1620
GTATCAATTA AAATGAAGCA ATACAAAGAT GAACTTTTGG CCTCCTGTTT GACCTTTATT     1680
CTGTCCCTGC CACATGACAT CATTGAACTT GATGTTAGAG CCTACGTTCC TGCATTGCAG     1740
ATGGCTTTTA AACTGGGCCT GAGCTATACT CCATTGGCGG AAGTAGGCCT GAATGCTCTA     1800
GAAGAATGGT CAGGTTACAT CTGCAAACAT GTAATTCAGC CCTATTATAA GGACATTCTA     1860
CCCAGCCTTG ATGGATATCT GAAAACTTCA GTCTTATCAG ATGAGACCAA GAATAGCTGG     1920
CAAGTGTCAG CACTTTCTCG GGCTGCCCAG AAAGGATTTA ATAAAGTTGT GCTAAAGCAT     1980
CTGACAAAGA CAAAGAGCAT TTCATCAAAT GAAGCACTGT CCTTAGAAGA AGTGAGGATT     2040
AGAGTAGTCG GATACTTGGC TCTCTAGGAG GACAAATAAA CAAGAATCTC GTAACAGCTG     2100
CATCATCAGA TGAAATGATG AAGAAGTGTG TGGCATGGGA CAGAGAAAAA AGACTCCGTT     2160
TTGCAGTACC ATTTATGGAG ATGAAGCCTG TCATTTATCT GGATCTATTC CTGCCTCGGG     2220
TCACCGAGTT AGCTCTTTCA GCTAGTGACA GGCAGACTAC AGTTGCAGCC TGTGAACTTT     2280
TACATAGCAT GGTTATGTTT ATGTTGGGAA AAGCCACTCA GATGCCTGAA GATGGTCAGG     2340
GTTCCCCACC CATGTACCAG CTCTATAAGC GAACTTTTCC TGTTTTACTT CGACTTGCAT     2400
GTGATGTAGA TCAGGTGACA AGGCAACTGT ATGAGCCACT AGTTATGCAA CTGATTCACT     2460
GGTTCACTAA CAACAAGAAA TTTGAAAGTC AGGACACTGT CGCCTTACTA GAAACGATAT     2520
TGGATGGAAT TGTGGACCCT GTTGACAGTA CTTTGAGAGA TTTTTGTGGT CAGTGTATTC     2580
AAGAATTCCT TAAATGGTCC ATTAAGCAGA CGACACCACA GCAGCAGGAA AAAAGTCCAG     2640
TAAATACCAA ATCGCTTTTC AAGCGACTGT ATAGCTTTGC ACTTCATCCG AATGCCTTCA     2700
AGAGGCTGGG AGCATCACTT GCTTTTAATA ATATCTACAG GGAATTCAGG AAGAAGAGT     2760
CTCTGGTAGA ACAGTTTGTG TTTGAAGCCT TGGTAACGTA TATGGAAAGT CTGGCCTTAG     2820
CACATACAGA TGAGAAATCC TTAGGTACAA TTCAACAATG TTGTGATGCC ATTGATCATC     2880
TCAGTCTTAT CATTGAGAAG AAGCACGTTT CTTTAAACAA AGCAAAAAAA CGACGTTTGC     2940
CACGAGGCTT TCCACCTGCG ACATCACTGT GTTTATTGGA TGTGGTCCAG TGGCTTTTAG     3000
CAAATTGTGG GAGACCCCAG ACAGAATGTC GACACAAATC CATAGAACTC TTTTATAAAT     3060
TTGTTACTTT ATTGCCAGGC AACAAATCCC CTTTTTTATG GCTGAAAGAT ATTATCAAGA     3120
```

-continued

```
AAGAAGATAT TTCCTTTCTC ATAAACACAT TGAGGGCGG GGGAAGTGGT CGGCCGTCAG    3180
GCATCCTTGC TCAGCCAACC CTCTTCCATT TGCAAGGGCC GTTCAGTCTC AGAGCTGCCC    3240
TGCAGTGGAT GGACATGCTT CTGGCAGCAC TGGAGTGCTA CAACACATTC ATTGAAGAGA    3300
AAACTCTGGA AGCACCCAAG GTCCTAGGTA CTGAAACCCA GTCTTCACTT TGGAAAGCGG    3360
TGGCTTTCTT TTTAGAAAGC ATTGCTATGC ATGATATTAT GGCAGCAGAA AAGTACTTTG    3420
GCACTGGGGC AACAGGTAAC AGACCCAGCC CACAAGAAGG AGAAAGATAT AATTATAGCA    3480
AATGTACAAT TGTGGTCCGC ATTATGGAAT TTACCACAAC GCTCCTCAGC ACCTCCCCAG    3540
AAGGCTGGAA GCTGCTTGAG AAGGATGTGT GTAACACAAA CCTTATGAAA CTCTTAGTGA    3600
AAACCCTGTG TGAGCCCTCA AGCATAGGTT TCAACATCGG AGATGTCGCA GTTATGAACT    3660
ATCTTCCCAG TGTTTGTACC AACCTGATGA AGCACTGAA GAAGTCCCCA TACAAAGACA     3720
TCCTGGAGAT GCACCTCAAG GAAAAGATAA CAGCACAGAG CATTGAAGAG CTCTGTGCAG    3780
TTGACTTGTA TTGCCCTGAT GCTTGCGTGG ACAGGGCCAG GCTGGCTTCT GTCGTGTCAG    3840
CTTGTAAACA ACTTCATAGA GCGGGGGTTT TGTGTGTTAT AATACCATCT CAGTCTGCAG    3900
ATCAGCATCA TTCTATTGGC ACAAAACTTC TTTCCTTGGT TTATAAAAGC ATTGCACCTG    3960
GAGATGAACA ACAGTGCCTT CCTTCACTAG ATCCCAATTG TAAGCGATTG CCAGTGGAC     4020
TTCTGGAGTT GGCCTTTGCT TTTGGAGGAC TGTGTGAGCA CCTTGTGAGT CTTCTCCTGG    4080
ACACGACAGT GTTGTCATGC CATCCAGAGG AGGGTCCCAG AAAAACATCG TCAGCTTCTC    4140
TCATGGAGAG TATTTTTATA GCTTGTTCTC AGAAACGATC AACACTGAAT TGTTGAAAAA    4200
TCTAGATCTT GCTGTATTGG AGCTCATGAA ATCATCTGTG GATAATCCCA AAATGGTGAG    4260
CAATGTTTTG AATGGTATGT TAGATCAGAG CTTCAGGGAT CGAACCAGTG AGAAACACCA    4320
AGGACTGAAA CTTGCAACTA TAATTCTGCA AAACTGGAAG AAGTGTGATT CATGGTGGGC    4380
CAAAGATTCT GCTCCTGAAA GTAAAATGGC AGTGCTTACC TTGTTGGCAA AAATTTTCCA    4440
GATTGATTCA TCTGTTTGTT TTAATACAAA TCACTGCATG TTCCCTGAAG TCTTTACAAC    4500
ATATGTTAGT CTACTTGCTG ATTCAAAGTT GGACCTGCAT TTAAAGGGCC AAGCTATAAT    4560
TCTTCTTCCA TTCTTCACCA GTCTTACTGG AGGCAGCCTT GAGGACCTTA AGGTTGTTCT    4620
TGAAAACCTC ATCGTTTCTA ATTTTCCTAT GAAATCTGAA GAATTTCCCC CAGGAACTCT    4680
GCAGTACAAT AATTATGTGG ACTGCATGAA GAAGTTTCTA GATGCATTGG AATTATCTAA    4740
AAGCCCTATG TTGTTGCAGT TGATGACAGA AATTCTTTGT CGTGAACAGC AACATGTTAT    4800
GGAAGAATTA TTTCAGTCTA CTTTCAAAAA GATTGCCAGA AAGAGTTCAT GTATCACACA    4860
ATTAGGCCTT CTGGAAAGTG TATATAGAAT GTTCAGGAGG GATGACCTGC TTTCAAATAT    4920
CACTCGCCAA GCATTTGTAG ACCGTTCTCT GCTCACTCTG TTGTGGCACT GTAGCTTGAA    4980
TGCTTTGAGG GAATTTTTTA GCAAAATTGT GGTGGAAGCC ATTAATGTGT TGAAGTCCAG    5040
ATTTATAAAG CTGAATGAAT CTGCCTTTGA TACTCAAATC ACCAAGAAGA TGGGCTACTA    5100
TAAGATGTTA GATGTGATGT ATTCTCGTCT TCCAAAAGAT GATGTTCACT CTAAGGAATC    5160
TAAAATTAAT CAAGTTTTCC ATGGCTCATG TATTACAGAA GGAAGTGAAC TTACAAAGAC    5220
ACTTATTAAA TTGTGCTATG ATGCCTTTAC AGAGAACATG GCAGGCGAGA ACCAGTTGCT    5280
GGAGAGGAGA AGACTTTACC ATTGTGCTGC ATACAACTGT GCCATTTCTG TTGTCTGCTG    5340
TGTCTTCAAT GAATTAAAAT TTTACCAAGG TTTTCTGTTT ACTGAAAAAC CAGAAAAGAA    5400
CTTGCTTATT TTTGAAAATC TGATAGACTT GAAGCGCTGC TACACGTTTC CTATAGAAGT    5460
TGAGGTTCCT ATGGAGAGAA AGAAAAAGTA CCTTGAAATT AGAAAAGAAG CCAGGGAAGC    5520
```

-continued

```
AGCAGCAAGT GGGGATTCAG ATGGTCCTCG TTATATATCT TCCTTGTCAT ATTTGGCAGA   5580
CAGTAGCCTG AGTGAGGAAA TGAGTCAATT TGATTTCTCG ACTGGAGTGC AGAGCTATTC   5640
ATATAGTTCC CAAGACCCTA AATCTACCAC TGCTCATTTT CGGAGACAGA AACATAAAGA   5700
GTCCATGATC CAAGATGATA TCCTGGAGTT AGAGATGGAT GAACTCAATC AACACGAATG   5760
TATGGCAACT ATGACTGCTC TGATTAAGCA CATGCAGAGA AATCAGATCC TCCCTAAGGA   5820
AGAAGAGGGT TCAGTGCCAA GAAATCTTCC TCCTTGGATG AAATTTCTTC ATGACAAACT   5880
AGGAAATCCA TCAATATCAT TAAATATCCG TCTCTTCTTA GCCAAGCTTG TTATTAATAC   5940
AGAAGAAGTC TTTCGTCCTT ACGCGAGATA CTGGCTCAGC CCTTTGCTGC AGCTGGTTGT   6000
TTCTGGAAAC AACGGAGGAG AAGGAATTCA CTATATGGTG GTTGAGATAG TGGTTATTAT   6060
TCTTTCATGG ACAGGATTAG CTACTCCTAT AGGTGTCCCT AAAGATGAAG TGTTAGCAAA   6120
TCGATTGCTT CATTTCCTAA TGAACATGTT TTTCATCAAA AAAGAGCTGT GTTTAGACAC   6180
AACCTCGAAA TTATAAAAAC CCTTGTTGAA TGCTGGAAGG ATTGTTTATC CATCCCTTAC   6240
AGGTTAATAT TTGAAAAGTT TTCCAGTACA GATCCTAATT CTAAAGACAA TTCAGTAGGA   6300
ATTCAATTAC TAGGCATTGT AATGGCCAAT AACTTGCCTC CTTATGACCC AAAATGTGGC   6360
ATAGAGAGCA TAAAATACTT TCAAGCTTTG GTCAATAATA TGTCCTTTGT AAGATATAGA   6420
GAGGTATATG CAGCAGCGGC AGAAGTTCTA GGACTTGTTC TTCGATATAT TACTGAGAGA   6480
GAAAATATAC TGGAGGAGTC TGTGTGTGAA CTGGTCATAA AACAGTTGAA GCAACATCAG   6540
AATACGATGG AGGACAAATT TATTGTGTGC TTGAACAAAG CTGTGAAGAA CTTCCCTCCT   6600
CTTGCTGATA GGTTTATGAA CACCGTGTTC TTCCTGCTGC CAAAATTTCA TGGCGTGATG   6660
AAGACTCTCT GTCTGGAGGT GGTACTGTGT CGTGCAGAGG AAATAACAGA TCTATACTTA   6720
CAGTTAAAGA GCAAGGATTT CATTCAAGTC ATGAGACATA GAGATGATGA AGACAAAAAA   6780
GTGTGTTTGG ACATAATTTA TAAGATGATG GCAAGATTGA AACCAGTAGA ACTTCGAGAA   6840
CTTCTGAATC CTGTTGTAGA ATTCATTTCT CATCCTTCTC CAGTGTGTAG GGAACAAATG   6900
TATAACATTC TCATGTGGAT TCATGACAAT TATCGAGATC CAGAAGGTCA GACAGATGAC   6960
GACTCCCAGG AAATATTTAA GTTGGCAAAA GATGTGTTGA TTCAAGGATT GATCGATGAG   7020
AACCCTGGGC TTCAATTAAT TATTCGAAAT TTCTGGAGTC ATGAAACTAG GTTACCTTCA   7080
AATACCTTGG ATCGATTGTT GGCACTAAAT TCCCTATATT CTCCTAAGAT AGAAGCACAC   7140
TTTTTAAGTT TAGCAACAGA TTTTCTGCTT GAAATGACCA GCGTGAGCCC AGATTATTCA   7200
AACCCTATGT TTGATCATCC TCTGTCAGAA TGCAAATTTC AGGAATATAC TATTGATTCT   7260
GACTGGCGTT TCCGAAGTAC TGTTCTCACT CCAATGTTTA TTGAGACTCA GGCCTCCCAA   7320
AGTGCTCTGC AGACCCGGAC CCAGGAAGGA TCCCTCTCAG CTCGAGGGGT AATGACTGGG   7380
CAGATACGGG CCACACAACA GCAGTATGAT TTCACACCTA CGCAAAATAC AGATGGAAGA   7440
AGCTCTTTCA ATTGGCTGAC TGGGAACAGC ATTGACCCAC TGGTGGATTT TACGGTCTCC   7500
TCCTCATCTG ATTCTTTGTC TTCCTCCTTG CTGTTTGCTC ACAAGAGGAG TGAAAAATCA   7560
CAGAGAGGAC CCTTGAAGTC AGTAGGACCT GATTTTGGGA AAAAAAGGCT GGGCCTTCCA   7620
GGGGATGAGG TGGATAACAA AGCAAAAGGT ACAGACAATC GGGCGGAAAT ATTAAGATTA   7680
CGGAGACGAT TTTTAAAGGA CCGAGAAAAG CTCAGTTTGA TTTATGCCAG AAAAGGTGTT   7740
GCTGAACAAA AACGAGAGAA GGAGATCAAG AGTGAGTTAA AAATGAAGCA CGATGCCCAA   7800
GTCATTTTGT ACAGAAGTTA CCGTCAAGGA GACCTTCCTG ACATTCAGAT TAAATACAGC   7860
```

| | | | | |
|---|---|---|---|---|
| AGCCTGATCA | CTCCCTTGCA | AGCTGTGGCC | CAGAGAGACC | CAATAATTGC AAAGCAGCTC | 7920 |
| TTTGGCAGCT | TGTTTTCTGG | AATTATAAAA | GAGATGGATA | AATATAAGAC CATGTCTGAA | 7980 |
| AAAAACAACA | TTACTCAGAA | GTTGCTCCAG | GACTTCAATA | ATTTTCTTAA CACCACTGTC | 8040 |
| TCTTTCTTTC | CACCTTTCAT | CTCCTGTATC | CAGGAAATTA | GTTGCCAACA CGCAGACTTG | 8100 |
| CTGAGCCTCG | ACCCAGCTTC | TGTCAGTGCC | AGCTGCCTGG | CCAGTCTGCA GCAGCCTGTA | 8160 |
| GGCGTCCGCC | TTCTGGAGGA | GGCCTTGCTC | CACTGCTGCC | TGAAGAGCCA CCTGCCAAGC | 8220 |
| GAGTTCGAGG | GAGACCCTGT | CTCTACCCTG | ATTTTGTCAG | ATGGATGGAA CTTGCTAAAC | 8280 |
| TGTATAGATC | AATTGGAGAA | TATGACATCC | TCCGTGGGAT | TTTTAATAGT GAGATAGGAA | 8340 |
| CAAAGCAAGT | CACTCAGAAT | GCATTATTAG | CAGAAGCAAG | AAATGATTAT TCTGAAGCCG | 8400 |
| TTAAGCAGTA | TAATGAGGCT | CTCAATAAAC | AAGACTGGGT | AGATGGTGAG CCTATGGAAG | 8460 |
| CTGAGAAGGA | TTTTTGGGAA | CTTGCATCCC | TTGACTGTTA | TAACCAACTT GCTGAGTGGA | 8520 |
| AATCACTGGC | ATACTGTTCT | ACAGTCAGTG | TTGACAGTGC | GAACCCTCCA GATTTAAATA | 8580 |
| AAATGTGGAA | TGAACCATTT | TATCAGGAGA | CCTATCTACC | TTACATGATC CGCAGCAAGC | 8640 |
| TGAAGCTACT | TCTGCAAGGT | GAGGGAGACC | AGTCCCTGCT | GACATTTATT GATGAAGCTG | 8700 |
| TGAGCAAGGA | GCTCCAGAAG | GTCCTCGTAG | AGCTTCATTA | CAGTCAGGAA TTGAGTCTCC | 8760 |
| TTTATATCCT | ACAAGATGAC | GTCGACAGAG | CCAAATATTA | TATTGAAAAT TGCATTCGGA | 8820 |
| TTTTCATGCA | GAGCTATTCT | AGTATTGATG | TCCTTTTAGA | GAGAAGTAGA CTCACCAAAT | 8880 |
| TGCAATCTCT | ACAGGCTTTA | ATAGAAATTC | AGGAGTTCAT | CAGCTTTATA AGGAAACAAG | 8940 |
| GTAATTTATC | ATCTCAAATT | CCCCTTAAGA | GACTTCTAAA | AACCTGGACA ACAGATATC | 9000 |
| CGGATGCTAA | AATGGACCCA | ATGAACATCT | GGGATGACAT | CATCACAAAT CGATGTTTCT | 9060 |
| TTCTCAGCAA | AATAGAAGAA | AAACTGACTA | TTCCTCCAGA | TGATCATAGT ATGAACACAG | 9120 |
| ATGGAGATGA | AGATTCCAGT | GACAGAATGA | AAGTGCAGGA | GCAGGAGGAA GATATTTATT | 9180 |
| CTCTGATTAA | GAGTGGTAAG | TTTTCCATGA | AAATGAAGAT | GATAGAAAGT GCAAGGAAAC | 9240 |
| AGAAAAATTT | CTCACTAGCC | ATGAAACTAT | TAAAGGAGCT | TCATAAAGAG TCAAAAACAA | 9300 |
| GAGATGACTG | GCTGGTGAAA | TGGGTGCAGA | GCTACTGTCG | ACTCAGTCAC AGCCGGAGCC | 9360 |
| AGACCCAGAA | TCGTCCTGAG | CAGATCCTTA | CTGTGTTGAA | AACAGTCTCT TTGTTGGATG | 9420 |
| AGAACACATC | AAGCTACTTA | AGCAAAAATA | TTCCAGTTTC | CCGTGACCAC AACATTCTCT | 9480 |
| TGGGTACAAC | TTACAGGATC | ATAGCTAATG | CTCTCAGCAG | TGATCCAACT TGCCTTGCTG | 9540 |
| AAATCGGGGA | AAGCAAGGCT | AGAAGAATCT | TGGAGCTGTC | TGGATCCAGT TTAGAGAATG | 9600 |
| CAGAAGAGGT | GATCGCAGGT | CTATACCAGA | GAGTGTTGCA | TCACCTTTCT GAGGCCGTGC | 9660 |
| GGATTGCAGA | GGAGGAGGCC | CAGCCTTTCA | CTAGAGGCCA | GGAACCTGCA GTTGGGGTGA | 9720 |
| TAGATGCTTA | CATGACACTG | GTGGATTTCT | GTGACCAGCA | GCTCCGCAAG GAGGAAGAGA | 9780 |
| GTTCATCAGT | TACTGAGTCT | GTACAACTGC | AGATGTATCC | AGCCCTTGTG GTGGACAAAA | 9840 |
| TGTTAAAAGC | TTTAAGACTC | GATTCCAATG | AAGCCAGGCT | GAAGTTTCCC AGACTACTGC | 9900 |
| AGATTATAGA | ACGGTATCCA | GAGGAGACCC | TGAGCCTAAT | GACCAAAGAG ATTTCTTCCA | 9960 |
| TTCCTTGCTG | GCAGTTCATT | GGCTGGATCA | GCCACATGGT | GGCCTTACTG GACAAAGAGG | 10020 |
| AAGCTGTCGC | TGTCCATCGC | ACAGTGGAAG | AGATTGCTGA | TAACTATCCA CAGGCGATGG | 10080 |
| TCTACCCATT | TATAATAAGC | AGTGAAAGCT | ATTCCTTCAA | AGATACTTCT ACTGGTTATA | 10140 |
| AGAATAAGGA | GTTTGTGGAA | AGGATTAAAA | TTAAGTTGGA | TCAAGGAGGA GTGATTCAAG | 10200 |
| ATTTTATTAA | TGCCCTAGAA | CAGCTCTCTC | ATCCTGAAAT | CTCTTTAAGG ACTGGACTGA | 10260 |

```
TGATATCAAA GTTGAACTTG AAAAAAACCC TGTAAATAGA AAAAACATTG AAAAGATGTA      10320

TGAAAAAATG TATGCAACCT TGGGAGACCC ACAGGCTCCA GGTCTTGGGG CTTTTCGAAG      10380

AAGGTGTATT CAGGGTTTTG GAAAAGAATT TGATAAACAC TTTGGGAGAG GAGGTTCTAA      10440

GCTACCTGGA ATGAAATCCC GTGAATTCAG TGATATTACC AACTCACTAT TTTCAAAAAT      10500

GTGCGAAGTC TCAAAGCCAC CTGGGAATCT GAAAGAATGC TCGCCCTGGA TGAGTGACTT      10560

CAAAGTAGAA TTTTTGAGAA GTGAACTGGA GATTCCTGGT CAGTATGATG GCAAGGGAAA      10620

ACCAGTGCCA GAATACCATG CACGAATTGC TGGGTTTGAT GAGCGGATAA AGTAATGGC      10680

TTCTATGAGA AAACCAAAGC GTATCATCAT CCGAGGCCAT GATGAGAGAG AGTACCCTTT      10740

CCTTGTGAAG GGAGGTGAAG ATCTGAGGCA GGACCAACGC ATCGAGCAGC TCTTCGAGGT      10800

CATGAATGTC ATCCTTTCCC AAGATGCTAC CTGTAGTCAG AGAAGCATGC AGCTAAAGAC      10860

ATACCAGGTC ATACCCATGA CCTCCAGATT AGGACTAATT GAATGGATTG AAAATACTTT      10920

TACCTTGAAG GAACTTCTTT TGAGTAACAT GTCACAAGAG GAGAAAGCGG CTTGTACAAG      10980

AGATCCCAAA GCACCACCAT TTGAATATAG AGACTGGCTG ACAAAGATGT CTGGGAAATG      11040

TGATGTTGGT GCTTACATGC TAATGTATAA GGGAGCTAGT CGTACTGAAA CAGTCACATC      11100

TTTTAGAAAA AGAGAAAGTA AGGTGCCAGC CGATCTCTTA AAGCGGGCCT TTGTGAAGAT      11160

GAGTACCAGC CCTGAGGCCT TCCTGACACT CCGCTCACAC TTTGCCGGCT CTCACGCTTT      11220

GATATGCATT AGTCACTGGA TTCCTGGGAT TGGAGATAGA CATCTGAACA ATTTCCTGGT      11280

AAGCATGGAG ACAGGTGGAG TGATTGGAAT CGACTTTGGA CATGCATTTG GATCAGCTAC      11340

TCAGTTTCTG CCGGTCCCTG AGTTGATGCC TTTTCGTCTA ACTCGCCAGT TTATCAATCT      11400

GATGTTACCA ATGAAAGAAA CAGGTGTTAT GTACAGTATC ATGGTGCATG CACTGAGAGC      11460

CTTCCGCTCG CAGTCCAACC TGCTTGCTAA CACCATGGAC GTGTTTGTAA AGGAGCCTTC      11520

CTTCGACTGG AAAAATTTTG AACAGAAAAT GCGGAAAAAA GGAGGATCAT GGATTCAAGA      11580

AATAAATGTA ACTGAAAAAA ATTGGTATCC CCGGCAGAAA ATACATTATG CTAAGAGAAA      11640

GTTAGCTGGT GCCAATCCAG CAGTTATTAC TTGTGATGAG TTACTTCTGG GCCATGAGAA      11700

GGCAGCTGCA TTTGGAGATT ATGTGGCTGT AGCACGAGGA AGTGAAGATC ACAATATCCG      11760

TGCCCAAGAA CTGGAGAGTG ACCTTTCAGA AGAAGCTCAG GTGAAGTGCT TGATTGACCA      11820

GGCAACAGAC CCCAACATCC TTGGCAGAAC CTTGGTAGGA TGGGAGCCCT GGATGTGA       11878

(2) INFORMATION FOR SEQ ID NO:32:

(i) SEQUENCE CHARACTERISTICS:
        (A) LENGTH: 11873 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 32:

GTATATGAGC TCCTAGGAGT ATTAGGTGAA GTTCATCCTA GTGAGATGAT AAGTAATTCA         60
```

```
GAACAACTGT TCCGGGCTTT TCTGGGTGAA CTTAAGTCCC AGATGACATC AACAGTAAGA      120

GAGCCCAAAC TACCTGTTCT GGCAGGGTGT CTGAAGGGAT TGTCATCACT TATGTGTAAC      180

TTCACTAAGT CCATGGAAGA AGATCCCCAG ACTTCAAGGG AGATTTTTGA TTTTGCGTTA      240

AAGGCAATTC GTCCTCAGAT TGATCTGAAG AGATATGCAG TGCCCTTAGC TGGTTTATGC      300

TTATTTACCC TGCATGCATC TCAATTTAGC ACCTGCCTTT TGGAGAACTA CGTTTCTTTG      360

TTTGAAGTGC TGTCAAAATG GTGTGGCCAT ACAAACATAG AATTGAAAAA AGCCGCACAT      420

TCAGCTCTGG AGTCTTTTCT GAAACAGGTT TCTTTTATGG TGGCAAAAGA TGCAGAAAGG      480

CATAAGAATA AGCTGCAGTA CTTTATGGAG CAATTCTATG AATCATCAG GAACATGGAT      540

TCAAATAGCA AGGATTTATC AATTGCAATT CGTGGATATG GACTTTTTGC AGGCCCTTGC      600

AAGGTTATAA ACGCAAAAGA TGTTGACTTC ATGTACGTAG AGCTCATTCA GCGCTGCAAG      660

CAGCTGTTCC TCACCCAGAC AGATACTGTT GATGACCATA TTTACCAGAT GCCCAGTTTC      720

CTCCAATCTA TTGTAAGTGT CTTGCTTTAC CTTGATACAA TTCCTGAGGT GTATACTCCG      780

GTTCTGGAAC ATCTCATGGT GGTACAGATA GACAGCTTCC CACAGTATAG TCCAAAAATG      840

CAGCCGGTGT GTTGTAGAGC CATAGTGAAA CTTTTCCTAG CCTTAGCAGA AAAGGGACCA      900

GTTCTCTGGA ATTGCATTAG TACTGTGGTG CATCAAGGTT TAATTAGAAT ATGTTCTAAA      960

CCAGTCGTCT TTCAAAAGGG TGCTGGGTCT GAATCCGAAG ACTATCATAC ATCAGAGGAA     1020

GCTAGAACTG GCAAATGGAA AATGCCCACA TACAAAGACT ATTTGGATCT TTTTAGATAT     1080

CTCCTGAGCT GTGACCAGAT GATGGATTCT CTTTTAGCAG ATGAAGCATT TCTCTTTGTG     1140

AATTCCTCCC TTCATAGTCT GAATCGTTTG CTGTATGATG AATTTGTAAA ATCAGTTTTG     1200

AAGATTGTTG AGAAATTGGA TCTTACACTA GAAAACAGA ATGTTGGGGA GCAAGAGGAT     1260

GAAACTGAAG CTACTGGTGT TTGGGTGATC CCGACTTCAG ATCCAGCGGC TAACTTGCAC     1320

CCTGCTAAAC CTAAAGATTT TTCAGCTTTC ATTAACCTGG TGGAATTTTG CAGAGAGATT     1380

CTTCCTGAGA AACATGTAGA ATTTTTTGAG CCATGGGTTT ACTCATTTGC GTATGAATTA     1440

ATTTTGCAGT CTACACGGTT ACCACTCATC AGTGTTTTTT ACAAATTGCT TTCTGTTGCT     1500

GTGAGAAATG CCAAGAAAAT GAAGTATTTT GAAGGAGTTG GTCCAAAGAG TCAGAAACAG     1560

TCTCCTGAGG ACCTAGAAAA GTATTCTTGC TTTGCTTTGT TTGCAAAATT TAGTAAAGAG     1620

GTATCAATTA AAATGAAGCA ATACAAAGAT GAACTTTTGG CCTCCTGTTT GACCTTTATT     1680

CTGTCCCTGC CACATGACAT CATTGAACTT GATGTTAGAG CCTACGTTCC TGCATTGCAG     1740

ATGGCTTTTA AACTGGGCCT GAGCTATACT CCATTGGCGG AAGTAGGCCT GAATGCTCTA     1800

GAAGAATGGT CAGGTTACAT CTGCAAACAT GTAATTCAGC CCTATTATAA GGACATTCTA     1860

CCCAGCCTTG ATGGATATCT GAAAACTTCA GTCTTATCAG ATGAGACCAA GAATAGCTGG     1920

CAAGTGTCAG CACTTTCTCG GGCTGCCCAG AAAGGATTTA ATAAAGTTGT GCTAAAGCAT     1980

CTGACAAAGA CAAAGAGCAT TTCATCAAAT GAAGCACTGT CCTTAGAAGA AGTGAGGATT     2040

AGAGTAGTCG GATACTTGGC TCTCTAGGAG ACAAATAAA CAAGAATCTC GTAACAGCTG     2100

CATCATCAGA TGAAATGATG AAGAAGTGTG TGGCATGGGA CAGAGAAAAA AGACTCCGTT     2160

TTGCAGTACC ATTTATGGAG ATGAAGCCTG TCATTTATCT GGATCTATTC CTGCCTCGGG     2220

TCACCGAGTT AGCTCTTTCA GCTAGTGACA GGCAGACTAC AGTTGCAGCC TGTGAACTTT     2280

TACATAGCAT GGTTATGTTT ATGTTGGGAA AAGCCACTCA GATGCCTGAA GATGGTCAGG     2340

GTTCCCCACC CATGTACCAG CTCTATAAGC GAACTTTTCC TGTTTTACTT CGACTTGCAT     2400

GTGATGTAGA TCAGGTGACA AGGCAACTGT ATGAGCCACT AGTTATGCAA CTGATTCACT     2460
```

```
GGTTCACTAA CAACAAGAAA TTTGAAAGTC AGGACACTGT CGCCTTACTA GAAACGATAT    2520

TGGATGGAAT TGTGGACCCT GTTGACAGTA CTTTGAGAGA TTTTTGTGGT CAGTGTATTC    2580

AAGAATTCCT TAAATGGTCC ATTAAGCAGA CGACACCACA GCAGCAGGAA AAAAGTCCAG    2640

TAAATACCAA ATCGCTTTTC AAGCGACTGT ATAGCTTTGC ACTTCATCCG AATGCCTTCA    2700

AGAGGTTGGG AGCATCACTT GCTTTTAATA ATATCTACAG GGAATTCAGG GAAGAAGAGT    2760

CTCTGGTAGA ACAGTTTGTG TTTGAAGCCT TGGTAACGTA TATGGAAAGT CTGGCCTTAG    2820

CACATACAGA TGAGAAATCC TTAGGTACAA TTCAACAATG TTGTGATGCC ATTGATCATC    2880

TCAGTCTTAT CATTGAGAAG AAGCACGTTT CTTTAAACAA AGCAAAAAAA CGACGTTTGC    2940

CACGAGGCTT TCCACCTGCG ACATCACTGT GTTTATTGGA TGTGGTCCAG TGGCTTTTAG    3000

CAAATTGTGG GAGACCCCAG ACAGAATGTC GACACAAATC CATAGAACTC TTTTATAAAT    3060

TTGTTACTTT ATTGCCAGGC AACAAATCCC CTTTTTTATG GCTGAAAGAT ATTATCAAGA    3120

AGAAGATAT TTCCTTTCTC ATAAACACAT TGAGGGCGG GGGAAGTGGT CGGCCGTCAG    3180

GCATCCTTGC TCAGCCAACC CTCTTCCATT TGCAAGGGCC GTTCAGTCTC AGAGCTGCCC    3240

TGCAGTGGAT GGACATGCTT CTGGCAGCAC TGGAGTGCTA CAACACATTC ATTGAAGAGA    3300

AAACTCTGGA AGCACCCAAG GTCCTAGGTA CTGAAACCCA GTCTTCACTT TGGAAAGCGG    3360

TGGCTTTCTT TTTAGAAAGC ATTGCTATGC ATGATATTAT GGCAGCAGAA AAGTACTTTG    3420

GCACTGGGGC AACAGGTAAC AGACCCAGCC ACAAGAAGG AGAAAGATAT AATTATAGCA    3480

AATGTACAAT TGTGGTCCGC ATTATGGAAT TTACCACAAC GCTCCTCAGC ACCTCCCCAG    3540

AAGGCTGGAA GCTGCTTGAG AAGGATGTGT GTAACACAAA CCTTATGAAA CTCTTAGTGA    3600

AAACCCTGTG TGAGCCCTCA AGCATAGGTT TCAACATCGG AGATGTCGCA GTTATGAACT    3660

ATCTTCCCAG TGTTTGTACC AACCTGATGA AAGCACTGAA GAAGTCCCCA TACAAAGACA    3720

TCCTGGAGAT GCACCTCAAG GAAAAGATAA CAGCACAGAG CATTGAAGAG CTCTGTGCAG    3780

TTGACTTGTA TTGCCCTGAT GCTTGCGTGG ACAGGGCCAG GCTGGCTTCT GTCGTGTCAG    3840

CTTGTAAACA ACTTCATAGA GCGGGGGTTT TGTGTGTTAT AATACCATCT CAGTCTGCAG    3900

ATCAGCATCA TTCTATTGGC ACAAAACTTC TTTCCTTGGT TTATAAAAGC ATTGCACCTG    3960

GAGATGAACA ACAGTGCCTT CCTTCACTAG ATCCCAATTG TAAGCGATTG GCCAGTGGAC    4020

TTCTGGAGTT GGCCTTTGCT TTTGGAGGAC TGTGTGAGCA CCTTGTGAGT CTTCTCCTGG    4080

ACACGACAGT GTTGTCATGC CATCCAGAGG AGGGTCCCAG AAAAACATCG TCAGCTTCTC    4140

TCATGGAGAG TATTTTTATA GCTTGTTCTC AGAAACGATC AACACTGAAT TGTTGAAAAA    4200

TCTAGATCTT GCTGTATTGG AGCTCATGAA ATCATCTGTG GATAATCCCA AAATGGTGAG    4260

CAATGTTTTG AATGGTATGT TAGATCAGAG CTTCAGGGAT CGAACCAGTG AGAAACACCA    4320

AGGACTGAAA CTTGCAACTA TAATTCTGCA AAACTGGAAG AAGTGTGATT CATGGTGGGC    4380

CAAAGATTCT GCTCCTGAAA GTAAAATGGC AGTGCTTACC TTGTTGGCAA AAATTTTCCA    4440

GATTGATTCA TCTGTTTGTT TTAATACAAA TCACTGCATG TTCCCTGAAG TCTTTACAAC    4500

ATATGTTAGT CTACTTGCTG ATTCAAAGTT GGACCTGCAT TTAAAGGGCC AAGCTATAAT    4560

TCTTCTTCCA TTCTTCACCA GTCTTACTGG AGGCAGCCTT GAGGACCTTA AGGTTGTTCT    4620

TGAAAACCTC ATCGTTTCTA ATTTTCCTAT GAAATCTGAA GAATTTCCCC CAGGAACTCT    4680

GCAGTACAAT AATTATGTGG ACTGCATGAA GAAGTTTCTA GATGCATTGG AATTATCTAA    4740

AAGCCCTATG TTGTTGCAGT TGATGACAGA AATTCTTTGT CGTGAACAGC AACATGTTAT    4800
```

-continued

```
GGAAGAATTA TTTCAGTCTA CTTTCAAAAA GATTGCCAGA AAGAGTTCAT GTATCACACA      4860

ATTAGGCCTT CTGGAAAGTG TATATAGAAT GTTCAGGAGG GATGACCTGC TTTCAAATAT      4920

CACTCGCCAA GCATTTGTAG ACCGTTCTCT GCTCACTCTG TTGTGGCACT GTAGCTTGAA      4980

TGCTTTGAGG GAATTTTTTA GCAAAATTGT GGTGGAAGCC ATTAATGTGT TGAAGTCCAG      5040

ATTTATAAAG CTGAATGAAT CTGCCTTTGA TACTCAAATC ACCAAGAAGA TGGGCTACTA      5100

TAAGATGTTA GATGTGATGT ATTCTCGTCT TCCAAAAGAT GATGTTCACT CTAAGGAATC      5160

TAAAATTAAT CAAGTTTTCC ATGGCTCATG TATTACAGAA GGAAGTGAAC TTACAAAGAC      5220

ACTTATTAAA TTGTGCTATG ATGCCTTTAC AGAGAACATG GCAGGCGAGA ACCAGTTGCT      5280

GGAGAGGAGA AGACTTTACC ATTGTGCTGC ATACAACTGT GCCATTTCTG TTGTCTGCTG      5340

TGTCTTCAAT GAATTAAAAT TTTACCAAGG TTTTCTGTTT ACTGAAAAAC CAGAAAAGAA      5400

CTTGCTTATT TTTGAAAATC TGATAGACTT GAAGCGCTGC TACACGTTTC CTATAGAAGT      5460

TGAGGTTCCT ATGGAGAGAA AGAAAAAGTA CCTTGAAATT AGAAAGAAG CCAGGGAAGC       5520

AGCAGCAAGT GGGGATTCAG ATGGTCCTCG TTATATATCT TCCTTGTCAT ATTTGGCAGA      5580

CAGTAGCCTG AGTGAGGAAA TGAGTCAATT TGATTTCTCG ACTGGAGTGC AGAGCTATTC      5640

ATATAGTTCC CAAGACCCTA AATCTACCAC TGCTCATTTT CGGAGACAGA AACATAAAGA      5700

GTCCATGATC CAAGATGATA TCCTGGAGTT AGAGATGGAT GAACTCAATC AACACGAATG      5760

TATGGCAACT ATGACTGCTC TGATTAAGCA CATGCAGAGA AATCAGATCC TCCCTAAGGA      5820

AGAAGAGGGT TCAGTGCCAA GAAATCTTCC TCCTTGGATG AAATTTCTTC ATGACAAACT      5880

AGGAAATCCA TCAATATCAT TAAATATCCG TCTCTTCTTA GCCAAGCTTG TTATTAATAC      5940

AGAAGAAGTC TTTCGTCCTT ACGCGAGATA CTGGCTCAGC CCTTTGCTGC AGCTGGTTGT      6000

TTCTGGAAAC AACGGAGGAG AAGGAATTCA CTATATGGTG GTTGAGATAG TGGTTATTAT      6060

TCTTTCATGG ACAGGATTAG CTACTCCTAT AGGTGTCCCT AAAGATGAAG TGTTAGCAAA      6120

TCGATTGCTT CATTTCCTAA TGAACATGTT TTTCATCAAA AAAGAGCTGT GTTTAGACAC      6180

AACCTCGAAA TTATAAAAAC CCTTGTTGAA TGCTGGAAGG ATTGTTTATC CATCCCTTAC      6240

AGGTTAATAT TTGAAAAGTT TTCCAGTACA GATCCTAATT CTAAAGACAA TTCAGTAGGA      6300

ATTCAATTAC TAGGCATTGT AATGGCCAAT AACTTGCCTC CTTATGACCC AAAATGTGGC      6360

ATAGAGAGCA TAAAATACTT TCAAGCTTTG GTCAATAATA TGTCCTTTGT AAGATATAGA      6420

GAGGTATATG CAGCAGCGGC AGAAGTTCTA GGACTTGTTC TTCGATATAT TACTGAGAGA      6480

GAAAATATAC TGGAGGAGTC TGTGTGTGAA CTGGTCATAA AACAGTTGAA GCAACATCAG      6540

AATACGATGG AGGACAAATT TATTGTGTGC TTGAACAAAG CTGTGAAGAA CTTCCCTCCT      6600

CTTGCTGATA GGTTTATGAA CACCGTGTTC TTCCTGCTGC AAAAATTTCA TGGCGTGATG      6660

AAGACTCTCT GTCTGGAGGT GGTACTGTGT CGTGCAGAGG AAATAACAGA TCTATACTTA      6720

CAGTTAAAGA GCAAGGATTT CATTCAAGTC ATGAGACATA GAGATGATGA AAGACAAAAA      6780

GTGTGTTTGG ACATAATTTA TAAGATGATG GCAAGATTGA AACCAGTAGA ACTTCGAGAA      6840

CTTCTGAATC CTGTTGTAGA ATTCATTTCT CATCCTTCTC CAGTGTGTAG GGAACAAATG      6900

TATAACATTC TCATGTGGAT TCATGACAAT TATCGAGATC CAGAAGGTCA GACAGATGAC      6960

GACTCCCAGG AAATATTTAA GTTGGCAAAA GATGTGTTGA TTCAAGGATT GATCGATGAG      7020

AACCCTGGGC TTCAATTAAT TATTCGAAAT TTCTGGAGTC ATGAAACTAG GTTACCTTCA      7080

AATACCTTGG ATCGATTGTT GGCACTAAAT TCCCTATATT CTCCTAAGAT AGAAGCACAC      7140

TTTTTAAGTT TAGCAACAGA TTTTCTGCTT GAAATGACCA GCGTGAGCCC AGATTATTCA      7200
```

```
AACCCTATGT TTGATCATCC TCTGTCAGAA TGCAAATTTC AGGAATATAC TATTGATTCT     7260

GACTGGCGTT TCCGAAGTAC TGTTCTCACT CCAATGTTTA TTGAGACTCA GGCCTCCCAA     7320

AGTGCTCTGC AGACCCGGAC CCAGGAAGGA TCCCTCTCAG CTCGAGGGGT AATGACTGGG     7380

CAGATACGGG CCACACAACA GCAGTATGAT TTCACACCTA CGCAAAATAC AGATGGAAGA     7440

AGCTCTTTCA ATTGGCTGAC TGGGAACAGC ATTGACCCAC TGGTGGATTT TACGGTCTCC     7500

TCCTCATCTG ATTCTTTGTC TTCCTCCTTG CTGTTTGCTC ACAAGAGGAG TGAAAAATCA     7560

CAGAGAGGAC CCTTGAAGTC AGTAGGACCT GATTTTGGGA AAAAAAGGCT GGGCCTTCCA     7620

GGGGATGAGG TGGATAACAA AGCAAAAGGT ACAGACAATC GGGCGGAAAT ATTAAGATTA     7680

CGGAGACGAT TTTTAAAGGA CCGAGAAAAG CTCAGTTTGA TTTATGCCAG AAAAGGTGTT     7740

GCTGAACAAA AACGAGAGAA GGAGATCAAG AGTGAGTTAA AAATGAAGCA CGATGCCCAA     7800

GTCATTTTGT ACAGAAGTTA CCGTCAAGGA GACCTTCCTG ACATTCAGAT TAAATACAGC     7860

AGCCTGATCA CTCCCTTGCA AGCTGTGGCC CAGAGAGACC CAATAATTGC AAAGCAGCTC     7920

TTTGGCAGCT TGTTTTCTGG AATTATAAAA GAGATGGATA AATATAAGAC CATGTCTGAA     7980

AAAAACAACA TTACTCAGAA GTTGCTCCAG GACTTCAATA ATTTTCTTAA CACCACTGTC     8040

TCTTTCTTTC CACCTTTCAT CTCCTGTATC CAGGAAATTA GTTGCCAACA CGCAGACTTG     8100

CTGAGCCTCG ACCCAGCTTC TGTCAGTGCC AGCTGCCTGG CCAGTCTGCA GCAGCCTGTA     8160

GGCGTCCGCC TTCTGGAGGA GGCCTTGCTC CACTGCTGCC TGAAGAGCCA CCTGCCAAGC     8220

GAGTTCGAGG GAGACCCTGT CTCTACCCTG ATTTTGTCAG ATGGATGGAA CTTGCTAAAC     8280

TGTATAGATC AATTGGAGAA TATGCACATCC TCCGTGGGAT TTTTAATAGT GAGATAGGAA     8340

CAAAGCAAGT CACTCAGAAT GCATTATTAG CAGAAGCAAG AAATGATTAT TCTGAAGCCG     8400

TTAAGCAGTA TAATGAGGCT CTCAATAAAC AAGACTGGGT AGATGGTGAG CCTATGGAAG     8460

CTGAGAAGGA TTTTTGGGAA CTTGCATCCC TTGACTGTTA TAACCAACTT GCTGAGTGGA     8520

AATCACTGGC ATACTGTTCT ACAGTCAGTG TTGACAGTGC GAACCCTCCA GATTTAAATA     8580

AAATGTGGAA TGAACCATTT TATCAGGAGA CCTATCTACC TTACATGATC CGCAGCAAGC     8640

TGAAGCTACT TCTGCAAGGT GAGGGAGACC AGTCCCTGCT GACATTTATT GATGAAGCTG     8700

TGAGCAAGGA GCTCCAGAAG GTCCTCGTAG AGCTTCATTA CAGTCAGGAA TTGAGTCTCC     8760

TTTATATCCT ACAAGATGAC GTCGACAGAG CCAAATATTA TATTGAAAAT TGCATTCGGA     8820

TTTTCATGCA GAGCTATTCT AGTATTGATG TCCTTTTAGA GAGAAGTAGA CTCACCAAAT     8880

TGCAATCTCT ACAGGCTTTA ATAGAAATTC AGGAGTTCAT CAGCTTTATA AGGAAACAAG     8940

GTAATTTATC AAATTCCCCT TAAGAGACTT CTAAAAACCT GGACAAACAG ATATCCGGAT     9000

GCTAAAATGG ACCCAATGAA CATCTGGGAT GACATCATCA CAAATCGATG TTTCTTTCTC     9060

AGCAAAATAG AAGAAAAACT GACTATTCCT CCAGATGATC ATAGTATGAA CACAGATGGA     9120

GATGAAGATT CCAGTGACAG AATGAAAGTG CAGGAGCAGG AGGAAGATAT TTATTCTCTG     9180

ATTAAGAGTG GTAAGTTTTC CATGAAAATG AAGATGATAG AAAGTGCAAG GAAACAGAAA     9240

AATTTCTCAC TAGCCATGAA ACTATTAAAG GAGCTTCATA AGAGTCAAA AACAAGAGAT     9300

GACTGGCTGG TGAAATGGGT GCAGAGCTAC TGTCGACTCA GTCACAGCCG GAGCCAGACC     9360

CAGAATCGTC CTGAGCAGAT CCTTACTGTG TTGAAAACAG TCTCTTTGTT GGATGAGAAC     9420

ACATCAAGCT ACTTAAGCAA AAATATTCCA GTTTCCCGTG ACCACAACAT TCTCTTGGGT     9480

ACAACTTACA GGATCATAGC TAATGCTCTC AGCAGTGATC CAACTTGCCT TGCTGAAATC     9540
```

```
GGGGAAAGCA AGGCTAGAAG AATCTTGGAG CTGTCTGGAT CCAGTTTAGA GAATGCAGAA      9600
GAGGTGATCG CAGGTCTATA CCAGAGAGTG TTGCATCACC TTTCTGAGGC CGTGCGGATT      9660
GCAGAGGAGG AGGCCCAGCC TTTCACTAGA GGCCAGGAAC CTGCAGTTGG GGTGATAGAT      9720
GCTTACATGA CACTGGTGGA TTTCTGTGAC CAGCAGCTCC GCAAGGAGGA AGAGAGTTCA      9780
TCAGTTACTG AGTCTGTACA ACTGCAGATG TATCCAGCCC TTGTGGTGGA CAAAATGTTA      9840
AAAGCTTTAA GACTCGATTC CAATGAAGCC AGGCTGAAGT TTCCCAGACT ACTGCAGATT      9900
ATAGAACGGT ATCCAGAGGA GACCCTGAGC CTAATGACCA AAGAGATTTC TTCCATTCCT      9960
TGCTGGCAGT TCATTGGCTG GATCAGCCAC ATGGTGGCCT TACTGGACAA AGAGGAAGCT     10020
GTCGCTGTCC ATCGCACAGT GGAAGAGATT GCTGATAACT ATCCACAGGC GATGGTCTAC     10080
CCATTTATAA TAAGCAGTGA AAGCTATTCC TTCAAAGATA CTTCTACTGG TTATAAGAAT     10140
AAGGAGTTTG TGGAAAGGAT TAAAATTAAG TTGGATCAAG GAGGAGTGAT TCAAGATTTT     10200
ATTAATGCCC TAGAACAGCT CTCTCATCCT GAAATGCTCT TAAGGACTGG ACTGATGATA     10260
TCAAAGTTGA ACTTGAAAAA AACCCTGTAA ATAGAAAAAA CATTGAAAAG ATGTATGAAA     10320
AAATGTATGC AACCTTGGGA GACCCACAGG CTCCAGGTCT TGGGGCTTTT CGAAGAAGGT     10380
GTATTCAGGG TTTTGAAAAA GAATTTGATA AACACTTTGG GAGAGGAGGT TCTAAGCTAC     10440
CTGGAATGAA ATCCCGTGAA TTCAGTGATA TTACCAACTC ACTATTTTCA AAAATGTGCG     10500
AAGTCTCAAA GCCACCTGGG AATCTGAAAG AATGCTCGCC CTGGATGAGT GACTTCAAAG     10560
TAGAATTTTT GAGAAGTGAA CTGGAGATTC CTGGTCAGTA TGATGGCAAG GGAAAACCAG     10620
TGCCAGAATA CCATGCACGA ATTGCTGGGT TTGATGAGCG GATAAAAGTA ATGGCTTCTA     10680
TGAGAAAACC AAAGCGTATC ATCATCCGAG GCCATGATGA GAGAGTAC CCTTTCCTTG     10740
TGAAGGGAGG TGAAGATCTG AGGCAGGACC AACGCATCGA GCAGCTCTTC GAGGTCATGA     10800
ATGTCATCCT TTCCCAAGAT GCTACCTGTA GTCAGAGAAG CATGCAGCTA AAGACATACC     10860
AGGTCATACC CATGACCTCC AGATTAGGAC TAATTGAATG GATTGAAAAT ACTTTTACCT     10920
TGAAGGAACT TCTTTTGAGT AACATGTCAC AAGAGGAGAA AGCGGCTTGT ACAAGAGATC     10980
CCAAAGCACC ACCATTTGAA TATAGAGACT GGCTGACAAA GATGTCTGGG AAATGTGATG     11040
TTGGTGCTTA CATGCTAATG TATAAGGGAG CTAGTCGTAC TGAAACAGTC ACATCTTTTA     11100
GAAAAAGAGA AAGTAAGGTG CCAGCCGATC TCTTAAAGCG GGCCTTTGTG AAGATGAGTA     11160
CCAGCCCTGA GGCCTTCCTG ACACTCCGCT CACACTTTGC CGGCTCTCAC GCTTTGATAT     11220
GCATTAGTCA CTGGATTCCT GGGATTGGAG ATAGACATCT GAACAATTTC CTGGTAAGCA     11280
TGGAGACAGG TGGAGTGATT GGAATCGACT TTGGACATGC ATTTGGATCA GCTACTCAGT     11340
TTCTGCCGGT CCCTGAGTTG ATGCCTTTTC GTCTAACTCG CCAGTTTATC AATCTGATGT     11400
TACCAATGAA AGAAACAGGT GTTATGTACA GTATCATGGT GCATGCACTG AGAGCCTTCC     11460
GCTCGCAGTC CAACCTGCTT GCTAACACCA TGGACGTGTT TGTAAAGGAG CCTTCCTTCG     11520
ACTGGAAAAA TTTTGAACAG AAAATGCGGA AAAAGGAGG ATCATGGATT CAAGAAATAA     11580
ATGTAACTGA AAAAAATTGG TATCCCCGGC AGAAAATACA TTATGCTAAG AGAAAGTTAG     11640
CTGGTGCCAA TCCAGCAGTT ATTACTTGTG ATGAGTTACT TCTGGGCCAT GAGAAGGCAG     11700
CTGCATTTGG AGATTATGTG GCTGTAGCAC GAGGAAGTGA AGATCACAAT ATCCGTGCCC     11760
AAGAACTGGA GAGTGACCTT TCAGAAGAAG CTCAGGTGAA GTGCTTGATT GACCAGGCAA     11820
CAGACCCCAA CATCCTTGGC AGAACCTTGG TAGGATGGGA GCCCTGGATG TGA           11873
```

GENETIC TEST FOR EQUINE SEVERE COMBINED IMMUNODEFICIENCY DISEASE

CROSS-REFERENCE TO RELATED APPLICATION

This is a continuation of application Ser. No. 08/970,269 filed Nov. 14, 1997, U.S. Pat. No. 5,976,803.

This application claims the benefit of provisional application No. 60/031,261, filed Nov. 15, 1996.

FEDERAL FUNDING LEGEND

This invention was created using funds under NIH grant No. AI32600. The U.S. government, has rights in this invention.

BACKGROUND OF THE INVENTION

1. Field of the Invention

The present invention relates generally to the fields of molecular genetics and veterinary medicine. More specifically, the present invention relates to the mutation of a DNA-dependent protein kinase protein which results in equine severe combined immunodeficiency and a diagnostic test to identify carriers of the mutation.

2. Description of the Related Art

V(D)J rearrangement is the molecular mechanism b y which distinct gene segments (V, D, and J) are joined to form the coding sequences of immunoglobulin (Ig) and T cell receptor (TCR) variable regions. The rearrangement process is targeted by simple DNA sequence elements (recombination signal sequences, RSS) found immediately adjacent to all functional immune receptor gene segments and involves two double-stranded DNA cuts and subsequent re-ligations. This process results in the formation of two new DNA joints; coding joints which contain the coding information, and signal joints which contain the two recombination signal sequences. V(D)J rearrangement is mediated by a lymphoid-specific endonuclease (the RAG 1 and RAG 2 proteins) and ubiquitously expressed components of the double strand break repair pathway. The centrality of V(D)J recombination to the development of the vertebrate immune system is evident in situations where the process is defective.

Defective V(D)J recombination results in a complete block of B and T cell lymphopoiesis and the disease severe combined immunodeficiency (SCID). The first example of defective V(D)J recombination was described in 1983 by Bosma and colleagues, relating to a spontaneous mutation in mice that results in severe combined immunodeficiency (C.B-17 mice). In severe combined immunodeficiency mice, the only step in V(D)J recombination that appears to be impaired is resolution of coding ends. Instead of being resolved into functional immune receptors, cleaved coding ends accumulate abnormally in developing severe combined immunodeficiency lymphocytes. However, cleaved signal ends are resolved at a similar rate as in wild type lymphocytes in mice.

In 1990, it was demonstrated that the defect in severe combined immunodeficiency mice not only impairs V(D)J recombination, but also affects the more general process of double strand break repair (DSBR). This observation was the first to link V(D)J recombination and double strand break repair. In recent years it has been shown that at least four factors are required for both V(D)J recombination and double strand break repair: the Ku heterodimer, DNA-dependent protein kinase$_{catalytic}$ subunit (PK$_{CS}$), XRCC4, and XRCC6.

Recently, defective DNA-dependent protein kinase$_{catalytic}$ subunit has been identified as the determinative factor in C.B-17 severe combined immunodeficiency mice. The DNA-end binding Ku heterodimer interacts with DNA-dependent protein kinase$_{catalytic}$ subunit to generate a protein kinase (DNA-PK) that is dependent on linear DNA for activation (i.e., DNA-dependent protein kinase). DNA-dependent protein kinase$_{catalytic}$ subunit is related to the phosphatidylinositol 3-kinase family whose members function in a variety of roles such as signal transduction by phosphorylation of phospholipids, control of cell cycle progression, and maintenance of telomere length.

Although DNA-dependent protein kinase$_{catalytic}$ subunit has been implicated in a variety of different processes, its precise role is unclear. The factor defective in the double strand break repair mutant CHO cell line XRI. In sum, defects in either the lymphocyte specific components of the V(D)J recombinase (RAG 1 -/- mice, RAG 2-/- mice, RAG-deficient children) or any one of these double strand break repair factors (C.B-17 severe combined immunodeficiency mice, Arabian severe combined immunodeficiency foals, Ku80 -/- mice) results in B and T lymphocyte development being blocked and similar phenotypes are observed.

The occurrence of severe combined immunodeficiency in Arabian foals was initially reported in 1973 by McGuire and Poppie. Recently, it was demonstrated that severe combined immunodeficiency in Arabian foals is explained by a severe block in the generation of specific immune receptors because of defective V(D)J rearrangement. As is the case in murine severe combined immunodeficiency, equine severe combined immunodeficiency cells are hypersensitive to DNA damage because of severely diminished levels of DNA-dependent protein kinase$_{catalytic}$ subunit. However, these two genetic defects have important mechanistic differences. Unlike severe combined immunodeficiency mice that are preferentially defective in coding resolution, severe combined immunodeficiency foals are defective in both coding and signal resolution.

The prior art is deficient in the lack of effective means of determining the presence of the genetic detemrinant for equine severe combined immunodeficiency in an animal of interest. The present invention fulfills this longstanding need and desire in the art.

SUMMARY OF THE INVENTION

Previously, the mechanistic defect responsible for the autosomal recessive disease severe combined immunodeficiency (SCID) in Arabian foals was reported to involve a V(D)J recombination. As with the murine counterpart of SCID, cells from SCID foals have severely depressed levels of DNA dependent protein kinase activity because of a deficiency in the catalytic subunit of the enzyme (DNA-dependent protein kinase$_{catalytic}$ subunit). However, unlike SCID mice which are specifically impaired in their ability to resolve immune receptor coding joints, SCID foals are incapable of resolving both coding and signal ends.

The present invention presents the genotypic analysis of the defective DNA-dependent protein kinase$_{catalytic}$ subunit allele in Arabian horses and provides the sequence for the normal and mutant DNA-dependent protein kinase$_{catalytic}$ subunit gene and protein. These results formally establish the importance of the DNA-dependent protein kinase$_{catalytic}$ subunit in signal end resolution during V(D)J rearrangement.

In the equine severe combined immunodeficiency mutation, a frameshift deletion prematurely truncates the DNA-dependent protein kinase$_{catalytic}$ subunit at amino acid 3160 of the normal 4127 amino acid polypeptide. This truncation apparently results in a kinase negative version of the protein. In contrast, the DNA-dependent protein kinase-$_{catalytic}$ subunit mutation responsible for severe combined immunodeficiency in C.B-17 mice may not completely ablate kinase activity. Thus, one explanation for the mechanistic differences in these two DNA-dependent protein kinase$_{catalytic}$ subunit defects models is that low levels of DNA-dependent kinase (likely present in severe combined immunodeficiency mice) can support signal end resolution, but normal levels are required to support coding resolution.

In one embodiment of the present invention, there is provided a composition of matter comprising an isolated DNA molecule encoding a DNA-dependent protein kinase-$_{catalytic}$ subunit protein in Arabian horses having a sequence shown in SEQ ID No. 28.

In another embodiment of the present invention, there is provided a composition of matter comprising an oligonucleotide having a sequence selected from the group of SEQ ID Nos. 24 and 25. These oligonucleotides precisely span the SCID-determinant region of the DNA-PK$_{CS}$ gene, and are diagnostic for the normal and SCID alleles, respectively.

In yet another aspect of the present invention, there is provided an isolated DNA sequence having the sequence shown in SEQ ID No: 26 or SEQ ID No: 27.

In yet another aspect of the present invention, there is provided a method of identifying an Arabian horse that is a carrier of equine severe combined immunodeficiency, comprising the step of: determining whether said horse has a mutation in a SCID determinant region of a DNA-dependent protein kinase$_{catalytic}$ subunit gene. In one embodiment of this aspect of the present invention, there is provided a method of identifying an Arabian horse that is a carrier of equine severe combined immunodeficiency which further includes the step of screening a sample of DNA from said horse with an oligonucleotide having the sequence SEQ ID No. 25. In yet another embodiment of this aspect of the invention, there is provided an additional step wherein a second sample of DNA from said horse is screened with an oligonucleotide having the sequence SEQ ID No. 24. In addition, the determining step may include the step of amplifying said DNA-dependent protein kinase$_{catalytic}$ subunit gene.

A particular aspect of the present invention provides a method of determining whether an Arabian horse has a normal allele for a DNA-dependent protein kinase$_{catalytic}$ subunit gene, a SCID allele for a DNA-dependent protein kinase$_{catalytic}$ subunit gene, or both, comprising the steps of: obtaining samples from candidate horses; treating said samples obtained from candidate horses to expose nucleic acids; incubating said sample nucleic acids with a labeled oligonucleotide selected from the group of SEQ ID No. 24 and SEQ ID No. 25, under conditions and for a time sufficient for said oligonucleotides to hybridize to a complementary sequence in said sample nucleic acid, if present; eliminating any unhybridized oligonucleotides; and detecting the presence or absence of said hybridized oligonucleotides, wherein a presence of hybridized oligonucleotide having a sequence SEQ ID No. 24 indicates the presence of a normal allele for a DNA-dependent protein kinase$_{catalytic}$ subunit gene, wherein a presence of hybridized oligonucleotide having a sequence SEQ ID No. 25 indicates a presence of a SCID allele for a DNA-dependent protein kinase$_{catalytic}$ subunit gene, and wherein a presence of hybridized oligonucleotides having a sequence SEQ ID No. 24 and SEQ ID No. 25 indicates a presence of both a normal allele for a DNA-dependent protein kinase$_{catalytic}$ subunit gene and a presence of a SCID allele for a DNA-dependent protein kinase$_{catalytic}$ subunit gene. An embodiment of this aspect of the present invention includes a DNA amplification step being performed on a SCID-determinant region in a DNA-dependent protein kinase$_{catalytic}$ subunit gene between said obtaining step and said treating step.

An additional aspect of the present invention includes a n isolated protein encoding a normal DNA-dependent protein kinase$_{catalytic}$ subunit protein having a sequence SEQ ID No. 29 and an isolated protein encoding a mutant DNA-dependent protein kinase$_{catalytic}$ subunit protein having a sequence SEQ ID No. 30. The present invention also is drawn to an a plasmid containing a DNA encoding a DNA-dependent protein kinase$_{catalytic}$ subunit protein (SEQ ID No. 29) and regulatory elements necessary for expression of the DNA in the cell, said plasmid adapted for expression in a recombinant cell, and a plasmid containing the DNA of SEQ ID No. 28 and regulatory elements necessary for expression of said DNA in said cell, said plasmid adapted for expression in a recombinant cell.

A further aspect of the present invention provides a method of identifying an Arabian horse that is a carrier for equine severe combined immunodeficiency, comprising the step of: determining whether said horse has a gene that encodes a protein having a sequence SEQ ID No. 30, wherein a presence of said gene indicates a horse that is a carrier for equine severe combined immunodeficiency.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can b e understood in detail, more particular descriptions of the invention briefly summarized above may be had by reference to certain embodiments which are illustrated in the appended drawings. These drawings form a part of the specification. It is to be noted, however, that the appended drawings illustrate preferred embodiments of the invention and therefore are not to be considered limiting in their scope.

FIG. 2 presents the deduced amino acid sequence comparison of the equine DNA-dependent protein kinase$_{catalytic}$ subunit transcript (derived from the 0176 cell line) compared to the human counterpart. Comparison starts at amino acid 180 of the human sequence. Potential DNA-PK autophosphorylation sites and Leucine zipper motifs have been underlined. The conserved protein kinase motifs are shown in bold.

FIG. 4B shows genomic DNA from cell lines 0176 and 1821 amplified with oligonucleotides 392/405. Amplified fragments were cloned and sequenced with primer 392. Sequence analysis of the two clones reveals a five nucleotide deletion in the 1821 genomic fragment.

DETAILED DESCRIPTION OF THE INVENTION

Figure 1:
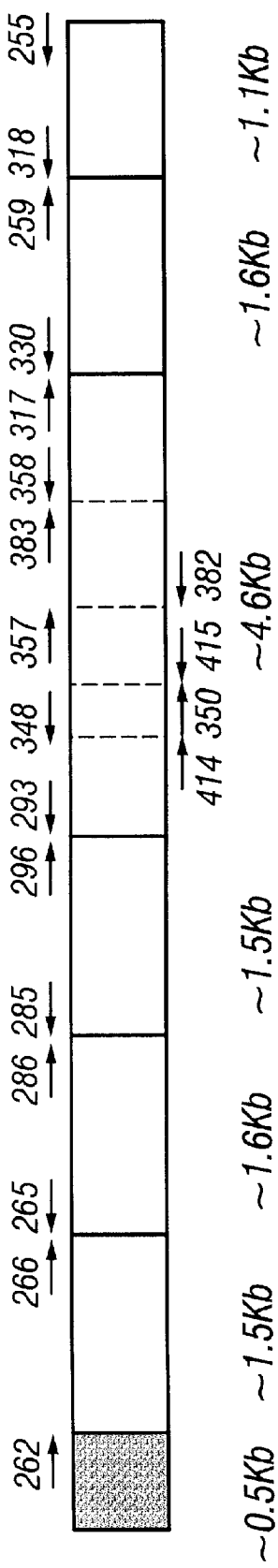
FIG. 1 is a diagramatic representation of the DNA-dependent protein kinase$_{catalytic}$ subunit transcript. Arrows and numbers denote positions of oligonucleotide primers used to amplify the equine transcripts. Each box represents an overlapping cDNA fragment derived from the 0176 and 1821 cell lines. Cloning the fragment from nucleotide 4950 to 9539 from the 1821 cell line was unsuccessful. Thus, the sequence of the 0176 transcript was determined for this region, and then four separate fragments were cloned and sequenced (denoted by dotted lines) from the 1821 cell line.

The following abbreviations may be used herein: Abbreviations: DSBR, double strand break repair; DNA-PK, DNA dependent protein kinase; DNA-PK$_{CS}$, catalytic subunit of DNA dependent protein kinase; V(D)J, Variable (Diversity) Joining; RAG, recombination activating gene.

In accordance with the present invention there may b e employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

Therefore, if appearing herein, the following terms shall have the definitions set out below.

The amino acids described herein are preferred to be in the "L" isomeric form. However, residues in the "D" isomeric form can be substituted for any L-amino acid residue as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomeclature, *J Biol. Chem.*, 243:3552–59 (1969), abbreviations for amino acid residues are shown in the following Table of Correspondence:

| TABLE OF CORRESPONDENCE | | |
|---|---|---|
| SYMBOL 1-Letter | 3-Letter | AMINO ACID |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an automous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl)

terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined b y mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide. The present invention is drawn to screening oligonucleotides having the sequence SEQ ID 24 or 25, or a portion of these oligonucleotides, which span the SCID-determinant portion of the DNA-dependent protein kinase$_{catalytic}$ subunit gene.

The term "primer" as used herein refers to a n oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides. In the present invention, primers used for amplification of the SCID-determinant region of DNA-dependent protein kinase$_{catalytic}$ subunit have the sequence of SEQ ID Nos. 22 and 23.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or a common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "normal allele" refers to the gene that codes for the wildtype DNA-PK$_{CS}$, and does not cause SCID. Specifically, the normal allele does not have the 5 base pair deletion present corresponding to nucleotide 9,454 of the 12,381 nucleotide coding sequence of the human transcript, and has the sequence AGGTAATTTAT-CATCTCA (SEQ. ID No. 24) at the SCID-determinant region.

As used herein, the term "SCID allele" refers to the gene that codes for the mutant DNA-dependent protein kinase-$_{catalytic}$ subunit protein, and causes equine SCID. Specifically, the SCID allele has the 5 base pair deletion present corresponding to nucleotide 9,454 of the 12,381 nucleotide coding sequence of the human transcript, and has the sequence AGGTAATTTATCAAATTC (SEQ. ID No. 25) at the SCID-determinant region of the DNA-dependent protein kinase$_{catalytic}$ subunit gene. The 5 base pair deletion results in premature termination of the DNA-dependent protein kinase$_{catalytic}$ subunit protein at amino acid 3160 of the 4127 amino acid polypeptide.

As used herein, the term "SCID determinant region" of the DNA-dependent protein kinase$_{catalytic}$ subunit gene refers to region of the DNA-dependent protein kinase$_{catalytic}$ subunit gene having the 5 base pair deletion in SCID-carrier animals which corresponds to nucleotide 9,454 of the 12,381 nucleotide coding sequence of the human transcript. The SCID determinant region in normal individuals has the sequence AGGTAATTTATCATCTCA (SEQ. ID No. 24) in normal alleles and the sequence AGGTAATTTAT-CAAATTC (SEQ. ID No. 25) in SCID alleles. The difference in the sequences between the normal and SCID alleles in the SCID-determinant region results in premature termination of the DNA-dependent protein kinase$_{catalytic}$ subunit protein at amino acid 3160 of the 4127 amino acid polypeptide in the SCID-causing DNA-dependent protein kinase-$_{catalytic}$ subunit protein.

As used herein, the term "carrier" refers to an animal heterozygous for a recessive genetic trait. Carriers are unaffected but have the potential to pass the trait on to their offspring.

The present invention describes the DNA-dependent protein kinase$_{catalytic}$ subunit gene in both normal and severe combined immunodeficiency horses. In SCID horses, a 5 base pair deletion is present corresponding to nucleotide 9,454 of the 12,381 nucleotide coding sequence of the human transcript. This 5 base pair deletion results in premature termination of the DNA-dependent protein kinase-$_{catalytic}$ subunit protein at amino acid 3160 of the 4127 amino acid polypeptide. Unlike the murine DNA-dependent protein kinase$_{catalytic}$ subunit mutation (which deletes the C terminal 80 amino acids of the protein), the equine DNA-dependent protein kinase$_{catalytic}$ subunit mutation most likely ablates DNA-dependent protein kinase activity completely. Thus, equine DNA-dependent protein kinase$_{catalytic}$ subunit plays a role in both signal end resolution and coding end resolution. Asymmetry of signal versus coding ligation in severe combined immunodeficiency mice (lacking in severe combined immunodeficiency foals) may be explained b y minimal DNA dependent protein kinase activity in severe combined immunodeficiency mice.

The following diagnostic strategy for differentiating SCID heterozygotes, homozygotes, and normal horses may be used by a person having ordinary skill in this art given the teachings of the present invention. Using the sequence information obtained of the DNA-PK$_{CS}$ transcripts from normal and SCID foals, a simple diagnostic test for determining genotype of a given animal is straightforward to one skilled in the art of molecular biology. Since the present invention has identified precisely the same mutation in eight SCID animals and in two carriers, it is likely that this mutation is responsible for the majority of SCID cases in Arabian horses. This mutation is likely the result of a breeding bottleneck and a genetic founder effect.

A desirable diagnostic test would take advantage of the genomic sequence surrounding the mutation. Such a test may use a strategy of amplifying the region of interest from DNA derived from the animal to be tested. Probes spanning the unmutated sequence or mutated sequence will, under the appropriate conditions, hybridize specifically. Thus, DNA from a normal animal which is not a carrier would hybridize with the probe based on the unmutated sequence, but would not hybridize with the probe based on the mutated sequence. DNA from a heterozygous, carrier animal will hybridize with both probes. DNA from a SCID animal will only hybridize with the probe based on the mutated sequence.

In one method of the present invention, there is provided a method of identifying an Arabian horse that is a carrier of equine severe combined immunodeficiency, comprising the step of: determining whether said horse has a mutation in a SCID determinant region of a DNA-dependent protein kinase$_{catalytic}$ subunit gene. In a prefered embodiment of this method, there is provided a method of determining whether an Arabian horse has a normal allele for a DNA-dependent protein kinase$_{catalytic}$ subunit gene, a SCID allele for a DNA-dependent protein kinase$_{catalytic}$ subunit gene, or both, comprising the steps of: obtaining samples from candidate horses; treating said samples obtained from candidate horses to expose nucleic acids; incubating said sample nucleic acids with a labeled oligonucleotide selected from the group of SEQ ID No. 24 and SEQ ID No. 25, under conditions and for a time sufficient for said oligonucleotides to hybridize to a complementary sequence in said sample nucleic acid, if present; eliminating any unhybridized oligonucleotides; and detecting the presence or absence of said hybridized oligonucleotides, wherein a presence of hybridized oligonucleotide having a sequence SEQ ID No. 24 indicates the presence of a normal allele for a DNA-dependent protein kinase$_{catalytic}$ subunit gene, wherein a presence of hybridized oligonucleotide having a sequence SEQ ID No. 25 indicates a presence of a SCID allele for a DNA-dependent protein kinase$_{catalytic}$ subunit gene, and wherein a presence of hybridized oligonucleotides having a sequence SEQ ID No. 24 and SEQ ID No. 25 indicates a presence of both a normal allele for a DNA-dependent protein kinase$_{catalytic}$ subunit gene and a presence of a SCID allele for a DNA-dependent protein kinase$_{catalytic}$ subunit gene. An embodiment of this aspect of the present invention includes a DNA amplification step being performed on a SCID-determinant region in a DNA-dependent protein kinase$_{catalytic}$ subunit gene between said obtaining step and said treating step.

In another method of the present invention, there is provided a method of determining whether an Arabian horse has a normal allele for a DNA-dependent protein kinase-$_{catalytic}$ subunit gene, a SCID allele for a DNA-dependent protein kinase$_{catalytic}$ subunit gene, or both, comprising the steps of: obtaining samples from candidate horses; treating said samples obtained from candidate horses to expose nucleic acids; incubating said sample nucleic acids with a labeled oligonucleotide selected from the group of SEQ ID No. 26 and SEQ ID No. 27, or portions thereof, under conditions and for a time sufficient for said oligonucleotides to hybridize to a complementary sequence in said sample nucleic acid, if present; eliminating any unhybridized oligonucleotides; and detecting a presence or absence of said hybridized oligonucleotides; wherein a presence of hybridized oligonucleotide having a sequence SEQ ID No. 27 indicates a presence of a normal allele for a DNA-dependent protein kinase$_{catalytic}$ subunit gene, wherein a presence of hybridized oligonucleotide having a sequence SEQ ID No. 26 indicates a presence of a SCID allele for a DNA-dependent protein kinase$_{catalytic}$ subunit gene, and wherein a presence of hybridized oligonucleotides having a sequence SEQ ID No. 26 and SEQ ID No. 27 indicates a presence of both a normal allele for a DNA-dependent protein kinase-$_{catalytic}$ subunit gene and a presence of a SCID allele for a DNA-dependent protein kinase$_{catalytic}$ subunit gene.

In addition, several alternative amplification strategies are envisioned. Since equine SCID is the result of a 5 nucleotide deletion, primers can be designed easily which selectively amplify the mutated or the normal allele. Further, it is well within the expertise of the skilled artisan that primers can be designed such that products amplified from the mutated and normal alleles have unique sizes or unique restriction endonuclease sites to allow for rapid diagnosis. The main point being that no matter what molecular technique is used, all strategies involve detecting the portion of the DNA-dependent protein kinase$_{catalytic}$ subunit gene in which the 5-nucleotide deletion occurs in the mutated DNA-dependent protein kinase$_{catalytic}$ subunit gene. The following examples are given for the purpose of illustrating various embodiments of the invention and are not meant to limit the present invention in any fashion.

EXAMPLE 1

Cell Lines

The 0176 fibroblast cell line was derived from a normal (non-Arabian) horse. The 1821 fibroblast cell line was derived from a homozygous severe combined immunodeficiency foal. All cultures were carried out in DMEM medium (GIBCO Laboratories, Grand Island, N.Y.) supplemented with 10% FCS.

EXAMPLE 2

RT-PCR

RT-PCR was performed on RNA isolated from the 0176 and 1821 cell lines. RNA was isolated using RNAzol (Biotecx; Houston, Tex.). After ethanol precipitation, cDNA was prepared using Superscript (reverse transcriptase); PCR was performed using Elongase (Taq polymerase) according to the manufacturers recommendations (Gibco BRL, Gaithersburg, Md.). Transcripts amplified in this manner were subcloned and sequenced using standard techniques.

EXAMPLE 3

Oligonucleoties

Position of amplification primers is illustrated in FIG. 1. Sequences of oligonucleotides used were as follows:

262: GTATATGAGCTCCTAGG (SEQ. ID No.1);
265: GGGAGAATCTCTCTGCAA (SEQ. ID No.2);
    TCAGGAGVRC ATCAGCTT (SEQ ID No.3)
266: GATCCAGCGGCTAACTTG (SEQ. ID No.4);
285: CATGTGCTAAGGCCAGAC (SEQ. ID No.5);
286: TCTACAGGGAATTCAGGG (SEQ. ID No.6);
293: CACCATGAATCACACTTC (SEQ. ID No.7);
296: CACCAAGGACTGAAACTT (SEQ. ID No. 8);
330: GCACTTTCATTCTGTCAC (SEQ. ID No.9);
317: ATTCATGACCTCGAAGAG (SEQ. ID No. 10);
318: TGGACAAACAGATATCCAG (SEQ. ID No. 11);
259: ATCGCCGGGTTTGATGAGCGGGTG (SEQ. ID No.12);
255: CAGACCTCACATCCAGGGCTCCCA (SEQ. ID No. 13);
348: GAGACGGATATTTAATG (SEQ. ID No. 14);
414: GGAGTGCAGAGCTATTCAT (SEQ. ID No.15);
415: GCAATCGATTTGCTAACAC (SEQ. ID No.16);
350: GTCCCTAAAGATGAAGTG (SEQ. ID No. 17);
382: GTCATGAATCCACATGAG (SEQ. ID No. 18);
357: TTCTTCCTGCTGCCAAAA (SEQ. ID No. 19);
358: CTTTGTTCCTATCTCACT (SEQ. ID No. 20);
383: AGACTTGCTGAGCCTCGA (SEQ. ID No. 21);
405: TTCCTGTTGCAAAAGGAG (SEQ. ID No. 22);
392: TTTGTGATGATGTCATCC (SEQ. ID No. 23);
N: AGGTAATTTATCATCTCA (SEQ. ID No. 24);
S: AGGTAATTTATCAAATTC (SEQ. ID No. 25).

EXAMPLE 4

Genomic PCR

Total genomic DNA was analyzed from spleen, bone marrow, peripheral blood or fibroblast cell lines as indicated. DNA was isolated using ABI DNA lysis buffer (Applied Biosystems, Foster City, Calif.). Oligonucletide primers 405 and 392 (SEQ ID Nos. 22 and 23) were used to screen for the mutant severe combined immunodeficiency allele. Amplification conditions were 94° C. for 30 seconds, 55° C. for 90 seconds, and 68° C. for five minutes. Amplified DNA was loaded onto 1.5% duplicate agarose gels for Southern filter hybridization analysis. After electrophoresis, DNA was transferred in 0.4N NaOH onto nylon membranes (Zeta-probe, Biorad, Hercules, Calif.). Southern filter hybridization was done in 6×SSC, 0.5% SDS, and 5×Denhardts at 42° C. $^{32}$P-end labeled oligonucleotides specific for the normal and severe combined immunodeficiency alleles were used as hybridization probes. Filters were washed in 6X SSC and 0.5% SDS at 65° C.

EXAMPLE 5

Results

An RT-PCR strategy (depicted in FIG. 1) was used to clone and sequence the normal and severe combined immunodeficiency equine DNA-dependent protein kinase$_{catalytic}$ subunit transcripts. Amplification primers were based upon the published human DNA-dependent protein kinase$_{catalytic}$ subunit sequence. cDNA was derived from two fibroblast cell lines, 0176 (derived from a normal, non-Arabian animal) and 1821 (derived from a severe combined immunodeficiency foal). Previously, it was demonstrated that 1) the 1821 cell line was hypersensitive to ionizing radiation, 2) had no detectable DNA-dependent protein kinase activity, 3) lacks DNA-dependent protein kinase$_{catalytic}$ subunit protein, and 4) could not support RAG-induced recombination as assayed by signal joint formation.

Six overlapping cDNA fragments were isolated from the 0176 cell line; ten overlapping cDNA fragments were isolated from the 1821 cell line. Using this strategy, 11,811 nucleotides of the 12,381 DNA-dependent protein kinase-$_{catalytic}$ subunit transcript were sequenced. Isolation of the first 570 bp of the two equine transcripts was unsuccessful using this strategy. This may indicate less evolutionary conservation of this region between the human and equine DNA-dependent protein kinase$_{catalytic}$ subunit genes.

The deduced amino acid sequence of equine DNA-dependent protein kinase$_{catalytic}$ subunit is compared to the human counterpart in FIG. 2. Overall, the two proteins are 84% homologous. There are several small insertions within the equine transcript adding an additional 6 codons. Though the PI3K domain is well conserved between the human and equine sequences (87%), homology within this region was not dramatically higher than throughout the rest of the protein. The region within the PI3K domain corresponding to the putative kinase active site was slightly more conserved. This corresponds to subdomain II as noted by Poltoratsky et al. which includes the conserved protein kinase motifs; homology within this subdomain between human and equine DNA-dependent protein kinase$_{catalytic}$ subunit is 92%. The leucine residues comprising a potential leucine zipper motif noted by Hartley et al. were completely conserved in the equine protein. Similarly, 17 of 18 potential DNA-dependent protein kinase autophosphorylation sites noted by Hartley et al. were also conserved.

Figure 3:
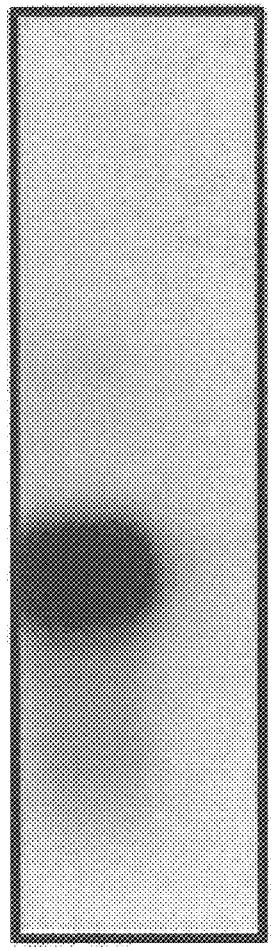
FIG. 3 shows the results of RT-PCR analysis of the DNA-dependent protein kinase$_{catalytic}$ subunit mutation. RT-PCR was performed on cDNA derived from the 0176 (normal) and 1821 (SCID) cell lines using primer combination 396/392. Amplified products were electrophoresed on agarose gels and transferred to nylon membranes. One filter was hybridized with the N probe (left panel) and the other with the S probe (right panel).
Figure 3:
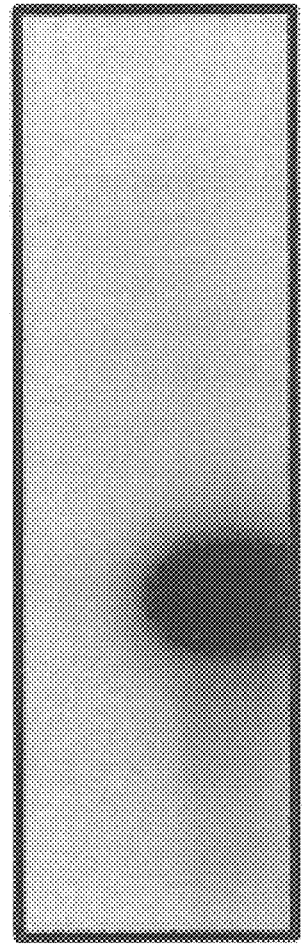

In the RT-PCR fragment spanning nucleotide ~8000 to ~9650 from the 1821 severe combined immunodeficiency cell line, a nucleotide deletion was found. To rule out the possibility that this deletion was the result of a Taq polymerase error, this region was amplified again from both the 0176 and 1821 cell lines (FIG. 3). Two oligonucleotides spanning this region representing the normal (N probe) and severe combined immunodeficiency (S probe) sequences were synthesized. As can be seen, the product amplified from the normal cell line, 0176, hybridizes well with probe N but not at all with probe S. In contrast, the product amplified from the severe combined immunodeficiency cell line, 1821, hybridizes exclusively with the S probe.

Figure 4A:
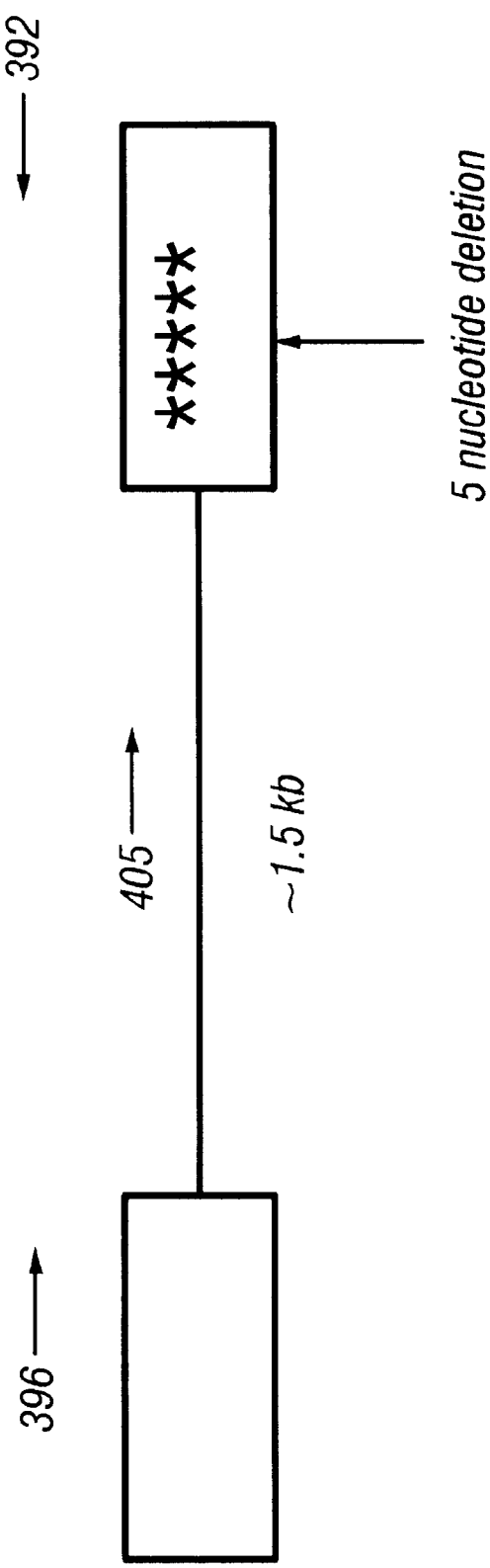
FIG. 4A is a diagramatic depiction of the strategy used to determine the intron/exon organization of the region including the mutated DNA-dependent protein kinase$_{catalytic}$ subunit exon.
Figure 4C:
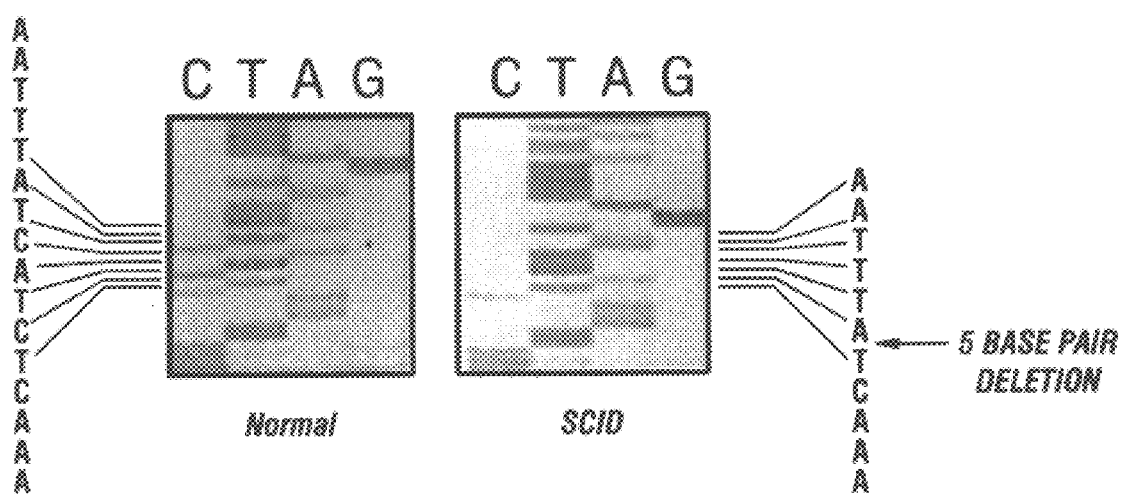
FIG. 4C shows the sequence comparison of the genomic fragments isolated from the 1821 and 0176 cell lines. These splice acceptor site is underlined. Positions of amplification primers are denoted with arrows.

Next, germline sequences encoding this region were isolated by amplifying spleen DNA derived from a severe combined immunodeficiency foal with oligonucleotides spanning the deletion. A 1.8 kB fragment including portions of two exons and a 1.5 kB intron was cloned (depicted in FIGS. 4A–C). The intron exon border of the exon containing the 5 bp deletion was determined. Genomic fragments spanning this region from the 0176 and 1821 cell lines were cloned; sequence analysis of the normal allele and severe combined immunodeficiency allele is shown in FIG. 4C, confirming this 5 bp deletion in DNA derived from the 1821 cell line.

Next, it was determined whether this 5 bp deletion accounts for severe combined immunodeficiency in many Arabian foals, or just a subset of affected animals. To that end, genomic DNA was derived from eight different severe combined immunodeficiency foals and five normal animals (four Arabian and one non-Arabian). For the severe combined immunodeficiency animals, the diagnosis of severe combined immunodeficiency was established on the basis of lymphopenia (<1,000 lymphocytes/µl peripheral blood), absence of IgM, and hypoplasia of lymphoid tissues as described previously. The eight severe combined immunodeficiency foals were derived from eight different mares and sired by three different stallions. The adult heterozygotes were obtained from across the USA and were not related to one another.

Figure 5:
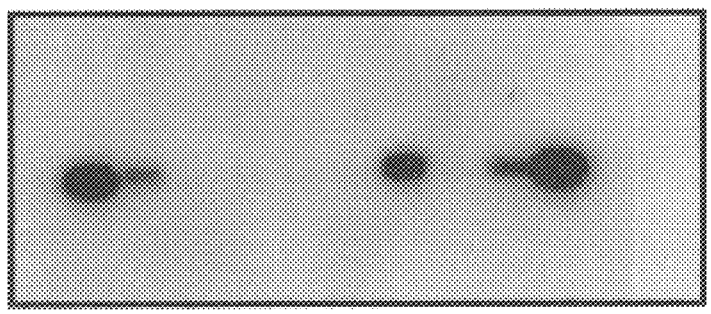
FIG. 5 shows the genomic PCR analysis of DNA derived from SCID and phenotypically normal animals using primer combinations 392/405. Amplified products were electrophoresed on agarose gels and transferred to nylon membranes. One filter was hybridized with the N probe (top panel) and the other with the S probe (bottom panel). Phenotype and genotype (as determined b y this analysis) is indicated. S denotes SCID; N denotes normal; H denotes heterozygote.
Figure 5:
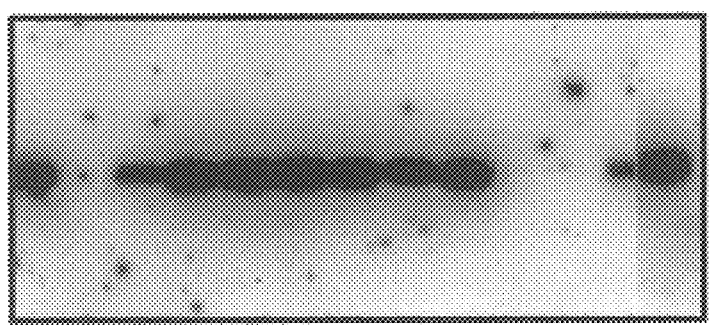

As can be seen in FIG. 5, in all severe combined immunodeficiency foals tested the probe specific for the 5 b p deletion hybridizes strongly; the probe specific for the normal allele does not hybridize at all. Furthermore, in all samples derived from normal animals, the hybridization probe derived from the normal allele hybridizes strongly. In two normal animals, both the N probe and the S probes hybridize well identifying these two animals a s heterozygotes. From these data, it can be concluded that this specific 5 bp mutation is responsible for a significant fraction of the cases of severe combined immunodeficiency in Arabian horses.

Severe combined immunodeficiency in Arabian foals was first described by McGuire and Poppie in 1973 and the mechanistic defect in these animals is V(D)J recombination and double strand break repair has now been demonstrated. The present invention establishes that the factor responsible for this genetic disease is a truncated form of the catalytic subunit of the DNA dependent protein kinase. Unlike the situation in the human disease ataxia telangiectasia, where mutations in the ATM gene (another PI3K family member) occur throughout the protein, in all severe combined immunodeficiency foals examined to date, the same mutation exists. Thus, since eight unrelated severe combined immunodeficiency foals have the identical DNA-dependent protein kinase$_{catalytic}$ subunit mutation it is likely that this DNA-dependent protein kinase$_{catalytic}$ subunit allele has common origins and because of a bottleneck in breeding results in a genetic "founder" effect.

Since there are several clear mechanistic differences between mice and horses, the finding that DNA-dependent protein kinase$_{catalytic}$ subunit levels were severely diminished in both was initially paradoxical. The differences between severe combined immunodeficiency mice and severe combined immunodeficiency foals are actually twofold. First, in severe combined immunodeficiency foals, both signal and coding joint ligation is impaired; whereas signal ligation is relatively normal in severe combined immunodeficiency mice. In addition, by limiting dilution PCR analysis, it was determined that coding ligation is more severely impaired in severe combined immunodeficiency foals than in severe combined immunodeficiency mice. Whereas it is very easy to detect some coding ligation in severe combined immunodeficiency mice ("leaky" severe combined immunodeficiency phenotype), demonstration of any coding joint formation in severe combined immunodeficiency foals is exceedingly difficult. Thus, it was thought originally that the defective factors in these two animal models of severe combined immunodeficiency might be distinct. The definition of the specific DNA-dependent protein kinase$_{catalytic}$ subunit mutation in equine severe combined immunodeficiency coupled with the description of the precise mutation responsible for murine severe combined immunodeficiency provide a good explanation for the mechanistic differences observed between severe combined immunodeficiency mice and severe combined immunodeficiency horses.

Figure 6:
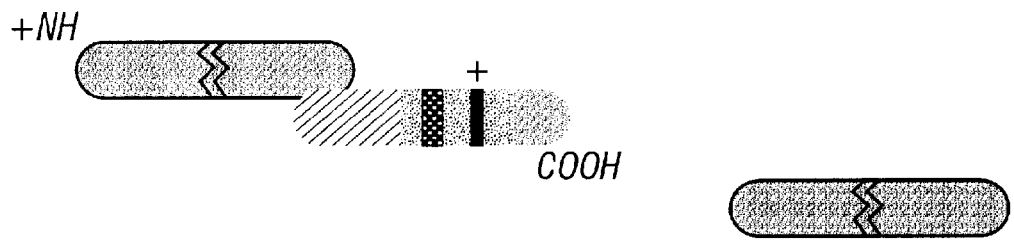
FIG. 6 is a the diagrammatic representation of DNA-dependent protein kinase$_{catalytic}$ subunit isoforms generated by PI3K splice variation. Subregions of homology to other PI3K family members are as noted by Poltoratsky et al. The murine SCID mutation results in an 80 amino acid truncation which leaves the PI3K domain intact. The equine SCID mutation results in a 967 amino acid truncation which deletes the PI3K domain.
Figure 6:
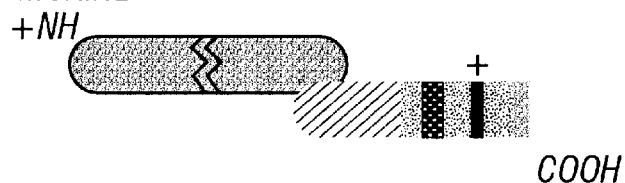
Figure 6:
Figure 6:
Figure 6:
Figure 6:
Figure 6:

FIG. 6 depicts the result of the equine DNA-dependent protein kinase$_{catalytic}$ subunit mutation and the murine severe combined immunodeficiency mutation described earlier this year b y Blunt et al. and Danska et al. The difference in the two mutated forms of DNA-dependent protein kinase-$_{catalytic}$ subunit is dramatic. In the murine mutation, the conserved regions shared between DNA-dependent protein kinase$_{catalytic}$ subunit and other PI3 kinase family members are intact. This region is absent in the mutated equine protein. Thus, in cells from severe combined immunodeficiency foals, there can clearly be no DNA-dependent kinase activity; however, since the mutation in severe combined immunodeficiency mice preserves most of the PI3K homology domain, some kinase activity may be present.

The description of defective signal ligation in severe combined immunodeficiency foals is not the only evidence linking DNA-dependent protein kinase$_{catalytic}$ subunit to signal ligation. The double strand break repair mutant cell line V3 also has diminished (though not absent) signal end resolution. As in murine severe combined immunodeficiency cells, in V3 cells some protein immunoreactive with anti-DNA-dependent protein kinase$_{catalytic}$ subunit antibodies can be detected. Thus, an attractive hypothesis is that preferentially-defective coding versus signal resolution may result from diminished levels of DNA-dependent protein kinase kinase activity; whereas absence of DNA-dependent protein kinase activity impairs both signal and coding ligation. In support of that conclusion, Errami et al. recently demonstrated that cells which are completely defective in the regulatory subunit of DNA-dependent protein kinase, Ku (specifically in the 86 kD subunit of Ku), which were transfected with low levels of Ku80 are like mouse severe combined immunodeficiency cells, preferentially defective in coding joint ligation. Thus, this hypothesis can be extended in that preferentially defective coding versus signal resolution may result from diminished levels of any component of DNA-dependent protein kinase; whereas absence of any component of DNA-dependent protein kinase impairs both signal and coding ligation.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An oligonucleotide of 15 to 25 bases that hybridizes to the severe combined immunodeficiency (SCID) determinant region of nucleic acid encoding the DNA-dependent protein kinase$_{catalytic\ subunit}$ in Arabian horses (SEQ ID No:28).

2. The oligonucleotide of claim 1, wherein said oligonucleotide comprises a label.

3. The oligonucleotide of claim 2, wherein said label is a radioactive element, a fluorescent material or an enzyme.

4. A primer pair that amplifies the severe combined immunodeficiency (SCID) determinant region of nucleic acid encoding the DNA-dependent protein kinase$_{catalytic\ subunit}$ in Arabian horses (SEQ ID No:28).

5. A method of identifying an Arabian horse that is a cater for equine severe combined immunodeficiency comprising determining the presence or absence of a gene encoding a functional DNA-dependent protein kinase$_{catalytic\ subunit}$ in Arabian horses (SEQ ID No:28).

6. The method of claim 5, wherein said determining comprises differential hybridization.

7. The method of claim 5, wherein said determining comprises DNA amplification.

8. A method of identifying an Arabian horse that is a carrier of equine severe combined immunodeficiency comprising the step of determining whether said horse has a mutation in the severe combined immunodeficiency (SCID) determinant region of nucleic acid encoding the DNA-dependent protein kinase$_{catalytic\ subunit}$ in Arabian horses (SEQ ID No:28).

9. The method of claim 8, wherein said determining comprises differential hybridization.

10. The method of claim 8, wherein said determining comprises DNA amplification.

11. A method of identifying an Arabian horse that is a cattier of equine severe combined immunodeficiency comprising the step of determining whether said horse carries the severe combined immunodeficiency (SCID) allele of the DNA-dependent protein kinase$_{catalytic\ subunit}$ in Arabian horses, said allele comprising SEQ ID No:25.

12. The method of claim 11, wherein said determining comprises differential hybridization.

13. The method of claim 11, wherein said determining comprises DNA amplification.

14. An isolated DNA molecule encoding a DNA-dependent protein kinase$_{catalytic\ subunit}$ of SEQ ID No:29.

* * * * *

UNITED STATES PATENT AND TRADEMARK OFFICE
CERTIFICATE OF CORRECTION

PATENT NO.      : 6,294,334 B1
DATED           : September 25, 2001
INVENTOR(S)     : Katheryn D. Meek It is certified that error appears in the above-identified patent and that said Letters Patent is hereby corrected as shown below:

Column 101, claim 5,
Line 14, please delete "cater" and insert -- carrier -- therefor.

Column 102, claim 11,
Line 12, please delete "cattier" and insert -- carrier -- therefor.

Signed and Sealed this

Sixteenth Day of April, 2002

Attest:

Attesting Officer

JAMES E. ROGAN
*Director of the United States Patent and Trademark Office*